US010066007B2

(12) United States Patent
Edbauer et al.

(10) Patent No.: US 10,066,007 B2
(45) Date of Patent: Sep. 4, 2018

(54) DIPEPTIDE-REPEAT PROTEINS AS THERAPEUTIC TARGET IN NEURODEGENERATIVE DISEASES WITH HEXANUCLEOTIDE REPEAT EXPANSION

(71) Applicant: DEUTSCHES ZENTRUM FÜR NEURODEGENERATIVE ERKRANKUNGEN E.V. (DZNE), Bonn (DE)

(72) Inventors: Dieter Edbauer, Germering (DE); Christian Haass, Icking (DE); Shih-Ming Weng, Taipei (TW); Kohji Mori, Munich (DE); Thomas Arzberger, Baldham (DE); Elisabeth Kremmer, Munich (DE)

(73) Assignee: DEUTSCHES ZENTRUM FÜR NEURODEGENERATIVE ERKRANKUNGEN E.V. (DZNE), Bonn (DE)

( * ) Notice: Subject to any disclaimer, the term of this patent is extended or adjusted under 35 U.S.C. 154(b) by 11 days.

(21) Appl. No.: 14/762,623

(22) PCT Filed: Jan. 22, 2014

(86) PCT No.: PCT/EP2014/051204
§ 371 (c)(1),
(2) Date: Jul. 22, 2015

(87) PCT Pub. No.: WO2014/114660
PCT Pub. Date: Jul. 31, 2014

(65) Prior Publication Data
US 2015/0361166 A1  Dec. 17, 2015

(30) Foreign Application Priority Data

Jan. 22, 2013 (WO) ................ PCT/EP2013/000190
Sep. 20, 2013 (EP) ..................................... 13185419

(51) Int. Cl.
*C07K 16/18* (2006.01)
*G01N 33/68* (2006.01)
*C07K 14/47* (2006.01)

(52) U.S. Cl.
CPC ............. *C07K 16/18* (2013.01); *C07K 14/47* (2013.01); *G01N 33/6893* (2013.01); *G01N 33/6896* (2013.01); *C07K 2317/20* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| 2004/0102608 A1 | 5/2004 | Rathore et al. | |
| 2009/0136912 A1* | 5/2009 | Kurokawa | C12N 5/0075 435/1.1 |
| 2015/0259679 A1* | 9/2015 | Bennett | C12N 15/113 514/44 A |

FOREIGN PATENT DOCUMENTS

| EP | 1 270 724 | 1/2003 |
| EP | 1 739 167 | 1/2007 |
| WO | WO 2011/144756 | 11/2011 |

OTHER PUBLICATIONS

Acosta-Serrano 2001 "The surface coat of procyclic trypanosoma brucei: programmed expression and proteolytic cleavage of procyclin in the tse tse fly" PNAS 98(4):1513-1518.*
Renton 2011 "A hexanucleotide repeat expansion in c9orf72 is the cause of chromosome 9p21-linked als-ftd" Neuron 72(2):254-268.*
Chen 1995 "enhancement and destruction of antibody function by somatic mutation:unequal occurance is controlled by v gene combinatorial associations" EMBO 14(12):2784-2794.*
Hernandez 2011 "Expanded GGGGCC hexanucleotide repeat in non-coding region of C9ORF72 causes chromosome 9p-linked frontotemporal dementia and amyotrophic lateral sclerosis" Neuron 72(2): 245-256.*
Kussie 1994 "single engineered amino acid substitution changes antibody fine specificity" J immunol 152(1):146-52.*
Wang 2016 "protein/peptide secondary structure mimics: design, characterization, and modulation of protein-protein interactions" RSC advances 6:61599.*
Dillner, J., et al., "Antibodies against a synthetic peptide identify the Epstein-Barr virus-determined nuclear antigen" *Proceedings of the National Academy of Sciences of the United States of America*, Aug. 1984, vol. 81, No. 15, pp. 4652-4656.
Kobayashi, H., et al., "Expansion of Intronic GGCCTG Hexanucleotide Repeat in NOP56 Causes SCA36, a Type of Spinocerebellar Ataxia Accompanied by Motor Neuron Involvement" *The American Journal of Human Genetics*, Jul. 15, 2011, vol. 89, No. 1, pp. 121-130.
Nagafuchi, S., et al., "Structure and expression of the gene responsible for the triplet repeat disorder, dentatorubral and pallidoluysian atrophy (DRPLA)" *Nature Genetics*, Oct. 1994, vol. 8, No. 2, pp. 177-182.
Written Opinion in International Application No. PCT/EP2014/051204, dated Jul. 14, 2014, pp. 1-9.
Kremmer, E. et al. "Rat Monoclonal Antibodies Differentiating between the Epstein-Barr Virus Nuclear Antigens 2A (EBNA2A) and 28 (EBNA2B)" *Virology*, 1995, pp. 336-342, vol. 208.
Heap, C. et al. "Analysis of a 17-amino acid residue, virus-neutralizing microantibody" *Journal of General Virology*, 2005, pp. 1791-1800, vol. 86.
Qiu, X.-Q. et al. "Small antibody mimetics comprising two complementarity-determining regions and a framework region for tumor targeting" *Nature Biotechnology*, Aug. 2007, pp. 921-929, vol. 25, No. 8.

* cited by examiner

*Primary Examiner* — Adam M Weidner
(74) *Attorney, Agent, or Firm* — Saliwanchik, Lloyd & Eisenschenk

(57) ABSTRACT

The present invention relates to a method of detecting a disease characterized by an expansion of genomic hexanucleotide repeats as well as polypeptides of said hexanucleotide repeats, ligands specifically binding to the polypeptides, and to methods of identifying an inhibitor preventing the expression and/or aggregation of said polypeptide.

5 Claims, 12 Drawing Sheets
Specification includes a Sequence Listing.

Fig. 2

| Case | Region | DPR | | | p62 | TDP-43 | Diagnosis | GGGGCC repeat expansion | Source |
| --- | --- | --- | --- | --- | --- | --- | --- | --- | --- |
| | | GA | GP | GR | | | | | |
| TJ-1 | Hippocampus | + | + | + | + | + | FTLD/ALS-TDP | + | LMU |
| | Cerebellum | + | + | + | + | - | | | LMU |
| TJ-2 | Hippocampus | + | + | + | + | + | FTLD/ALS-TDP | + | LMU |
| | Cerebellum | + | + | + | + | - | | | LMU |
| TJ-3 | Hippocampus | + | + | + | + | + | FTLD/ALS-TDP | + | LMU |
| | Cerebellum | + | + | + | + | - | | | LMU |
| TJ-4 | Hippocampus | + | + | + | + | + | FTLD-TDP | + | LMU |
| | Cerebellum | + | + | + | + | - | | | LMU |
| TJ-5 | Hippocampus | + | + | + | + | + | FTLD/ALS-TDP | + | LMU |
| | Cerebellum | + | + | + | + | - | | | LMU |
| TJ-6 | Cerebellum | NA | NA | NA | NA | NA | FTLD/ALS-TDP | + | LMU |
| TJ-10 | Cortex | + | + | + | + | - | FTLD-UPS | + | VIB |
| TJ-11 | Hippocampus | - | - | - | + | - | Huntington | NA | LMU |
| | frontal cortex | - | - | - | + | NE | | | LMU |
| TJ-12 | Hippocampus | - | - | - | + | - | Huntington | NA | LMU |
| | frontal cortex | - | - | - | + | NE | | | LMU |
| TJ-13 | Hippocampus | - | - | - | + | + | FTLD-TDP | - | LMU |
| | cerebellum | - | - | - | - | - | | | LMU |
| TJ-14 | Hippocampus | - | - | - | + | + | FTLD-TDP | - | LMU |
| | Cerebellum | - | - | - | - | - | | | LMU |
| TJ-15 | Hippocampus | - | - | - | + | + | ALS-TDP | - | LMU |
| | cerebellum | - | - | - | - | - | | | LMU |
| TJ-16 | Hippocampus | - | - | - | + | + | ALS-TDP | - | LMU |
| | cerebellum | - | - | - | - | - | | | LMU |
| TJ-17 | Hippocampus | - | - | - | - | - | Control | - | LMU |
| | cerebellum | - | - | - | NE | NE | | | LMU |
| TJ-18 | Hippocampus | - | - | - | - | - | Control | - | LMU |
| | cerebellum | - | - | - | NE | NE | | | LMU |
| TJ-21 | cortex | - | - | - | - | - | Control | - | VIB |

Fig. 10

| | Identified Proteins | Accession Number | Average Quantitative Value | | | GC/AC ratio |
|---|---|---|---|---|---|---|
| | | | AC | GC | Competition | |
| 1 | Heterogeneous nuclear ribonucleoproteins A2/B1 | ROA2_HUMAN | 110.3 | 369.8 | 1.7 | 3.4 |
| 2 | Splicing factor, proline- and glutamine-rich | SFPQ_HUMAN | 51.7 | 130.5 | 0.1 | 2.5 |
| 3 | Splicing factor 3B subunit 3 | SF3B3_HUMAN | 51.1 | 118.8 | 6.3 | 2.3 |
| 4 | ELAV-like protein 1; (Hu-antigen R) | ELAV1_HUMAN | 9.6 | 117.1 | 0.0 | 12.1 |
| 5 | Interleukin enhancer-binding factor 3 | ILF3_HUMAN | 24.7 | 87.4 | 0.0 | 3.5 |
| 6 | Non-POU domain-containing octamer-binding protein | NONO_HUMAN | 13.4 | 80.4 | 0.0 | 6.0 |
| 7 | Heterogeneous nuclear ribonucleoprotein R | HNRPR_HUMAN | 28.8 | 74.1 | 0.0 | 2.6 |
| 8 | Heterogeneous nuclear ribonucleoprotein A3 | ROA3_HUMAN | 23.8 | 70.6 | 0.0 | 3.0 |
| 9 | Heterogeneous nuclear ribonucleoprotein L | HNRPL_HUMAN | 21.7 | 57.2 | 0.0 | 2.6 |
| 10 | Scaffold attachment factor B1 | SAFB1_HUMAN | 27.5 | 55.0 | 0.0 | 2.0 |
| 11 | Insulin-like growth factor 2 mRNA-binding protein 1 (IMP1) | IF2B1_HUMAN | 19.5 | 47.9 | 0.6 | 2.5 |
| 12 | Scaffold attachment factor B2 | SAFB2_HUMAN | 20.0 | 45.0 | 0.0 | 2.3 |
| 13 | Heterogeneous nuclear ribonucleoprotein A1 | ROA1_HUMAN | 20.8 | 44.9 | 0.1 | 2.2 |
| 14 | Double-stranded RNA-specific adenosine deaminase (ADAR1 | DSRAD_HUMAN | 16.5 | 42.3 | 0.3 | 2.6 |
| 15 | Putative pre-mRNA-splicing factor ATP-dependent RNA | DHX15_HUMAN | 13.0 | 31.0 | 1.0 | 2.4 |
| 16 | Interleukin enhancer-binding factor 2 | ILF2_HUMAN | 8.3 | 25.3 | 0.0 | 3.0 |
| 17 | Putative ATP-dependent RNA helicase DHX30 | DHX30_HUMAN | 6.3 | 23.5 | 0.0 | 3.8 |
| 18 | Heterogeneous nuclear ribonucleoprotein K | HNRPK_HUMAN | 10.7 | 23.2 | 0.0 | 2.2 |
| 19 | Nucleolar RNA helicase 2 | DDX21_HUMAN | 7.5 | 23.0 | 0.7 | 3.1 |
| 20 | RNA-binding protein FUS | FUS_HUMAN | 7.0 | 20.0 | 0.0 | 2.9 |

Fig. 11
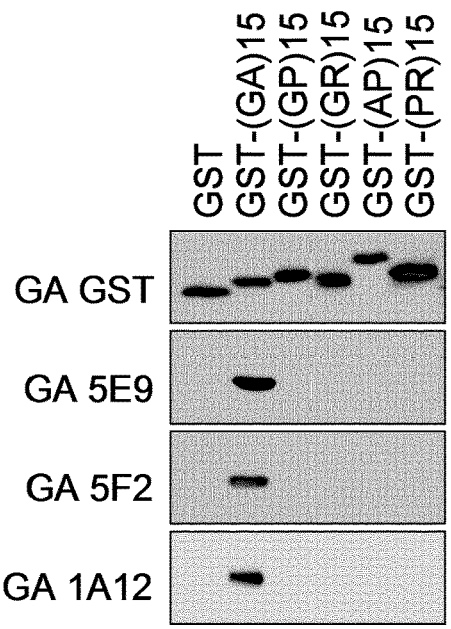
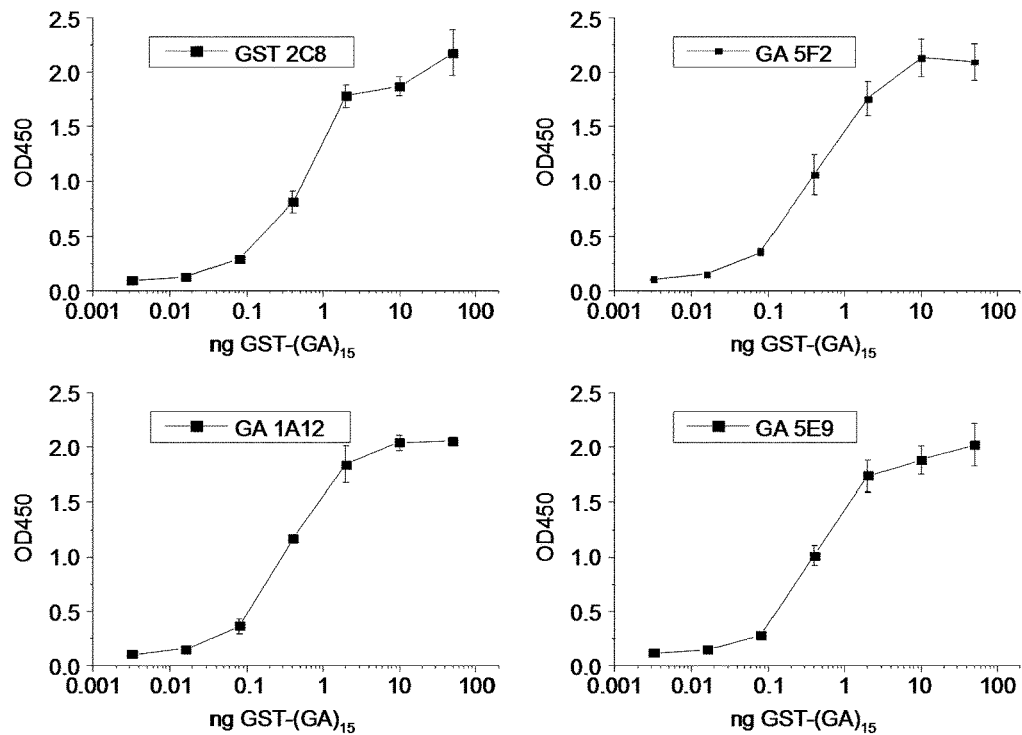

Fig. 12

Sequences of the variable regions of heavy and light chains

Light chain variable region (LCVR) sequence:

ivisqdelsnpvtsgesvsiscRSSKSLLYKDGKTYLNwflqrpgqspqlliyLMSTRASgvsdrfsgsgsgtdftl
eisrvkaedvgvyfcQQLVEYPLTfgagtklel

Heavy chain variable region (HCVR) GA 1A12 sequence:

lqqsgaelmkpgasvklscrssGYTFTGYWIEwvkqrpghglewigEILPGSGSTKynenfrgkatftadtssntay
irlsslttedsaiyfcarGDFTNSHFAYwgqgtlvtvs

Heavy chain variable region (HCVR) GA 5E9 sequence:

lqqsgaevmkpgasvklsckvtGYTFTGYWIEwvkqrpghglewigENLPGSGSTKynekfkgkatftadtssnt
aymqlssltiedsaiyycarGDYSNSHFAYwgqgtlvtvs

Heavy chain variable region (HCVR) GA 5F2 sequence:

lqqsgvelmkpgasvklsckstGYKFIGYWIEwvkqrpghglewigENLPGSGTTKynenfrgkatftadtssnta
ymqlssltiedsaiyycarGDYSNSHFTYwgqgtlvtvs

DIPEPTIDE-REPEAT PROTEINS AS THERAPEUTIC TARGET IN NEURODEGENERATIVE DISEASES WITH HEXANUCLEOTIDE REPEAT EXPANSION

CROSS-REFERENCE TO RELATED APPLICATION

This application is the U.S. national stage application of International Patent Application No. PCT/EP2014/051204, filed Jan. 22, 2014.

The Sequence Listing for this application is labeled "Seq-List.txt" which was created on Jul. 21, 2015 and is 43 KB. The entire contents of the sequence listing is incorporated herein by reference in its entirety.

The present invention relates to a method of detecting a disease characterized by an expansion of genomic hexanucleotide repeats as well as polypeptides of said hexanucleotide repeats, ligands specifically binding to the polypeptide, methods of identifying an inhibitor preventing the expression, toxicity and/or aggregation of said polypeptide.

BACKGROUND OF THE INVENTION

Neurodegenerative disorders are generally characterized by disease signifying protein deposits. Moreover, in a number of neurodegenerative diseases mutations causing genetically inherited variants of the disease were associated with the genes encoding the protein deposits, their precursors or their modulating enzymes. Functional analysis of these genetic variants fundamentally helped to understand disease associated mechanisms of Alzheimer's disease (AD) and Parkinson's disease (Gasser et al., 2011, Haass et al., 2007). Frontotemporal lobar degeneration (FTLD) and amyotrophic lateral sclerosis (ALS) are the extreme ends of a spectrum of overlapping neurodegenerative disorders variably associated with dementia, personality changes, language abnormalities and progressive muscle weakness (Josephs et al., 2011; Mackenzie et al., 2010; Rademakers et al., 2012). Research into ALS and FTLD was dramatically accelerated by the identification of the RNA/DNA binding protein TDP-43 (Tar DNA binding protein of 43 kDa) as an abundant deposited protein (Arai et al., 2011; Neumann et al., 2006) and by the discovery that mutations in TARDBP cause familial variants of both diseases (Benajiba et al., 2009; Sreedharan et al., 2008). The majority of cases show intracellular inclusions that are strongly positive for phosphorylated TDP-43. These findings also helped to develop the concept that ALS and FTLD are multisystem disorders with overlapping clinical and pathological characteristics and similar functional and genetic causes (Rademakers et al., 2012; Sieben et al., 2012) and which are therefore classified as FTLD-TDP, FTLD/ALS-TDP or ALS-TDP. Besides TDP-43, and the long known SOD1 (super oxide dismutase 1) gene, a number of other ALS and/or FTLD related genes/risk factors were discovered including FUS (Fused in Sarcoma), OPTN (optineurin), Ataxin 2, Chmp2B, VCP (Valosin containing protein), TMEM106B, GRN (Progranulin), PFN (Profilin) and the C9orf72 gene. Pathological repeat expansions in C9orf72 have been found in about 40% of familial ALS patients and 20% of familial FTLD, demonstrating that C9orf72 is the most common genetic cause for these incurable disorders.

Recently, expansion of a GGGGCC hexanucleotide repeat in the C9orf72 gene has been identified as the most common pathogenic mutation in families with autosomal dominant FTLD, FTLD/ALS and ALS (DeJesus-Hernandez et al. 2011; Renton et al. 2011; Gijselinck et al. 2012). It was further revealed that the hexanucleotide repeat expansion within the regulatory region of the gene C9orf72 is the most common cause of familial amyotrophic lateral sclerosis and the second most common cause of frontotemporal lobar degeneration. The hexanucleotide repeat expansion is located upstream of the C9orf72 open reading frame, either in the first intron or the promoter region, depending on the transcript isoform (see FIG. 8A). Although the extreme GC-content precludes sequencing in patients, the number of GGGGCC repeat units is believed to be at least several hundred compared to less than 25 in healthy controls (van der Zee et al. 2012). The pathomechanisms leading to disease however remained unclear.

Patients with a C9orf72 repeat expansion have clinical symptoms similar to other FTLD/ALS-TDP patients, but show several unique pathological features (Al-Sarraj et al. 2011; Boxer et al. 2011; Bigio et al. 2012; Whitwell et al. 2012). Aggregates of phosphorylated TDP-43 are accompanied by abundant dot-like and star-shaped phospho-TDP-43-negative neuronal cytoplasmic inclusions in particular in the cerebellum, hippocampus and frontotemporal neocortex that can only be identified with antibodies for p62, ubiquitin or the related ubiquilins. These phospho-TDP-43 negative aggregates are highly characteristic of diseased C9orf72 mutation carriers and are absent in other variants of FTLD/ALS-TDP. The identity of the disease protein(s) in these inclusions and their relation to the C9orf72 hexanucleotide repeat expansion has remained elusive. From research on other neurodegenerative diseases with repeat expansion outside the open reading frame two main pathomechanism have been proposed.

Repeat expansions in non-coding regulatory regions of genes is thought to cause a disease by two different mechanisms that are not mutually exclusive. First, due to the immense length of the repeat expansion transcription and/or splicing may be affected leading to haploinsufficiency (van der Zee et al. 2012). Second, RNA toxicity caused by sequestration of RNA binding proteins may also be causative (Ranum et al., 2006). Currently, evidence for both possibilities exists. The observation of nuclear RNA foci in patients with GGGGCC hexanucleotide repeat expansions, a finding which however is still controversially discussed, suggests that trapping of essential RNA binding proteins may be involved in the disease. Moreover, the finding of decreased expression of C9orf72 mRNA and decreased transcriptional activity of the C9orf72 promoter on intermediate (7-24 repeats) alleles (DeJesus-Hernandez et al. 2011; Gijselinck et al. 2012; van der Zee et al. 2012) implies a loss of function as a disease causing mechanism. These scenarios are not mutually exclusive and may even occur in parallel.

It is unclear how the C9orf72 repeat expansion leads to the characteristic p62-positive/TDP-43-negative inclusions and the subsequent neurodegeneration. There are over 150 papers on C9orf72 genetics and pathology. However, functional data are still very limited.

We disclose herein for the first time that most of these characteristic inclusions contain poly-(Gly-Ala) and to a lesser extent poly-(Gly-Pro) and poly-(Gly-Arg) dipeptide-repeat proteins (DPR) which are generated by non-ATG-initiated translation from the expanded GGGGCC repeats in three reading frames. These findings directly link the FTLD/ALS-associated genetic mutation to the characteristic pathology in patients with C9orf72 hexanucleotide expansion.

So far there is only evidence of a non-ATG-initiated translation of exonic repeat regions in two diseases (Zu et al.

2011). ATXN8 encodes a natural poly-Q stretch that can cause poly-Q inclusions upon repeat expansion in spinocerebellar ataxia type 8 (SCA8) patients. The expanded CAG-repeat is translated in all three reading frames (poly-Q, poly-A and poly-S) even after removal of the endogenous start codon. Poly-Q and poly-A have been found in patient aggregates. Furthermore, myotonic dystrophy type 1 (DM1) is caused by CTG-expansion in the 3'UTR of the gene DMPK. The translation into rare poly-Q aggregates in DM1 patients and mouse models was discovered. The underlying mechanism was named repeat-associated non-ATG-initiated translation (RAN) and is patented for tri-, tetra-, and pentanucleotide repeat disorders (WO2010/115033 A9). RAN translation has not been shown for intronic repeats or hexanucleotide repeats. In one commentary article Laura Ranum speculates about RAN-translation in C9orf72 patients (Ashizawa and Ranum 2012). It is also possible that translation of DPR proteins is initiated from non-canonical start codon 5' of the repeat region (Ivanov, I. P. et al. 2011; Peabody D. S. 1989; Touriol C. et al., 2003)

We show for the first time a non-ATG-initiated translation of an intronic repeat expansion, which causes p62-positive/TDP43-negative aggregates of poly-GA, poly-GP and poly-GR. This unusual translation mechanism and the highly abnormal product will facilitate more selective therapeutic approaches than possible for other neurodegenerative diseases. Inhibiting the abnormal dipeptide-repeat protein generation or aggregation will prevent or delay disease progression in mutation carriers. DPR pathology can be used to prevent, delay or cure FTD/ALS in C9orf72 mutation carriers by destabilizing the C9ORF72 (intronic) RNA specifically (e.g., siRNA, anti-sense, alter C9orf72 splicing), inhibiting repeat transcription and/or translation into DPR (screen for RAN-specific translation inhibitors), and preventing DPR aggregation or promoting degradation or clearance (through chemical compounds or immunotherapy).

Similar mechanisms are likely to apply for SCA36, caused by GGCCTG hexanucleotide expansion in NOP56 (Kobayashi et al. 2011). Some of the reading frames encode DPRs as in C9orf72, poly-GP and poly-PR, however with different flanking regions. Therefore, therapeutic drugs discovered for C9orf72 patients are likely to be useful for SCA36 patients too.

SUMMARY OF THE INVENTION

In a first aspect the present invention provides a method of detecting a disease characterized by an expansion of genomic hexanucleotide repeats comprising:
(i) providing a sample from a patient suspected of having or being susceptible to a disease characterized by an expansion of genomic hexanucleotide repeats, and
(ii) detecting expression of one or more polypeptides comprising dipeptide repeats encoded by the genomic hexanucleotide repeats,
wherein the expression of said polypeptide indicates the presence of or susceptibility to a disease characterized by an expansion of genomic hexanucleotide repeats.

In a second aspect the present invention provides a polypeptide comprising or consisting of dipeptide repeats with a sequence selected from the group consisting of (Gly-Ala)$_a$, (Gly-Pro)$_b$, (Gly-Arg)$_c$, (Ala-Pro)$_d$, (Pro-Arg)$_e$, (Gly-Leu)$_f$, (Ala-Trp)$_g$, (Pro-Gly)$_h$, (Ala-Gln)$_j$, (Gly-Pro)$_k$, and (Pro-Arg)$_l$ wherein a is an integer of 16 or more, b is an integer of 28 or more, c is an integer of 21 or more, d is an integer 17 or more, e is an integer of 24 or more, f is an integer of 15 or more, g is an integer of 9 or more, h is an integer of 28 or more, j is an integer of 16 or more, k is an integer of 28 or more, and l is an integer of 24 or more.

In a third aspect the present invention provides a polypeptide comprising or consisting of:
(i) (Gly-Ala)$_m$ dipeptide repeats, wherein m is an integer of 10 or more, at least three contiguous amino acids of the amino acid sequences according to SEQ ID NO: 3 are comprised at its C-terminus, and/or at least three contiguous amino acids of the amino acid sequences according to SEQ ID NO: 14 are comprised at its N-terminus,
(ii) (Gly-Pro)$_o$ dipeptide repeats, wherein o is an integer of 10 or more, at least three contiguous amino acids of the amino acid sequences according to SEQ ID NO: 4 or are comprised at its C-terminus, and/or at least three contiguous amino acids of the amino acid sequences according to SEQ ID NO: 15 are comprised at its N-terminus,
(iii) (Gly-Arg)$_p$ dipeptide repeats, wherein p is an integer of 10 or more, at least three contiguous amino acids of the amino acid sequences according to SEQ ID NO: 5 are comprised at its C-terminus, and/or at least three contiguous amino acids of the amino acid sequences according to SEQ ID NO: 16 are comprised at its N-terminus,
(iv) (Ala-Pro)$_q$ dipeptide repeats, wherein q is an integer of 10 or more, at least three contiguous amino acids of the amino acid sequences according to SEQ ID NO: 6 are comprised at its C-terminus, and/or at least three contiguous amino acids of the amino acid sequences according to SEQ ID NO: 17 are comprised at its N-terminus,
(v) (Pro-Arg)$_r$ dipeptide repeats, wherein r is an integer of 10 or more, at least three contiguous amino acids of the amino acid sequences according to SEQ ID NO: 7 are comprised at its C-terminus, and/or at least three contiguous amino acids of the amino acid sequences according to SEQ ID NO: 18 are comprised at its N-terminus,
(vi) (Gly-Leu)$_s$ dipeptide repeats, wherein s is an integer of 10 or more, at least three contiguous amino acids of the amino acid sequences according to SEQ ID NO: 8 are comprised at its C-terminus, and/or at least three contiguous amino acids of the amino acid sequences according to SEQ ID NO: 19 are comprised at its N-terminus,
(vii) (Ala-Trp)$_t$ dipeptide repeats, wherein t is an integer of 10 or more, at least three contiguous amino acids of the amino acid sequences according to SEQ ID NO: 9 are comprised at its C-terminus, and/or at least three contiguous amino acids of the amino acid sequences according to SEQ ID NO: 20 are comprised at its N-terminus,
(viii) (Pro-Gly)$_u$ dipeptide repeats, wherein u is an integer of 10 or more, at least three contiguous amino acids of the amino acid sequences according to SEQ ID NO: 10 are comprised at its C-terminus, and/or at least three contiguous amino acids of the amino acid sequences according to SEQ ID NO: 21 are comprised at its N-terminus,
(ix) (Ala-Gln)$_w$ dipeptide repeats, wherein w is an integer of 10 or more, at least three contiguous amino acids of the amino acid sequences according to SEQ ID NO: 11 are comprised at its C-terminus, and/or at least three contiguous amino acids of the amino acid sequences according to SEQ ID NO: 22 are comprised at its N-terminus,
(x) (Gly-Pro)$_x$ dipeptide repeats, wherein x is an integer of 10 or more, at least three contiguous amino acids of the amino acid sequences according to SEQ ID NO: 12 are comprised at its C-terminus, and/or at least three contiguous amino acids of the amino acid sequences according to SEQ ID NO: 23 are comprised at its N-terminus, or
(xi) (Arg-Pro)$_y$ dipeptide repeats, wherein y is an integer of 10 or more, at least three contiguous amino acids of the amino acid sequences according to SEQ ID NO: 13 are comprised at its C-terminus, and/or at least three contiguous amino acids of the amino acid sequences according to SEQ ID NO: 24 are comprised at its N-terminus.

In a fourth aspect the present invention provides a ligand which binds specifically to a polypeptide of the second or third aspect of the present invention.

In a fifth aspect the present invention provides a method of identifying an inhibitor of expression of a polypeptide comprising or consisting of dipeptide repeats, comprising the steps of:
(i) providing a cell comprising a polynucleotide sequence encoding said polypeptide,
(ii) contacting the cell with a potential inhibitor of expression of said polypeptide, and
(iii) detecting expression of said polypeptide,
wherein the reduction of expression in comparison to a control cell not contacted with the potential inhibitor indicates that the potential inhibitor inhibits expression of said polypeptide.

In a sixth aspect the present invention provides a method of identifying an inhibitor of the toxic effect of a polypeptide comprising or consisting of dipeptide repeats, comprising the steps of:
(i) providing a cell comprising a polynucleotide sequence encoding said polypeptide,
(ii) contacting the cell with a potential inhibitor of the toxic effect of said polypeptide, and
(iii) detecting the toxic effect of said polypeptide,
wherein the reduction of the toxic effect in comparison to a control cell not contacted with the potential inhibitor indicates that the potential inhibitor inhibits the toxic effect of said polypeptide.

In a seventh aspect the present invention provides a method of identifying an inhibitor of formation of aggregates comprising a polypeptide comprising or consisting of dipeptide repeats, comprising the steps of:
(i) providing a cell expressing a polynucleotide sequence encoding said polypeptide or a cell free system comprising said polypeptide,
(ii) contacting the cell or the cell free system with a potential inhibitor of formation of aggregates of said polypeptide, and
(iii) detecting formation of aggregates of said polypeptide, wherein the reduction of formation of aggregates in comparison to a control cell or cell free system not contacted with the potential inhibitor indicates that the potential inhibitor inhibits formation of aggregates.

In an eighth aspect the present invention provides an inhibitor of expression of a polypeptide comprising or consisting of dipeptide repeats or an inhibitor of formation of aggregates comprising or consisting of a polypeptide comprising dipeptide repeats or an inhibitor of the toxic effects caused by the expression or the formation of aggregation of the polypeptide comprising or consisting of dipeptide repeats for treating or preventing a disease characterized by an expansion of genomic hexanucleotide repeats.

In a ninth aspect the present invention provides a polypeptide according to the second or third aspect, the ligand according to the fourth aspect, the inhibitor according to the eighth aspect and/or a nucleotide sequence encoding the polypeptide according to the second or third aspect, encoding the ligand according to the fourth aspect or encoding the inhibitor according to the eighth aspect for use in diagnosis, prophylaxis, or treatment of a disease characterized by an expansion of genomic hexanucleotide repeats.

In a tenth aspect the present invention provides a kit of parts for diagnosing, treating or preventing a disease characterized by an expansion of genomic hexanucleotide repeats comprising the polypeptide according to the second or third aspect, the ligand according to the fourth aspect, the inhibitor according to the eighth aspect and/or a nucleotide sequence encoding the polypeptide according to the second or third aspect, encoding the ligand according to the fourth aspect or encoding the inhibitor according to the eighth aspect, and optionally further comprising a container, and/or a data carrier, preferably comprising instructions for one or more of the methods of the first, fifth to seventh aspect.

In an eleventh aspect the present invention provides a pharmaceutical comprising the polypeptide according to the second or third aspect, the ligand according to the fourth aspect, the inhibitor according to the eighth aspect and/or a nucleotide sequence encoding the polypeptide according to the second or third aspect, encoding the ligand according to the fourth aspect or encoding the inhibitor according to the eighth aspect.

In a twelfth aspect the present invention provides a pharmaceutical comprising the polypeptide according to the second or third aspect, the ligand according to the fourth aspect, the inhibitor according to the eighth aspect and/or a nucleotide sequence encoding the polypeptide according to the second or third aspect, encoding the ligand according to the fourth aspect or encoding the inhibitor according to the eighth aspect for use in diagnosis, prophylaxis, or treatment of a disease characterized by an expansion of genomic hexanucleotide repeats.

BRIEF DESCRIPTION OF THE FIGURES

In the following, the content of the figures comprised in this specification is described. In this context, please also refer to the detailed description of the invention above and/or below.

FIG. 2: Summary of findings in FTLD/ALS cases and controls. Summary of the immunohistochemical findings for DPR, p62 and TDP-43 inclusions for all analyzed patients. TDP-43 pathology was examined with phospho-TDP-43 or pan-TDP-43 antibodies. NE, not examined. NA, not available.

FIG. 10: List of 20 selected proteins specifically binding to the GGGGCC-repeat. 20 proteins were selected as specific GGGGCC repeat binding proteins based on the stringent criteria described in Example 9. The Quantitative Value reflects the relative protein amount estimated from the intensity of LC-MS/MS signal derived from the 500 mM elution using Scaffold software. In the presence of non-biotinylated GGGGCC repeat competitor (competition) binding of all proteins is efficiently suppressed. Furthermore, these proteins show at least 2 times more binding to the GGGGCC RNA repeat (GC) compared to AAAACC RNA repeat (AC). Quantitative values shown here were the averages of three independent experiments.

FIG. 11: Identification of antibodies specifically binding to the GGGGCC-repeat. (A) A representative Western Blot analysis showing binding of selected GA-specific antibodies by immunoblotting with purified GST-fusion protein containing the GA-DPR (GA)$_{15}$. Aliquots of proteins were subjected to electrophoresis, and Western blotting was performed using the indicated antibodies (GA 5E9, GA 5F2, GA 1A12). GST-fusion proteins containing GP-, GR, AP-, PR-DPRs were used as control for GA-binding specificity.

Figure 1:
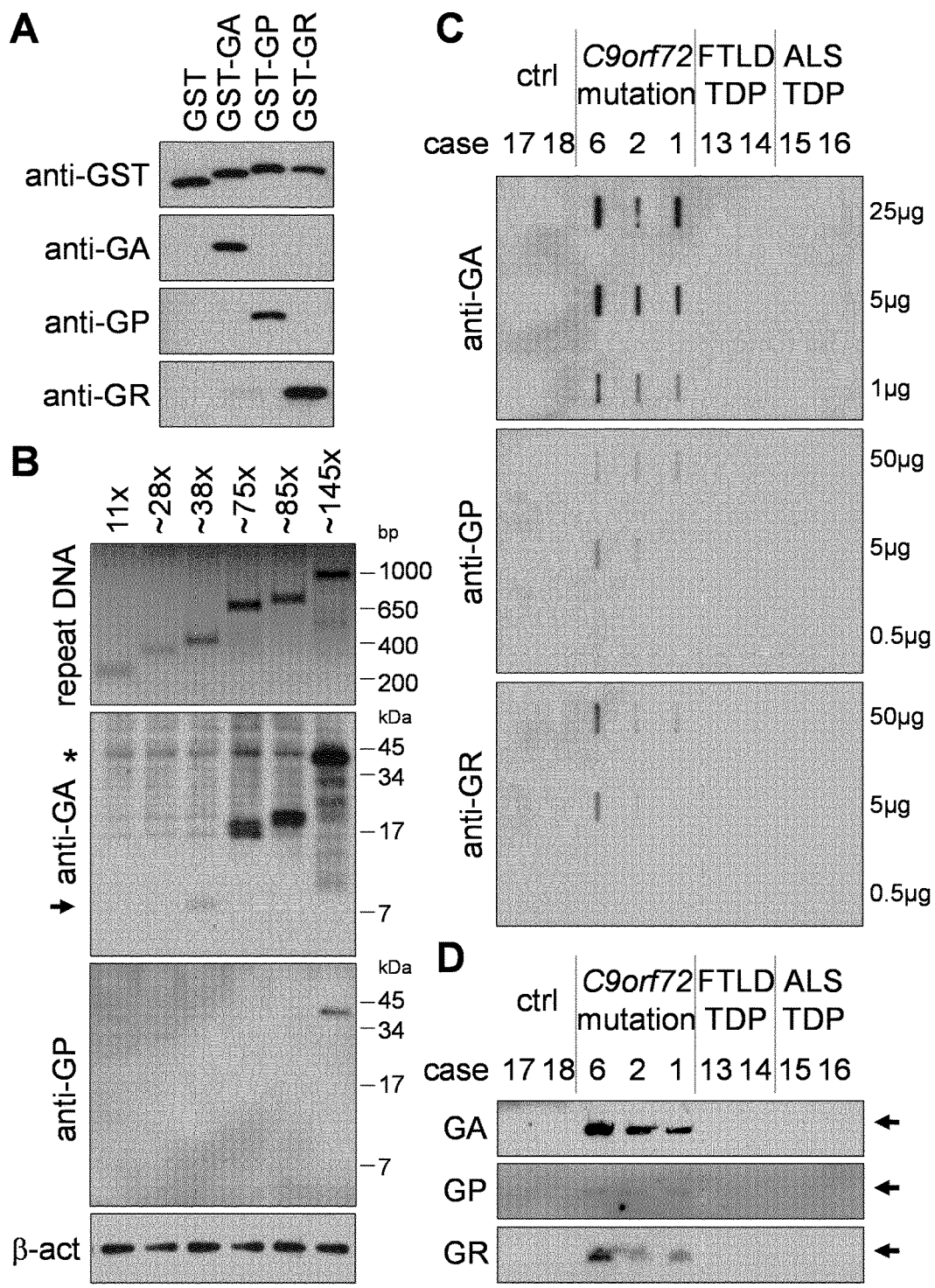
FIG. 1: Extended GGGGCC repeats are translated into aggregating dipeptide-repeat (DPR) proteins. (A) Validation of DPR-specific antibodies by immunoblotting with purified GST-fusion proteins containing $(GA)_{15}$, $(GP)_{15}$ or $(GR)_{15}$. (B) GGGGCC-repeat constructs with indicated repeat length lacking an upstream ATG were transfected into HEK293 cells. Restriction digest to estimate the repeat length of the transfected constructs (upper panel). Immunoblots show length-dependent expression of poly-GA and poly-GP proteins. Poly-GA products were detectable starting from ~38 repeats (arrow). Asterisk indicates nonspecific band. Poly-GR products were not detected (not shown). (C) Filter trap assay from patient cerebellum (see FIG. 2). Triton-X100 insoluble fractions were resuspended in 2% SDS, filtered through cellulose acetate membranes and retained proteins were detected with the indicated antibodies. (D) The SDS-insoluble fraction from (C) was boiled in 4× Lämmli buffer (containing 8% SDS) and analyzed by immunoblotting. Arrows mark top of the gel.

(B) ELISA experiments demonstrating high affinity of the GA-specific antibodies. Antibodies were incubated with increasing amounts of GST-fusion protein $(GA)_{15}$ and absorbance was measured at 450 nm wavelength. GST 2C8 antibody was used as control. To determine the binding specificity of the selected GA antibodies, an ELISA was carried out. Therefore ELISA plates were coated with donkey-anti-mouse antibodies (adsorbed against rat Ig, 100 ng/well) followed by a blocking step (1% BSA in BBST). The pre-coated plates were incubated with mouse anti-GA or anti-GST capture antibodies (100 μl hybridoma supernatant diluted 1/5) and then incubated 1 hour at 37° C. with a dilution series of GST-(GA)15. Bound antigen was detected with rat anti-GST antibody and a secondary donkey anti-rat HRP antibody (adsorbed against mouse Ig 40 ng/well). For quantitative analysis, plates were incubated with the HRP-substrate TMB. The color reaction was stopped with HCl and absorbance was measured at 450 nm.

FIG. 12: Sequences of light chain variable regions and heavy chain variable regions of antibodies GA 1A12, GA 5E9, and GA 5F2.

Herein the sequences of the variable regions of light chains (LCVR, SEQ ID NO: 79) and heavy chains (HCVR) are shown. The sequences of the LCVR are identical, however, the sequences of the HCVR differ in the three different anti-GA antibodies (GA 1A12 (SEQ ID NO: 80), GA 5E9 (SEQ ID NO: 81), GA 5F2 (SEQ ID NO: 82)).

Sequences of the LCVR and HCVR can be determined as is common in the art. For example, data can be obtained as described at http://antibody.bath.ac.uk/align.html. The sequences of the CDRs within the respective heavy and light chains are indicated by capital letters. The intervening framework regions are indicated in small caps.

DETAILED DESCRIPTION OF THE INVENTION

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

Several documents are cited throughout the text of this specification. Each of the documents cited herein (including all patents, patent applications, scientific publications, manufacturer's specifications, instructions etc.), whether supra or infra, is hereby incorporated by reference in its entirety. Nothing herein is to be construed as an admission that the invention is not entitled to antedate such disclosure by virtue of prior invention. Some of the documents cited herein are characterized as being "incorporated by reference". In the event of a conflict between the definitions or teachings of such incorporated references and definitions or teachings recited in the present specification, the text of the present specification takes precedence.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Definitions

In the following, some definitions of terms frequently used in this specification are provided. These terms will, in each instance of their use in the remainder of the specification, have the respectively defined meaning and preferred meanings.

Throughout this specification and the claims which follow, unless the context requires otherwise, the word "comprise", and variations such as "comprises" and "comprising", are to be understood to imply the inclusion of a stated integer or step or group of integers or steps but not the exclusion of any other integer or step or group of integers or steps.

As used in this specification and the appended claims, the singular forms "a", "an", and "the" include plural referents, unless the content clearly dictates otherwise.

As used herein, an "individual" means any mammal, reptile or bird that may benefit from the present invention. Preferably, an individual is selected from the group consisting of laboratory animals (e.g., mouse, rat or rabbit), domestic animals (e.g., guinea pig, rabbit, horse, donkey, cow, sheep, goat, pig, chicken, duck, camel, cat, dog, turtle, tortoise, snake, or lizard), or primates including chimpanzees, bonobos, gorillas and human beings. It is particularly preferred that the "individual" is a human being.

A "patient" is any recipient of health care services. Typically, the patient is ill or injured, or susceptible to illness or injury or at risk of developing a disease and thus, in need of treatment by a physician, physician assistant, advanced practice registered nurse, veterinarian, or other health care provider. As used herein, a patient means any mammal, reptile or bird that may benefit from the invention described herein. Preferably, a "patient" is selected from the group consisting of laboratory animals (e.g., mouse or rat), domestic animals (e.g., guinea pig, rabbit, horse, donkey, cow, sheep, goat, pig, chicken, camel, cat, dog, turtle, tortoise, snake, or lizard), or primates including chimpanzees, bonobos, gorillas and human beings. It is particularly preferred that the "patient" is a human being.

The term "tissue" as used herein refers to an ensemble of cells of the same origin which fulfil a specific function concertedly. Examples of a tissue include but are not limited to nervous tissue, muscle tissue, bone, cartilage, connective tissue, and epithelial tissue. Multiple tissues together form an "organ" to carry out a specific function. Examples of organs include but are not limited to brain, muscle, heart, blood, skeleton, joint, liver, kidney, stomach, and skin.

The term "cell" as used herein may either refer to a prokaryotic (e.g., a bacterial cell) or a eukaryotic cell (e.g., a fungal, plant or animal cell). Multicellular organisms comprise several types of cells differentiated to fulfill different functions in said organism. These include but are not limited to stem cells, embryonic stem cells, cells of the nervous system, blood cells, cells of the immune system, mesenchymal cells, epithelial cells, interstitial cells, metabolism and storage cells, gland cells, extracellular matrix cells, contractile cells, pigment cells, germ cells and tumor cells.

The term "cell" as used herein also refers to those cells being removed from their natural environment, such as isolated primary cells or cell lines of any of the above-named cell types. Typically, cells such as bacterial cells, yeast cells, isolated primary cells or cell lines are used in biotechnological assays. In the context of the present invention isolated primary cells or cell lines are preferably of mammalian origin.

The term "cell-free system" as used herein refers to an in vitro tool widely used to study biological reactions normally occurring in a cell. Cell-free systems aim to reduce the complex interactions found in a whole cell by isolating subcellular fractions, e.g., by ultracentrifugation, to provide molecular machinery that can be used in reactions in the absence of many of the other cellular components. Such subcellular fractions may comprise one or more of the known cellular compartments suitable for the designed assay, including but not limited to the plasma membrane, cytosol, nucleus, nucleoli, nucleular membrane, endoplasmatic reticulum, ribosomes, Golgi apparatus, endosomes, lysosmes, mitochondria, vacuoles, cytoskeletal elements (e.g., actin filaments, microtubuli, intermediate filaments) and the like. In the context of the present invention cell-free systems also encompass cell-free expression systems wherein the transcription and translation as well as protein folding are performed in vitro in absence of any cellular or subcelluar fractions.

The terms "polynucleotide" and "nucleic acid" are used interchangeably herein. Nucleic acid molecules are understood as a polymeric or oligomeric macromolecule made from nucleotide monomers. Nucleotide monomers are composed of a nucleobase, a five-carbon sugar (such as but not limited to ribose or 2'-deoxyribose), and one to three phosphate groups. Typically, a polynucleotide is formed through phosphodiester bonds between the individual nucleotide monomers. In the context of the present invention referred to nucleic acid molecules include but are not limited to ribonucleic acid (RNA), deoxyribonucleic acid (DNA), and mixtures thereof such as RNA-DNA hybrids, as well as cDNA, genomic DNA, recombinant DNA, cRNA and mRNA. A nucleic acid may consist of an entire gene, or a portion thereof. The nucleic acid may also be a microRNA (miRNA) or small interfering RNA (siRNA). MiRNAs are short ribonucleic acid (RNA) molecules, on average only 22 nucleotides long, found in all eukaryotic cells. MircoRNAs (miRNAs) are post-transcriptional regulators that bind to complementary sequences on target messenger RNA transcripts (mRNAs), usually resulting in translational repression and gene silencing. Small interfering RNAs (siRNAs), sometimes known as short interfering RNA or silencing RNA, are short ribonucleic acid (RNA molecules), between 20-25 nucleotides in length. They are involved in the RNA interference (RNAi) pathway, where they interfere with the expression of specific genes. The nucleic acid can also be an artificial nucleic acid. Artificial nucleic acids include polyamide or peptide nucleic acid (PNA), morpholino and locked nucleic acid (LNA), as well as glycol nucleic acid (GNA) and threose nucleic acid (TNA). Each of these is distinguished from naturally-occurring DNA or RNA by changes to the backbone of the molecule.

Suitable methods of detecting nucleic acids such as DNA and/or RNA include e.g., Northern blot analysis, Southern blot analysis, nuclease protection assays (NPA), in situ hybridization (ISH), polymerase chain reaction (PCR for detection of DNA) and reverse transcription-polymerase chain reaction (RT-PCR for detection of RNA).

"Hybridization" can be used in order to detect a certain nucleic acid sequence. A nucleic acid sequence encoding the complementary sequence of the sequence to be detected may be used as a hybridization probe according to standard hybridization techniques. "In situ hybridization" uses a labeled complementary nucleic acid molecule, e.g., a DNA or RNA strand (i.e., a probe) to localize a specific nucleic acid molecule, e.g., a DNA or RNA sequence, in a sample, e.g., in a portion or section of tissue (in situ). Hybridization conditions are known to those skilled in the art and can be found, for example, in Current Protocols in Molecular Biology, John Wiley & Sons, N.Y., 6.3.1-6.3.6, 1991. "Moderate hybridization conditions" are defined as equivalent to hybridization in 2× sodium chloride/sodium citrate (SSC) at 30° C., followed by a wash in 1×SSC, 0.1% SDS at 50° C. "Highly stringent conditions" are defined as equivalent to hybridization in 6× sodium chloride/sodium citrate (SSC) at 45° C., followed by a wash in 0.2×SSC, 0.1% SDS at 65° C.

For the "Northern blotting" procedure, RNA samples may be first separated by size via electrophoresis in an agarose gel under denaturing conditions. The RNA is then transferred to a membrane, crosslinked and hybridized with a labeled probe. Nonisotopic or high specific activity radio labeled probes can be used including random-primed, nick-translated, or PCR-generated DNA probes, in vitro transcribed RNA probes, and oligonucleotides. Additionally, sequences with only partial homology (e.g., cDNA from a different species or genomic DNA fragments that might contain an exon) may be used as probes.

The "Nuclease Protection Assay" (NPA) is an extremely sensitive method for the detection and quantitation of specific mRNAs. The basis of the NPA is solution hybridization of an antisense probe (radio labeled or non-isotopic) to an RNA sample. After hybridization, single-stranded, unhybridized probe and RNA are degraded by nucleases. The remaining protected fragments are separated, e.g., on an acrylamide gel. Solution hybridization is typically more efficient than membrane-based hybridization, and it can accommodate up to 100 μg of sample RNA, compared with the 20-30 μg maximum of blot hybridizations. NPAs are also less sensitive to RNA sample degradation than Northern analysis since cleavage is only detected in the region of overlap with the probe (probes are usually about 100-400 bases in length).

In "RT-PCR", an RNA template is copied into a complementary DNA (cDNA) using a retroviral reverse transcriptase. The cDNA is then amplified exponentially by PCR. Relative quantitative RT-PCR ("qPCR") involves amplifying an internal control simultaneously with the gene of interest. The internal control is used to normalize the samples. Once normalized, direct comparisons of relative abundance of a specific mRNA can be made across the samples. Competitive RT-PCR is used for absolute quantitation. This technique involves designing, synthesizing, and accurately quantitating a competitor RNA that can be distinguished from the endogenous target by a small difference in size or sequence. Known amounts of the competitor RNA are added to experimental samples and RT-PCR is performed. Signals from the endogenous target are compared with signals from the competitor to determine the amount of target present in the sample.

The above methods may include nucleic acid labeling. A series of techniques are known to the skilled person allowing for labeling of DNA, RNA or oligonuleotides. These include for example Nick translational labeling, random primed DNA labeling, PCR labeling of DNA probes, oligonucleotide 3'/5' end labeling, transcriptional labeling of RNA probes, and oligonucleotide tailing.

The term "open reading frame" (ORF) refers to a sequence of nucleotides, that can be translated into amino acids. Typically, such an ORF contains a start codon, a subsequent region usually having a length which is a multiple of 3 nucleotides, but does not contain a stop codon (TAG, TAA, TGA, UAG, UAA, or UGA) in the given reading frame. Typically, ORFs occur naturally or are constructed artificially, i.e., by gene-technological means. An ORF codes for a peptide, polypeptide, or protein where the amino acids into which it can be translated form a peptide-linked chain.

The terms "gene expression" or "expression" are used interchangeably herein and refer to the process by which the genetic information is used to synthesize a functional gene product. Typically, such gene product is a peptide, polypeptide, or protein, or a nucleic acid such as a ribosomal RNA (rRNA), transfer RNA (tRNA) or small nuclear RNA (snRNA). Gene expression includes the steps of transcription, RNA splicing, translation, and post-translational modification. Preferably, the term is used to refer to the synthesis of a peptide, polypeptide or protein. Thus, the term "detection of expression" is preferably used to refer to the detection of expression of a peptide, polypeptide or protein. Such detection can be carried out by art known methods, in particular by using ligands specifically binding to the peptide, polypeptide or protein.

Typically in protein synthesis, a DNA sequence encoding a gene is first transcribed into mRNA from which the introns are removed via RNA splicing and the exons are joined and subsequently translated to produce an amino acid chain, which then folds into a protein.

The term "transcription" refers to the process wherein a particular segment of DNA, typically a gene, is transcribed into RNA by the enzyme RNA polymerase. During transcription, a DNA sequence is read by an RNA polymerase, which produces a complementary, antiparallel RNA strand. As opposed to DNA replication, transcription results in an RNA complement that includes uracil (U) in all instances where thymine (T) would have occurred in a DNA complement. If the gene transcribed encodes a protein, the result of transcription is a pre-messenger RNA (mRNA) or mRNA molecule, which will then be translated into a peptide, polypeptide or protein. Alternatively, the transcribed gene may encode for either non-coding RNA genes (such as microRNA, lincRNA, etc.) or ribosomal RNA (rRNA) or transfer RNA (tRNA), other components of the protein-assembly process, or other ribozymes. "RNA splicing" occurs concurrently or after the transcription process and refers to the process wherein the "introns" comprised in the pre-mRNA are removed and the "exons" are covalently joined.

The term "intron" refers to any nucleotide sequence within a gene which is removed by RNA splicing. In the art, the term intron is typically used to refer to both, the DNA sequence within a gene and the corresponding sequence in the RNA transcript which is removed by RNA splicing. Sequences that are joined together in the final mature RNA after RNA splicing are referred to as "exons". Again the term exon is typically used in the art to refer to both, the DNA sequences within a gene and the corresponding sequences in the RNA transcript which are joined during RNA splicing after removal of the intron.

Ribosomes facilitate the process of "translation" of mRNA into an amino acid chain by inducing the binding of tRNAs with complementary anticodon sequences to that of the mRNA. The tRNAs carry specific amino acids that are chained together into a polypeptide as the mRNA passes through and is "read" by the ribosome. Typically, translation is an AUG-dependent process, wherein an AUG codon of the mRNA (corresponding to an ATG codon of the DNA) is recognized as the translation initiation site resulting in methionine being the first amino acid in the produced amino acid chain. However, AUG-independent translation mechanism also exists, e.g., wherein the methionine tRNA interacts with a codon complementary to only two nucleotides. In viruses AUG-independent translation mechanism includes the use of internal ribosome entry sites (IRES) which structurally mimic the initiator tRNA and manipulate the ribosomes to initiate the translation at a non-AUG site.

The term "RAN-translation" refers specifically to an AUG-independent translation mechanism of nucleotide repeats. In the prior art it has been shown that RAN-translation occurs for exonic RNA comprising trinucleotide, tetranucleotide and pentanucleotide repeats. In the work leading to the present invention, it was surprisingly also shown that intronic RNA transcribed from hexanucleotide repeats present in the genome could be translated by RAN-translation. Polypeptides which were RAN-translated of such nucleotide repeats may (but do not necessarily have to) differ from peptides or polypeptides that were translated in an AUG-dependent manner in that they lack the initial methionine. For instance, RAN-translation may be facilitated in that the presence of said nucleotide repeats promotes the formation of a hairpin structure which subsequently triggers the RAN-translation.

The terms "amino acid chain" and "polypeptide chain" are used synonymously in the context of present invention.

In the context of the present invention, the term "peptide" refers to a short polymer of amino acids linked by peptide bonds. It has the same chemical (peptide) bonds as proteins, but is commonly shorter in length. The shortest peptide is a "dipeptide", consisting of two amino acids joined by a single peptide bond. There can also be a tripeptide, tetrapeptide, pentapeptide, etc. Peptides may also have a length of up to 8, 10, 12, 15, 18 or 19 amino acids. A peptide has an amino end and a carboxyl end, unless it is a cyclic peptide. In the context of the present invention, the term "dipeptide repeat (DPR)" refers to a dipeptide of two amino acids joined by a single peptide bond which is duplicated several times to form a longer peptide or a polypeptide, i.e., a dipeptide repeat may comprise 2, 3, 4, 5, 6, 7, 8, 9, 10, 15, 20, 25, 30, 35, 40, 45, 50, 60, 70, 80, 90, 100, 150, 200, 250, 300, 350, 400, 450, 500, 550, 600, 650, 700, 750, 800, 850, 900, 950, 1000, 1500, 2000, 2500, 3000, 3500, 4000, 4500, 5000, 5500, 6000, 6500, 7000, 7500, 8000, 8500, 9000, 9500, 10000 or more dipeptides joined together by peptide bonds. Preferably, the dipeptide repeats are in the range of 500 to 10.000 more preferably in the range of 700 to 4500. The "dipeptide repeats" are the translation products of hexanucleotide repeats. The meaning of this term is further described below. It requires inter alia that the smallest repeat unit has a length of six nucleotides, e.g., in the nucleotide sequence "CGCGCGCGCGCG" (SEQ ID NO: 83) the smallest repeat unit is "CG" and thus this sequence is a dinucleotide repeat. On the other hand in the nucleotide sequence GGGCCCGGGCCC (SEQ ID NO: 84) the smallest repeat unit is "GGGCCC" and thus this is a hexanucleotide repeat. A hexanucleotide that does not comprise a STOP codon will thus encode a dipeptide and a string of repeats of such hexanucleotides will encode a dipeptide repeat. Due to the degeneration of the genetic code it is possible that a nucleotide sequence that fulfills the criteria of being a hexanucleotide repeat encodes a dipeptide of identical amino acids, e.g., the smallest repeat unit of the nucleotide sequence "GGTGGCGGTGGC" (SEQ ID NO: 85) is "GGTGGC", which encodes Gly-Gly. However, it is preferred that the dipeptide comprises two different amino acids, e.g., (Gly-Ala), (Gly-Pro), (Gly-Arg), (Ala-Pro), (Pro-Arg), Gly-Leu), (Ala-Trp), (Pro-Gly), and (Ala-Gln). Otherwise, i.e., if the amino acids of a dipeptide could be identical, it could not be determined for a six amino acid long peptide that there are three dipeptide repeats but such sequence would be considered by the skilled person to be either a hexapeptide or a sixfold repeat of a monomer. Accordingly, the term "dipeptide repeat (DPR)" refers to a dipeptide of two different amino acids joined by a single peptide bond which is duplicated several times to form a longer peptide or a polypeptide, i.e., a dipeptide repeat may comprise 2, 3, 4, 5, 6, 7, 8, 9, 10, 15, 20, 25, 30, 35, 40, 45, 50, 60, 70, 80, 90, 100, 150, 200, 250, 300, 350, 400, 450, 500, 550, 600, 650, 700, 750, 800, 850, 900, 950, 1000, 1500, 2000, 2500, 3000, 3500, 4000, 4500, 5000, 5500, 6000, 6500, 7000, 7500, 8000, 8500, 9000, 9500, 10000 or more dipeptides joined together by peptide bonds.

The term "polypeptide" refers to a single linear chain of amino acids bonded together by peptide bonds and preferably comprises at least about 20 amino acids. A polypeptide can be one chain of a protein that is composed of more than one chain, or it can be the protein itself if the protein is composed of a single chain.

The term "protein" refers to a molecule comprising one or more polypeptides that resume a secondary and tertiary structure and additionally refers to a protein that is made up of several polypeptides, i.e., several subunits, forming quaternary structures. The protein sometimes has non-peptide groups attached, which can be called prosthetic groups or cofactors.

An "isolated peptide", "isolated polypeptide", or "isolated protein" refers to a peptide, polypeptide or protein which has been removed from its natural environment in a cell such that other cellular material normally nearby is not present anymore. In the context of the present invention, peptides, polypeptides or proteins produced outside their natural cellular environment, e.g., via chemical means or via recombinant means in a non-natural environment, are also considered as isolated peptides, polypeptides or proteins.

Polypeptides or proteins (including protein derivatives, protein variants, protein fragments, protein segments, protein epitopes and protein domains) can be further modified by chemical modification. Hence, a chemically modified polypeptide may comprise chemical groups other than the residues found in the 20 naturally occurring amino acids. Examples of such other chemical groups include without limitation glycosylated amino acids and phosphorylated amino acids. Chemical modifications of a polypeptide may provide advantageous properties as compared to the parent polypeptide, e.g., one or more of enhanced stability, increased biological half-life, or increased water solubility. Chemical modifications include, without limitation: PEGylation and glycosylation of non-glycosylated parent polypeptides. Such chemical modifications applicable to the variants usable in the present invention may occur co- or post-translational.

An "antigenic protein" as referred to in the present application is a polypeptide as defined above which contains at least one epitope. An "antigenic fragment" of an antigenic protein is a partial sequence of said antigenic protein comprising at least one epitope. For immunization purposes only those parts of a protein which elicit an immune response are relevant. Therefore, the nucleic acid construct does not need to encode the full-length antigenic protein as it is found in, e.g., a diseased cell, a cancer cell, or a pathogen. A shortened fragment of such a protein is sufficient as long as its amino acid sequence comprises the epitope or epitopes responsible for the recognition of the antigenic protein by the immune system. The term "antigen" as used herein refers to any molecule or part of a molecule, including but not limited to nucleic acids, amino acids, peptides, polypeptides, proteins, carbohydrates, and lipids, to which a ligand of the invention binds.

The term "epitope" as used herein refers to an antigenic determinant which is part of an antigen that is specifically bound by a ligand of the invention, preferably an antibody or antigen-binding fragment thereof. Epitopes typically consist of chemically active surface groupings of molecules such as amino acids or sugar side chains and usually have specific three-dimensional structural characteristics, as well as specific charge characteristics. The epitope of an antigen may be a conformational epitope or a non-conformational, i.e., linear, epitope. Conformational and non-conformational epitopes are distinguished in that the binding to the former but not the latter is lost in the presence of denaturing solvents. A conformational epitope is composed of discontinuous sections of the antigen's amino acid sequence. These epitopes interact with the ligand based on the 3-D surface features and shape or tertiary structure of the antigen. Most epitopes are conformational. By contrast, linear epitopes interact with the ligand based on their primary structure. A linear epitope is formed by a continuous sequence of amino acids from the antigen. Conformational epitopes preferably comprise between 8 and 20 discontinuous amino acids, preferably between 8 and 15 amino acids. Linear epitopes have a length of between 6 and 20 amino acids, more preferably between 8 and 15 amino acids.

Peptides, polypeptides or proteins may be detected via various methods, including but not limited to a filter trap assay, Western blotting, enzyme-linked immunosorbent assay (ELISA), immunohistochemistry (IHC), immunocytochemistry (ICC), and size exclusion chromatography (SEC).

"Immunostaining", including but not limited to immunohistochemistry (IHC) or immunocytochemistry (ICC), is an antibody-based method to detect a specific protein in a sample. The term immunostaining was originally used to refer to the immunohistochemical staining of tissue sections. Now, however, immunostaining encompasses a broad range of techniques used in histology, cell biology, and molecular biology that utilize antibody-based staining methods. While the first cases of IHC staining used fluorescent dyes, other non-fluorescent methods using enzymes such as peroxidase and alkaline phosphatase are now used more often. These enzymes are capable of catalyzing reactions that give a colored product that is easily detectable by light microscopy. Alternatively, radioactive elements can be used as labels, and the immunoreactions can be visualized by autoradiography. Tissue preparation or fixation is essential for the preservation of cell morphology and tissue architecture. Inappropriate or prolonged fixation may significantly diminish the antibody binding capability. Many antigens can be successfully demonstrated in formalin-fixed paraffin-embedded tissue sections. Optimization of fixation methods and times, pre-treatment with blocking agents, incubating antibodies with high salt, and optimizing post-antibody wash buffers and wash times may be important for obtaining high quality immunostaining.

"Size-exclusion chromatography (SEC)" is a chromatic method allowing for the separation of molecules in solution, e.g., proteins, by their size, and in some cases molecular weight. Typically SEC is applied to large molecules or macromolecular complexes such as polypeptides or proteins. "Gel-filtration chromatography" typically refers to an SEC wherein an aqueous solution is used to transport the sample through the column, whereas "gel permeation chromatography" refers to SEC wherein an organic solvent is used as mobile phase.

The term "filter retention assay" and "filter trap assay" are used simultaneously herein to refer to the analysis of protein aggregates. Purified proteins are filtered through cellulose-acetate filters resulting in big aggregates being retained on the filter. Subsequently these membrane-bound aggregates may be characterized by any means or methods known in the art.

"Western blotting" allows the detection of specific proteins (native or denatured) from extracts made from cells or tissues, before or after any purification steps. Proteins are generally separated by size using gel electrophoresis before being transferred to a synthetic membrane (typically nitrocellulose or PVDF) via dry, semi-dry, or wet blotting methods. The membrane can then be probed using antibodies using methods similar to immunohistochemistry, but without a need for fixation. Detection is typically performed using peroxidase linked antibodies to catalyze a chemiluminescent reaction. Western blotting is a routine molecular biology method that can be used to semi quantitatively or quantitatively compare protein levels between extracts. The size separation prior to blotting allows the protein molecular weight to be gauged as compared with known molecular weight markers. Western blotting is an analytical technique used to detect specific proteins in a given sample of tissue homogenate or extract. It uses gel electrophoresis to separate proteins by the length of the polypeptide (denaturing conditions) or by the 3-D structure of the protein (native/non-denaturing conditions).

The "enzyme-linked immunosorbent assay (ELISA)" is a diagnostic method for quantitatively or semi-quantitatively determining protein concentrations from blood plasma, serum or cell/tissue extracts in a multi-well plate format (usually 96-wells per plate). Broadly, proteins in solution are adsorbed to ELISA plates. Antibodies specifically binding to the protein of interest are used to probe the plate.

"Electron microscopy (EM)" can be used to study the detailed micro architecture of tissues or cells. "Immuno-EM" allows the detection of specific proteins in ultrathin tissue sections. Antibodies labeled with heavy metal particles (e.g., gold) can be directly visualized using transmission electron microscopy.

A "marker", "tag", or "label" is any kind of substance which is able to indicate the presence of another substance or complex of substances. The marker can be a substance that is linked to or introduced in the substance to be detected. Detectable markers are used in molecular biology and biotechnology to detect, e.g., a protein, a product of an enzymatic reaction, a second messenger, DNA, interactions of molecules, etc. Examples of suitable markers or labels include a fluorophore, a chromophore, a radiolabel, a metal colloid, an enzyme, or a chemiluminescent or bioluminescent molecule. Examples of fluorophores include various forms of green fluorescent protein (GFP) such as EnGFP, RFP, CYP, BFP, YFP, dsRed, etc., phycobiliproteins (allophycocyanin, phycocyanin, phycoerythrin and phycoerythrocyanin), fluorescein (fluorescein isothiocyanate, FITC), rhodamine (tetramethyl rhodamine isothiocyanate, TRITC), and cyanine dyes (such as C2, Cy3 Cy5, and Cy7). Examples of radiolabels include $^{3}H$, $^{14}C$, $^{32}P$, $^{33}P$, $^{35}S$, $^{99m}Tc$ and $^{125}I$. Examples of enzymes include luciferase, beta-galactosidase, horseradish peroxidase, alkaline phosphatase, glucose oxidase, and urease.

As used herein, the term "selection marker" refers to a reporter gene which conveys a certain trait to a cell or organism which allows such cell or organism to survive in an environment in which it would not survive without said reporter gene. Accordingly, the expression of a selection marker allows for the artificial selection of cells or organisms whose genome comprises said reporter gene. Selection markers include but are not limited to auxotrophic marker genes and resistance marker genes conferring resistance to a toxin or an antibiotic. The terms "selection marker", "reporter gene", and "marker gene" are used interchangeably herein. Selection markers may be auxotrophic marker genes or resistance marker genes conferring resistance to a toxin or an antibiotic. The "auxotrophy marker gene" is understood as a gene which enables growth of such auxotrophic cells or organisms under selective culture conditions by encoding a molecule required for the synthesis of a product necessary for the survival of an auxotrophic prokaryote on a selective medium used for cell culturing. Any marker gene which is capable of complementing the corresponding gene which is nonfunctional in an auxotrophic cell or organism may be useful in the context of this invention. As used herein, the terms "resistance marker genes conferring resistance to a toxin and/or an antibiotic", or variations thereof such as "toxin-resistance marker genes" or "antibiotic-resistance genes", refer to reporter genes which encode an enzyme that functionally inactivates a toxin or an antibiotic. The functional inactivation of a toxin or antibiotic may be achieved by expressing a marker gene which carries mutation(s) rendering the respective gene product insensitive to a toxin or antibiotic. Alternatively, the functional inactivation of a toxin or antibiotic may be achieved by expressing a marker gene which inhibits the toxin or antibiotic e.g., by interacting or binding to it. The functional inactivation of a toxin or antibiotic may also be achieved by expressing a marker gene which counteracts the effects of the toxin or antibiotic. Antibiotic compounds include but are not limited to tetracyclines, sulfonamides, penicillins, cephalosporins, ansamycins, carbapenems, macrolides, quinolones, aminonucleoside, aminoglycosides, peptides, glycopeptides, and lipopeptides. Exemplified, hygromycin B, neomycin, kanamycin, gentamicin, and G418 (also known as Geneticin) are aminoglycoside antibiotics which are similar in structure. In general, neomycin and kanamycin are used for prokaryotes, while G418 is needed for eukaryotes.

Different types of chemical labels or tags can be conjugated to secondary or primary antibodies and other molecules to facilitate their visualization (i.e., detection and measurement) by various methods. Radioisotopes were used extensively in the past, but they are expensive, have a short shelf-life, offer no improvement in signal to noise ratio and require special handling and disposal. Enzymes and fluorophores have largely replaced radioactive isotopes as detectable tags for assays. A number of advancements in reagents and instrumentation make these newer technologies more versatile and powerful. Enzymatic tags such as horseradish peroxidase (HRP) are most commonly used for blotting, immunoassays and immunohistochemistry methods. Fluorescent tags are used predominantly for cellular imaging, nucleic acid amplification and sequencing and microarrays; however, fluorescence technology is developing rapidly for application in all types of assays.

The term "expression level" refers to the amount of gene product (e.g., DPR) present in the body or a sample at a certain point of time. The expression level can, e.g., be measured/quantified/detected by means of the amounts of the protein or of the mRNA encoding the protein. For example the expression level can be quantified by normalizing the amount of a gene product of interest (e.g., DPR) present in a sample with the total amount of a gene product of the same category (total protein or mRNA) in the same sample or in a reference sample (e.g., a sample taken at the same time from the same individual or a part of identical size (weight, volume) of the same sample) or by identifying the amount of gene product of interest per defined sample size (weight, volume, etc.). The expression level can be measured/quantified/detected by means of any method as known in the art, e.g., methods for the direct detection and quantification of the gene product of interest (such as mass spectrometry) or methods for the indirect detection and measurement of the gene product of interest that usually work via binding of the gene product of interest with one or more different molecules or detection means (e.g., primer(s), probes, antibodies, scaffold-proteins) specific for the gene product of interest (e.g., DPR). Preferably, the expression level is determined on the basis of the protein rather than on the basis of the mRNA.

The term "toxicity" as used herein refers to the degree to which a compound/substance can damage an organism or a substructure of the organism, such as a cell (cytotoxicity), tissue or an organ. Accordingly, the term "toxic effect" refers to the damaging effect a compound/substance has on an organism, organ, tissue or cell. A compound may exhibit a toxic effect in that it damages the function and/or structure of an organism, organ, tissue or cell, which may result in an altered function or a loss of function of certain elements or parts of the organism, organ, tissue or cell, or may even result in the death of said organism, organ, tissue or cell. The term "toxic compound" thus refers to a substance, e.g., a nucleic acid, a peptide, polypeptide or protein, or a chemical substance or compound, which exhibits a toxic effect on the organism, organ, tissue or cell.

The toxicity or the toxic effect of a compound may be measured using one of various viability assays known in the art including but not limited to formazan-based assays (MTT/XTT), Lactate dehydrogenase (LDH) assay, ATP test, Calcein AM, Clonogenic assay, Ethidium homodimer assay, evans blue, Fluorescein diacetate hydrolysis/Propidium iodide staining (FDA/PI staining), Flow cytometry, TUNEL assay, with green fluorescent protein (GFP), methyl violet, propidium iodide, trypan blue, or resazurin. Further, DNA stainings may be used to differentiate between necrotic, apoptotic and normal cells.

The terms "disease" and "disorder" are used interchangeably herein, referring to an abnormal condition, especially an abnormal medical condition such as an illness or injury, wherein a cell, a tissue, an organ, or an individual is not able to efficiently fulfill its function anymore. Typically, but not necessarily, a disease is associated with specific symptoms or signs indicating the presence of such disease. The presence of such symptoms or signs may thus be indicative for a cell, a tissue, an organ, or an individual suffering from a disease. An alteration of these symptoms or signs may be indicative for the progression of such a disease. A progression of a disease is typically characterised by an increase or decrease of such symptoms or signs which may indicate a "worsening" or "bettering" of the disease. The "worsening" of a disease is characterised by a decreasing ability of a cell, tissue, organ or individual/patient to fulfill its function efficiently, whereas the "bettering" of a disease is typically characterised by an increase in the ability of a cell, tissue, an organ or an individual/patient to fulfill its function efficiently. A cell, a tissue, an organ or an individual being "susceptible" to a disease is in a healthy state but especially vulnerable to the emergence of a disease, due to, e.g., genetic predisposition, lack of vaccination, poorly developed or immature immunity, poor nutritional status, or the like. The outbreak of the disease may still be prevented by prophylaxis or pre-cautionary treatment. A cell, a tissue, an organ or an individual may be "suspected of having" a disease wherein said cell, tissue, organ or individual typically shows early or weak signs or symptoms of such disease. In such case, the onset of the disease may still be prevented or its progression may be reduced or prevented by treatment.

As used herein, "detect", "detecting", or "detection" of a disease or disorder refers to establishing the presence or absence of a disease in a patient. For instance, a moiety used in the detection of a disease is able to identify the presence or absence of an indicator of a disease in a sample or in an individual or patient. For instance, a disease may be detected by means of a ligand or a tagged ligand interacting with, i.e., binding to or forming a complex with, a disease specific nucleic acid or peptide, polypeptide or protein. A disease may also be detected by means of an inhibitor blocking the mechanism of action underlying the disease and thus altering the symptoms such that the underlying disease may be identified.

As used herein, "treat", "treating", "treatment" or "therapy" of a disease or disorder means accomplishing one or more of the following: (a) reducing the severity of the disorder; (b) limiting or preventing development of symptoms characteristic of the disorder(s) being treated; (c) inhibiting worsening of symptoms characteristic of the disorder(s) being treated; (d) limiting or preventing recurrence of the disorder(s) in an individual that has previously had the disorder(s); and (e) limiting or preventing recurrence of symptoms in individuals that were previously symptomatic for the disorder(s). Accordingly, a therapy treats a disease or disorder or the symptoms of a disease or disorder by accomplishing one or more of the above-named effects (a)-(e). For instance, a disease may be treated by means of inhibiting/blocking the mechanism of action underlying the disease, e.g., via compounds that inhibit the expression of disease specific polypeptides/proteins, or by inhibiting further processes said polypeptide/protein is involved in. A disease may also be treated by activating the patient's immune system, e.g., via active immunization, or by supporting the patient's immune system, e.g., via passive immunization.

As used herein, "prevent", "preventing", "prevention", or "prophylaxis" of a disease or disorder means preventing that such disease or disorder occurs in a patient. Accordingly, a moiety having a prophylactic effect prevents the onset of a disease or disorder in a patient. For instance, a disease or disorder may be prevented by immunizing, e.g., actively or passively immunizing, a healthy individual such that the onset of disease is avoided. Alternatively, a disease or disorder may be prevented through ligands or inhibitors undermining the function of disease related molecules or processes, e.g., via ligands or inhibitors that block the expression of disease specific polypeptide/proteins or by inhibiting further processes said polypeptides/protein is involved in.

The term "immunization" refers to the process of activating, strengthening or boosting the immune system of an individual against an agent which typically causes or induces a disease or disorder. Hence, by immunizing a healthy individual against said agent, the onset of a disease or disorder may be prevented. Immunizing a patient suffering from a disease or disorder may treat said disease or disorder or may prevent the further progression of said disease. Immunization may be achieved through various techniques; most commonly immunization is achieved through vaccination of the healthy individual or the patient suffering from a disease or disorder.

The term "passive immunization" refers to the process wherein pre-synthesized elements of the immune system are transferred to an individual/patient such that the body does not need to produce these elements itself. Passive immunization aims at the treatment of a disease or the prevention of the progression of a disease, in particular in cases where the patient is not able to combat such disease or disorder due to an inefficient immune system (e.g., deficient immune system, or unrecognizable immunogen, e.g., of a tumour). For instance, antibodies (e.g., animal or humanized antibodies produced in vitro by cell culture) directed against a disease-specific immunogen, or nucleic acids encoding said antibody and allowing for its expression, are means of passive immunization. The term "active immunization" refers to the immunization via the introduction of a foreign molecule (immunogen) into the body, which causes the body itself to generate an immune response against the immunogen. Active immunization aims at the prophylaxis of a disease or the prevention of the progression of a disease, as the immune system of an individual is primed/activated/strengthened to react against said immunogen, resulting in a more efficient or faster immune response to the immunogen. The principle underlying active immunization is the generation of an immunological "memory". Challenging an individual's immune system with, e.g., a vaccine comprising a disease specific immunogen induces the formation and/or propagation of immune cells which specifically recognize the immunogen comprised by the vaccine. At least a part of said immune cells remain viable for a period of time which can extend to 10, 20 or 30 years after vaccination. If the individual's immune system encounters the immunogen again within the aforementioned period of time, the immune cells generated by vaccination are reactivated and enhance the immune response against the immunogen as compared to the immune response of an individual which has not been challenged with the vaccine and encounters said immunogen for the first time. In many cases, a single administration of a vaccine is not sufficient to generate the number of long-lasting immune cells which is required for effective protection against said disease or disorder. Consequently, repeated challenge with a biological preparation specific for a specific disease is required in order to establish lasting and protective immunity against said disease or to cure a given disease. An administration regimen comprising the repeated administration of a vaccine directed against the same disease is referred to in the present application as a "prime-boost vaccination regimen". A prime-boost vaccination regimen may involve at least two administrations of a vaccine or vaccine composition directed against a specific pathogen, group of pathogens or disease. The first administration of the vaccine is referred to as "priming" and any subsequent administration of the same vaccine or a vaccine directed against the same pathogen as the first vaccine is referred to as "boosting". The period of time between prime and boost is, preferably, 1 week, 2 weeks, 4 weeks, 6 weeks or 8 weeks. More preferably, it is 4 weeks or 8 weeks. If more than one boost is performed, the subsequent boost is, preferably, administered 1 week, 2 weeks, 4 weeks, 6 weeks or 8 weeks after the preceding boost. More preferably, the interval between any two boosts is 4 weeks or 8 weeks. Prime-boost vaccination regimens may be homologous or heterologous. In homologous prime-boost regimens both the priming and the at least one boosting are performed using the same means of administration of the antigenic protein or antigenic fragment thereof, i.e., priming and boosting are performed using a polypeptide or priming and boosting are performed using a nucleic acid construct comprised by the same vector. A heterologous prime-boosting regimen involves the use of different means for priming and for boosting the immune response.

Two or more antigenic proteins or antigenic fragments thereof are "immunologically identical" if they are recognized by the same antibody, T-cell or B-cell. The recognition of two or more immunogenic polypeptides by the same antibody, T-cell or B-cell is also known as "cross reactivity" of said antibody, T-cell or B-cell. Preferably, the recognition of two or more immunologically identical polypeptides by the same antibody, T-cell or B-cell is due to the presence of identical or similar epitopes in all polypeptides. Similar epitopes share enough structural and/or charge characteristics to be bound by the Fab region of the same antibody or B-cell receptor or by the V region of the same T-cell receptor. The binding characteristics of an antibody, T-cell receptor or B-cell receptor are, preferably, defined by the binding affinity of the receptor to the epitope in question. Two immunogenic polypeptides are "immunologically identical" as understood by the present application if the affinity constant of the polypeptide with the lower affinity constant is at least 30%, at least 40%, at least 50%, at least 60%, at least 70%, at least 80%, at least 90%, at least 95% or at least 98% of the affinity constant of the polypeptide with the higher affinity constant. Methods for determining the binding affinity of a polypeptide to a receptor, such as equilibrium dialysis or enzyme linked immunosorbent assay (ELISA), are well known in the art. Preferably, two or more "immunologically identical" polypeptides comprise at least one identical epitope. The strongest vaccination effects can usually be obtained, if the immunogenic polypeptides comprise identical epitopes or if they have an identical amino acid sequence. The term "vaccine" refers to a biological preparation, typically a pharmaceutical, which improves immunity to a specific disease. Said preparation may comprise one or more disease specific immunogens suitable for eliciting an immune response. In the context of the present invention, said compound may be a polypeptide which is substantially identical or immunologically identical to a polypeptide as specified below comprising the specified dipeptide repeat (DPR). Alternatively, the vaccine may comprise a nucleic acid construct which encodes an immunogenic polypeptide which is substantially identical or immunologically identical to a polypeptide comprising the specified dipeptide repeat. In the latter case, it is preferred that the polypeptide is expressed in the individual treated with the vaccine. In the context of the present invention said nucleic acid construct may be a vector.

As used herein, the term "vector" refers to a protein or a polynucleotide or a mixture thereof which is capable of being introduced or of introducing the proteins and/or nucleic acids comprised therein into a cell. Moreover, the term "vector" refers to at least one polynucleotide formulated with a preparation of liposomes or lipid nanoparticles which is capable of transfecting a cell with the at least one polynucleotide as described, e.g., by Geall et al., 2012. In addition to the polynucleotide encoding the gene of interest, additional polynucleotides and/or polypeptides may be introduced into the cell. The addition of further polynucleotides and/or polypeptides is especially preferred if said additional polynucleotides and/or polypeptides are required to introduce the nucleic acid construct into the cell or if the introduction of additional polynucleotides and/or polypeptides increases the expression of the immunogenic polypeptide encoded by the nucleic acid construct of the present invention.

In the context of the present invention it is preferred that the genes of interest encoded by the introduced polynucleotide are expressed within the cell upon introduction of the vector or vectors. Examples of suitable vectors include but are not limited to plasmids, cosmids, phages, viruses or artificial chromosomes.

Examples of a disease include but are not limited to neurological disorders, inflammatory diseases, infectious diseases, cutaneous conditions, endocrine diseases, intestinal diseases, genetic disorders, autoimmune diseases, traumatic diseases, joint diseases, and various types of cancer.

"Neurological disorders" refers to any disorder of the nervous system wherein structural, biochemical or electrical abnormalities occur in the brain, the spinal cord or other nerves which affect a range of symptoms, including but not limited to paralysis, muscle weakness, poor coordination, loss of sensation, seizures, confusion, pain and altered levels of consciousness. Examples of neurological disorders include but are not limited to damage of the brain or individual parts of the brain (e.g., damage of the prefrontal cortex, frontal lobe, parietal lobe, temporal lobe, occipital lobe, cerebellum, hippocampus, brain stem, limbic system), dysfunction of the brain or individual parts of the brain (e.g., aphasia, dysarthria, apraxia, agnosia, amnesia, ataxia), or inflammation of the brain (e.g., encephalitis, viral encephalitis, cavernous sinus thrombosis, brain abscess, amoebic). "Neurodegenerative diseases" such as Alzheimer's disease, Parkinson's disease, Huntington's disease, Amyotrophic lateral sclerosis (ALS), frontotemporal dementia (FTD), which is also called frontotemporal lobar degeneration (FTLD), amyotrophic lateral sclerosis-frontotemporal dementia (ALS-FTD, also called ALS-FTLD), and spinocerebellar ataxia are further examples of neurological disorders. The clinical and pathological terms FTD and FTLD (and ALS-FTD and ALS-FTLD) are used synonymously in this application. Neurological disorders also include spinal cord disorders (e.g., syringomyelia, syringobulbia, Morvan's syndrome, vascular myelopathy, Foix-Alajouanine syndrome, spinal cord compression) and spinal cord inflammation (e.g., myelitis, poliomyelitis, demyelinating disease, transverse myelitis, tropical spastic paraparesis, epidural abscess), central and/or peripheral neuropathy, cranial nerve disorders (e.g., trigeminal neuralgia), movement disorders of the central and/or peripheral nervous system (e.g., Parkinson's disease, ALS, Tourette's Syndrome, multiple sclerosis), sleep disorders (e.g., insomnia, hypersomnia, sleep apnea, narcolepsy, cataplexy, Kleine-Levin syndrome, circadian rhythm sleep disorder, advanced sleep phase disorder, delayed sleep phase disorder), headache (e.g., migraine, cluster, tension), neuropsychiatric illnesses, delirium, dementia (e.g., Alzheimer's disease, vascular dementia, FTD, semantic dementia and dementia with Lewy bodies), stroke (e.g., MCA, ACA, PCA, Foville's, Millard-Gubler, Lateral medullary, Weber's, Lacunar stroke), tumors (e.g., gliomas, meningiomas, pituitary adenomas, nerve sheath tumors), complex regional pain syndrome, and motor neuron diseases (MND) (e.g., ALS, primary lateral sclerosis (PLS), progressive muscular atrophy (PMA), progressive bulbar palsy (PBP), pseudobulbar palsy).

"Symptoms" of a disease are implications of the disease noticeable by a cell, tissue, organ or individual having such disease and include but are not limited to pain, weakness, tenderness, strain, stiffness, and spasms of the cell, tissue, an organ or an individual. "Signs" or "signals" of a disease include but are not limited to the change or alteration such as the presence, absence, increase or elevation, decrease or decline of specific indicators such as biomarkers or molecular markers, or the development, presence, or worsening of symptoms.

The terms "indicator" or "biomarker" are used interchangeably herein. In the context of the present invention, an "indicator" can be defined as a substance within a biological system that is used as an indicator of a biological state of said system. In the art, the term "biomarker" is sometimes also applied to means for the detection of said endogenous substances (e.g., antibodies, nucleic acid probes, imaging systems). In the context of present invention, however, the term "biomarker" shall be only applied to the substance, not the detection means. Thus, biomarkers can be any kind of molecule present in a living organism, such as a nucleic acid (DNA, mRNA, miRNA, rRNA, etc.), a protein (cell surface receptor, cytosolic protein, etc.), a metabolite or hormone (blood sugar, insulin, estrogen, etc.), a molecule characteristic of a certain modification of another molecule (e.g., sugar moieties or phosphoryl residues on proteins, methyl-residues on genomic DNA, expansion of nucleotide repeats) or a substance that has been internalized by the organism or a metabolite of such a substance. Accordingly, a disease or disorder may be characterized by the presence or absence, increase or decrease of such an indicator. Said indicator of a disease may or may not cause the disease.

Indicators of the presence and/or progression of a disease include "genetic markers" such as nucleotide repeat, VNTRs (variable number tandem repeat; e.g., STR (Short tandem repeat), AFLP (amplified fragment length polymorphism), SSR (Simple sequence repeat), MLVA, SSLP (Simple sequence length polymorphism), RFLP (restriction fragment length polymorphism), RAPD (random amplification of polymorphic DNA), SNP (single nucleotide polymorphism), SFP (single feature polymorphism), DArT (diversity arrays technology), and RAD markers (restriction site associated DNA markers).

Figure 8:
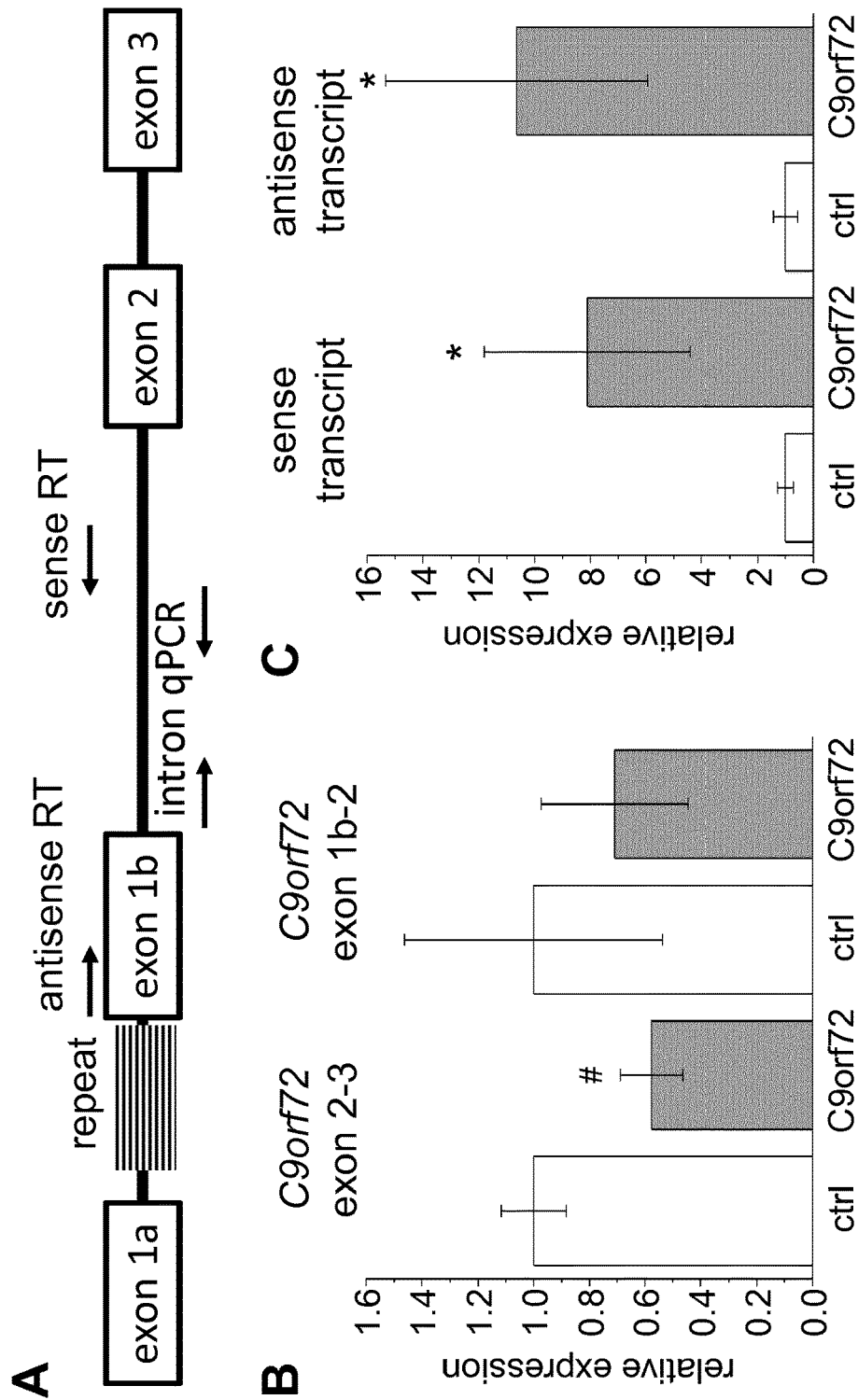
FIG. 8: Differential regulation of C9orf72 transcripts in mutation carriers. (A) Genomic structure of C9orf72 (drawn not to scale). (B) qPCR analysis shows decreased expression of spliced mature C9orf72 mRNA in cerebellum of C9orf72 mutation cases. Primers from exon 2 to 3 detect all C9orf72 isoforms. Primers from exon 1b to 2 detect alternative transcripts lacking the repeat expansion. (C) Strongly increased expression of sense and antisense transcripts containing C9orf72 intron 1. Primers used for strand-specific reverse transcription and qPCR are depicted in (A). Data are mean+/−SEM. * denotes p<0.05, # denotes p<0.058 (Student's t-test). Cerebellum from N=3 C9orf72 patients and N=6 controls including healthy individuals and FTLD/ALS patients without C9orf72 mutation (as in FIGS. 1C-D).

The term "nucleotide repeat" refers to a location in the genome wherein a short nucleotide sequence forms repeating sequences of 2, 3, 4, 5, or 6 nucleotides, i.e., dinucleotides, trinucleotides, tetranucleotides, pentanucleotides, and hexanucleotides. In a healthy state the number of repetitions of the repeat may vary between 1 and 50, i.e., 1, 2, 3, 4, 5, 6, 7, 8, 9, 10, 15, 20, 25, 30, 35, 40, 45, 50. However, in a diseased state these repeats may be expanded to be repeated far more often than in a healthy state, e.g., they may be expanded 30 to 40 times, leading to several hundred repetitions of the repeat, i.e., 50, 60, 70, 80, 90, 100, 110, 120, 130, 140, 150, 160, 170, 180, 190, 200, 250, 300, 350, 400, 450, 500, 550, 600, 650, 700, 750, 800, 850, 900, 950, 1,000, 1,500, 2,000, 2,500, 3,000, 3,500, 4,000, 4,500, 5,000, 5,500, 6,000, 6,500, 7,000, 7,500, 8,000, 8,500, 9,000, 9,500, or 10,000, or even more repetitions. Accordingly, the expansion level of dinucleotides, trinucleotides, tetranucleotides, pentanucleotides, or hexanucleotides may be an indicator (and/or the cause) of a disease such as a neurological disease, in particular a neurogenerative disease. Exemplified, the expansion of trinucleotide repeats $(CAG)_n$ and of the reverse complement $(CTG)_n$ in the complementary strand is associated with Huntington's disease, the expansion of pentanucleotide repeats ((ATTCT)$_n$ and of the reverse complement (AGAAT)$_n$ in the complementary strand is associated with spinocerebellar ataxia SCA10, whilst the expansion of hexanucleotides (GGGGCC)$_n$ and of the reverse complement (CCCCGG)$_n$ in the complementary strand is associated with ALS, FTD, and FTD-ALS and the expansion of the hexanucleotides ((GGCCTG)$_n$ and of the reverse complement (CAGGCC)$_n$ in the complementary strand is associated with spinocerebellar ataxia SCA36. In principle, nucleotide repeats may be present in the exon or intron of a gene and may or may not be transcribed and may or may not be translated into a peptide or polypeptide.

transcripts (FIG. 8C). Thus 6 reading frames exist, but two result in identical DPRs, namely poly-(Gly-Pro) DPR. Accordingly, the five different possible DPRs are the following: poly-(Gly-Ala), poly-(Gly-Pro), poly-(Gly-Arg), poly-(Ala-Pro) and poly-(Pro-Arg). In particular the poly-GA, poly-GP and poly-AP polypeptides are highly hydrophobic and form aggregates in an intracellular environment.

The genomic sequence of the region surrounding the hexanucleotide repeat of the C9orf72 gene reads as follows in the reference sequence from NCBI (SEQ ID NO: 1):

```
acgtaacctacggtgtcccgctaggaaagagaggtgcgtcaaacagcgacaagttccgcccacgtaaaagatgacgcttg gtgtgtcagccgtccctgctgcccggttgcttctcttttggggcggggtctagcaagagcaggtgtgggtttaggaggt gtgtgttttgttttcccaccctctctccccactacttgctctcacagtactcgctgagggtgaacaagaaaagacctg ataaagattaaccagaagaaaacaaggagggaaacaaccgcagcctgtagcaagctctggaactcaggagtcgcgcgcta

[GGGGCC]$_n$ggggcgtggtcgggcgggcccggggcgggcccggggcggggctgcggttgcggtgcctgcgccgcggc ggcggaggcgcaggcggtggcgagtgggtgagtgaggaggcggcatcctggcgggtggctgtttggggttcggctgccgg gaagaggcgcgggtagaagcgggggctctcctcagagctcgacgcattttttactttccctctcatttctctgaccgaagc tgggtgtcgggctttcgcctctagcgactggtggaattgcctgcatccgggcccgggcttcccggcggcggcggcggcg gcggcggcgcagggacaagggatgggatctggcctcttccttgctttcccgccctcagtacccgagctgtctccttccc ggggacccgctgggagcgctgccgctgcgggctcgagaaaagggagcctcgggtactgagaggcctcgcctgggggaagg ccggagggtgggcggcgcgcggcttctgcggaccaagtcggggttcgctaggaacccgagacggtccctgccggcgagga gatcatgcggg,
```

The neurogenerative diseases ALS, FTD and ALS-FTD are characterized in that the hexanucleotide (GGGGCC)$_n$ repeats located within intron I of the C9orf72 gene are expanded. In a healthy state the number "n" of the GGGGCC-repeats may vary between 1 and 19, i.e., 1, 2, 3, 4, 5, 6, 7, 8, 9, 10, 15, and 19. In a diseased state the number "n" of these repeats may be expanded to be repeated far more often than in a healthy state, e.g., typically they may be expanded much more than 30 to 40 times. However, some patients may already show symptoms starting from 20 repeats. Thus, in a diseased state the expansion of the hexanucleotide repeats may lead to several hundred repetitions of the hexanucleotide repeat, i.e., 20, 25, 30, 35, 40, 45, 50, 60, 70, 80, 90, 100, 110, 120, 130, 140, 150, 160, 170, 180, 190, 200, 250, 300, 350, 400, 450, 500, 550, 600, 650, 700, 750, 800, 850, 900, 950, 1,000, 2,000, 3,000, 4,000, 5,000, 6,000, 7,000, 8,000, 9,000, and 10,000 repeats, or more. The exact number of repeats cannot be determined with current sequencing techniques. Transcription of the genomic GGGGCC-repeats and of the GGCCCC-repeats in the complementary DNA strand (also termed antisense strand) leads to RNA transcription products which comprise either GGGGCC- or GGCCCC-repeats with the above indicated numbers. Surprisingly, translation of these transcripts is initiated from non-ATG codons. The sense transcript is translated in all three reading frames (poly-(Gly-Ala), poly-(Gly-Pro) and poly-(Gly-Arg)). Using strand-specific reverse transcription we detected both sense and antisense wherein "n" has the above outlined preferred and most preferred meanings.

The neurogenerative disease spinocerebellar ataxia SCA36 is characterized in that the hexanucleotide (GGC-CTG)$_n$ repeats located within the intron 1 region of the NOP56 gene are expanded. In a healthy state the number "n" of the GGGGCC-repeats may vary between 1 and 15, i.e., 1, 2, 3, 4, 5, 6, 7, 8, 9, 10, and 15. However, in a diseased state the number "n" of these repeats may be expanded to be repeated far more often than in a healthy state, e.g., typically they may be expanded 30 to 40, leading to several hundred repetitions of the repeat, i.e., 20, 25, 30, 35, 40, 45, 50, 60, 70, 80, 90, 100, 110, 120, 130, 140, 150, 160, 170, 180, 190, 200, 250, 300, 350, 400, 450, 500, 550, 600, 650, 700, 750, 800, 850, 900, 950, 1000, 2000, 3000, 4000, 5000, 6000, 7000, 8000, 9000, and 10000 repeats. Transcription of the genomic GGCCTG-repeats and of the CAGGCC-repeats in the complementary DNA strand leads to RNA transcription products which comprise either GGCCUG- or CAGGCC-repeats. Translation of the sense and antisense transcript strand in all three reading frames results in six different dipeptide-repeat (DPR) polypeptides: poly-(Gly-Leu), poly-(Ala-Trp), poly-(Pro-Gly), poly-(Ala-Gln), poly-(Gly-Pro), and poly-(Pro-Arg), which may also form aggregates in an intracellular environment.

The genomic sequence of the region surrounding the hexanucleotide repeat of the NOP56 gene reads as follows (SEQ ID NO: 2):

```
ggctcgtccccgagtaggggacgggaacgcctgggtcccggggacgtggggcgcagggtctggggcccgaggccac ggacgaagcgggaagccggctaggcagcggtctctgtctgggatggacgccgcgcccacgcggacctcccgcccc
```

-continued

```
gacttcacccagctctgctgcccgtaactcatatgacaagaacatcaggaaccggactattaccccgaaagggcct tcccaagtcgtttcgccgcctgcagtgcccgaccgggggcgcgcgtccccggcaaccacgcccgcccgcgcagct gcagaggccggaaaaggcccgctcgcccgcgctcggcaccacccagcccgcgctccgggcgataccaccctgggcg gcccctccaaaggccggagatggtgtcgtccccggcctccgattggtcgggggggcggggcgtggcctctggagc ctggttccgcgcgccggagcgcgctagccgcattgcgagccgaacccgggagctggcgccatggtgaggagtggtt gcggggcgcgggcgacgcgacggtgggggtttcggcctgcgttcgggccgcagacag[GGCCTG]ncgcctgcgcc tgcgcctgccctgggaacgggttccggcagacgctgaggttgcgttgacgctcgcgcccggctcccgttccaggt gctgttgcacgtgctgtttgagcacgcggtcggctacgcgctgctggcgctgaaggaagtggaggagatcagtctg ctgcagccgcaggtgggtgagatccgtgggctcctttggcggccccgcagaccctcatcgcgcgggtcccagcatg cacagcgcgctcccacgtggccggccgagcggttcggggcgggggacgggcctggaaagctctagatccggggt ctttaccttgacccatgggtagaatcgctctagcaattagaaataagcctcccggacgccgcccccgaacgattaa agcagaagctgggatgtgggggcccaggtatcagcatattttaagagcttccaaggctgagaaccgctgcttgactg cgccgcagaggcaggagggagggaaggaaaccacttagcctctttctcccccaggtggaggagtctgtgctcaac ctgggcaaattccacagcatcgttcgtctggtggccttttgtcccttttgcctcatccca,
``` wherein "n" has the above outlined preferred and most preferred meanings.

The term "polypeptides comprising or consisting of dipeptide-repeats encoded by genomic hexanucleotide repeats" refers to polypeptides that comprise dipeptide repeats, preferably of 9 or more consecutive identical dipeptides. It is more preferred that the polypeptides comprise more than 10, more than 15, more than 20, more than 25, more than 30, more than 35, more than 40, more than 45, more than 50 dipeptide repeats. In preferred embodiments the polypeptide comprises or consists of dipeptide-repeats with two different amino acids, preferably with a sequence selected from the group consisting of $(Gly-Ala)_a$, $(Gly-Pro)_b$, $(Gly-Arg)_c$, $(Ala-Pro)_d$, $(Pro-Arg)_e$, $(Gly-Leu)_f$, $(Ala-Trp)_g$, $(Pro-Gly)_h$, $(Ala-Gln)_j$, $(Gly-Pro)_k$, and $(Pro-Arg)_l$ wherein a is an integer of 16 or more, preferably 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1,000, 1,500, 2,000, 2,500, 3,000, 3,500, 4,000, 4,500, 5,000 or more; b is an integer of 28 or more, preferably 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1,000, 1,500, 2,000, 2,500, 3,000, 3,500, 4,000, 4,500, 5,000 or more; c is an integer of 21 or more, preferably 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1,000, 1,500, 2,000, 2,500, 3,000, 3,500, 4,000, 4,500, 5,000 or more; d is an integer of 17 or more, preferably 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1,000, 1,500, 2,000, 2,500, 3,000, 3,500, 4,000, 4,500, 5,000 or more; e is an integer of 24 or more, preferably 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1,000, 1,500, 2,000, 2,500, 3,000, 3,500, 4,000, 4,500, 5,000 or more; f is an integer of 15 or more, preferably 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1,000, 1,500, 2,000, 2,500, 3,000, 3,500, 4,000, 4,500, 5,000 or more; g is an integer of 9 or more, preferably 10, 15, 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1,000, 1,500, 2,000, 2,500, 3,000, 3,500, 4,000, 4,500, 5,000 or more; h is an integer of 28 or more, preferably 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1,000, 1,500, 2,000, 2,500, 3,000, 3,500, 4,000, 4,500, 5,000 or more; j is an integer of 16 or more, preferably 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1,000, 1,500, 2,000, 2,500, 3,000, 3,500, 4,000, 4,500, 5,000 or more; k is an integer of 28 or more, preferably 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1,000, 1,500, 2,000, 2,500, 3,000, 3,500, 4,000, 4,500, 5,000 or more; and l is an integer of 24 or more, preferably 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1,000, 1,500, 2,000, 2,500, 3,000, 3,500, 4,000, 4,500, 5,000 or more.

5' and 3' of the genomic repeat region further polypeptide encoding regions termed "non-repetitive regions" are located. The sequence of the non-repetitive regions depends on the genomic location of the hexanucleotide repeat region. Accordingly, the DPRs may further comprise additional amino acid sequences at its N- and/or C-Terminus. A polypeptide comprising a dipeptide repeat region further comprises additional C-terminal amino acid sequence encoded by the genomic region 3' of the repeat region. The exact start site of translation is unknown. In the case of RAN-translation the start site may be within the repeat region or within the flanking region. Initiation from a non-canonical start-codon may also lead to an N-terminal flanking region with the largest N-terminal region extending to the first in-frame stop-codon at the 5' end of the RNA. Depending on the transcription initiation of the RAN-translated mRNA encoding the respective DPR, the DPR may also comprise N-terminal amino acid sequence encoded by the genomic region 5' of the repeat region. The length of the respective non-repetitive C-terminal amino acid sequence depends on the position of the first STOP codon in the respective reading frame that gives rise to the DPR. Thus, while two diseases each characterized by expansion of hexanucleotide repeats, however, in different genomic regions may lead to identical DPRs the C- and/or N-terminal non-repetitive regions comprised in the polypeptide will vary depending on the genomic context and will allow distinguishing between two diseases characterized by expansion of genomic hexanucleotide repeats. For each disease characterized by hexanucleotide repeats the skilled person is able to determine the respective 5' and/or 3' genomic region and, thus, the amino acid sequences that may be comprised N- and/or C-terminally of the DPR. Polymorphisms in the 3' region of the gGGGCC repeat may cause frame shifts in patients exhibiting an expansion of the hexanucleotide repeat in the C9orf72 gene.

Amino acid sequences that may be comprised at the C-terminus of the DPRs characteristic for ALS, FTD, or ALS-FTD include for:

```
                                        (SEQ ID NO: 3)
(i) the (Gly-Ala) repeat:
    WSGRARGRARGGAAVAVPAPAAAEAQAVASG;

(SEQ ID NO: 4)
(ii) the (Gly-Pro) repeat:
    GRGRGGPGGGPGAGLRLRCLRPRRRRRRRWRVGE or no C-terminal sequence is the antisense
    GP-repeat isdirectly followed by a STOP-
    codon.

(SEQ ID NO: 5)
(iii) the (Gly-Arg) repeat:
    GVVGAGPGAGPGRGCGCGACARGGGGAGGGEWVSEEAASWRVAV

WGSAAGKRRG;

(SEQ ID NO: 6)
(iv) the (Ala-Pro) repeat:
    SARLLSSRACYRLRLFPSLFSSG;

(SEQ ID NO: 7)
(v) the (Pro-Arg) repeat:
    PLARDS.
```

Amino acid sequences that may be comprised at the C-terminus of the DPRs characteristic for SCA36 include for

```
                                        (SEQ ID NO: 8)
(vi) the (Gly-Leu) repeat:
    RLRLRLPWERVPADAEVALTLAPRLPFQVLLHVLFEHAVGYALL

ALEISLLQPQVGEIRGLLWRPRRPSSRGSQHAQRAPTWPAERFG

AGRAWKALDPGVFTLTHG;

(SEQ ID NO: 9)
(vii) the (Ala-Trp) repeat:
    ACACACACPGNGFRQTLRLR;

(SEQ ID NO: 10)
(viii) the (Gly-Pro) repeat:
    APAPAPALGTGSGRR;

(SEQ ID NO: 11)
(ix) the (Ala-Gln) repeat:
    ALSAARTQAETPTVASPAPRNHSSPWRQLPGSARNAASALRRAE

PGSAPAPPTNRRPGTTPSPAFGGAAQGGIARSAGWVVPSAGERA

FSGLCSCAGGRGCRGRAAPGRALQAAKRLGKALSG;

(SEQ ID NO: 12)
(x) the (Gly-Pro) repeat:
    PVCGPNAGRNPHRRVARAPQPLLTMAPAPGFGSQCG;

(SEQ ID NO: 13)
(xi) the (Pro-Arg) repeat:
    PCLRPERRPKPPPSRRPRPATTPHHGASSRVRLAMRLARSGARN

QAPEATPPPPRPIGGRGRHHLRPLEGPPRVVSPGARAGWCRARA

SGPGPASAAARAGVVAGDARPPVGHCRRRNDLGRPFRGNSPVPD

VLVI.
```

Amino acid sequences that may be comprised at the N-terminus of the DPRs characteristic for ALS, FTD, or ALS-FTD include for

```
                                        (SEQ ID NO: 14)
(i) the (Gly-Ala) repeat:
    QALELRSRAL;

(SEQ ID NO: 15)
(ii) the (Gly-Pro) repeat:
    GRESKEEARSPSLVPAPPPPPPPPGSPGPGCRQFHQSLEAKARH

PASVREMRGKVKMRRALRRAPASTRASSRQPNPKQPPARMPPPH

SPTR HRLRLRRRGRRHRNRSPAPGPPPGPPRPRP;

(SEQ ID NO: 16)
(iii) the (Gly-Arg) repeat:
    RLTRRKQGGKQPQPVASSGTQESRAR;

(SEQ ID NO: 17)
(iv) the (Ala-Pro) repeat:
    GEPPLPPAPLPGSRTPNSHPPGCRLLTHPLATACASAAAGAGTA

TAAPPRARPRARPDH;

(SEQ ID NO: 18)
(v) the (Pro-Arg) repeat:
    SPRRQGPSRVPSEPRLGPQKPRAAHPPAFPQARPLSTRGSLFSS

PQRQRSQRVPGKETARVLRAGKQARMQAIPPVARGESPTPSFGQ

RNERESKNASSSEESPRFYPRLFPAAETQTATRQDAASSLTHSP

PPAPPPPRAQAPQPQPRPGPAPGPAPTT
```

Amino acid sequences that may be comprised at the N-terminus of the DPRs characteristic for SCA36 include for

```
                                        (SEQ ID NO: 19)
(vi) the (Gly-Leu) repeat:
    GVVAGRGRRDGGGFGLRSGRRQ;

(SEQ ID NO: 20)
(vii) the (Ala-Trp) repeat:
    QEHQEPDYYPERAFPSRFAACSARPGAARPRQPRPPAQLQRPE

KARSPALGTTQPALRAIPPWAAPPKAGDGVVPGLRLVGGAGAW

PLEPGSARRSALAALRAEPGSWRHGEEWLRGAGDATVGVSACV

RAADR;

(SEQ ID NO: 21)
(viii) the (Gly-Pro) repeat:
    PHCEPNPGAGAMVRSGCGARATRRWGFRPAFGPQTG;

(SEQ ID NO: 22)
(ix) the (Ala-Gln) repeat:
    GSAGPPKEPTDLTHLRLQQTDLLHFLQRQQRVADRVLKQHVQQ

HLEREPGRERQRNLSVCRNPFPGQ;
```

(x) the (Gly-Pro) repeat:
(SEQ ID NO: 23)
SPPLPSAPAARSRPRAQTARATAPGTGAGARASTQPQRLPEPV
PRAGAGAGAG;

(xi) the (Pro-Arg) repeat:
(SEQ ID NO: 24)
PTACSNSTCNSTWNGSRGASVNATSASAGTRSQGRRRRRR.

Accordingly, the polypeptide resulting from the hexanucleotide repeat in the C9orf72 gene in sense and/or antisense direction may have one of the following sequences:

(i) SEQ ID NO: 25:
qalelrsraGA[GA]$_m$GAwsgrargrarggaavavpapaaaeaqa vasg;

(ii) SEQ ID NO: 26:
GP[GP]$_o$GPgrgrggpgggpgaglrlrclrprrrrrrrwrvge;

(iii) SEQ ID NO: 27:
greskeearspslvpappppppppgspgpgcrqfhqsleakarhpa svremrgkvkmrralrrapastrassrqpnpkqpparmppphspt rhrlrlrrrgrrhrnrspapgpppgpprpGP[GP]$_o$GP;

(iv) SEQ ID NO: 28:
rltrrkqggkqpqpvassgtqesrarGR[GR]$_p$GRgvvgagpgag pgrgcgcgacargggggagggewvseeaaswrvavwgsaagkrrg;

(v) SEQ ID NO: 29:
geppllpaplpgsrtpnshppgcrllthplatacasaaagagtat aapprarprarpdhAP[AP]$_q$APsarllssracyrlrlfpslfss g;

(vi) SEQ ID NO: 30:
sprrqgpsrvpseprlgpqkpraahppafpqarplstrgslfssp qrqrsqrvpgketarvlragkqgrgqipipcpcaaaaaaaagkpg armqaippvargcsptpsfgqrneresknasseesprfyprlgp aaepqtatrqdaassslthspppapppraqapqpqprpgpapgpa pttPR[PR]$_u$PRplards.

Accordingly, the polypeptide resulting from the hexanucleotide repeat in the NOP56 gene in sense and/or antisense direction may have one of the following sequences:

(vii) SEQ ID NO: 31:
gvvagrgrrdgggfglrsgrrqGL[GL]$_s$GLrlrlrlpwervpa daevaltlaprlpfqvllhvlfehavgyallalkeveeisllqp qvgeirgllwrprrpssrgsqhaqraptwpaerfgaggrawkal dpgvftlthg;

(viii) SEQ ID NO: 32:
qehqepdyyperafpsrfaacsarpgaarprqprppaqlqrpek arspalgttqpalraippwaappkagdgvvpglrlvggagawpl epgsarrsalaalraepgswrhgeewlrgagdatvgvsacvraa drAW[AW]$_t$AWacacacacpgngfrqtlrlr;

(ix) SEQ ID NO: 33:
phcepnpgagamvrsgcgaratrrwgfrpagfpqtgPG[PG]$_u$P Gpapapapalgtgsgrr;

(x) SEQ ID NO: 34:
gsagppkeptdlthlrlqqtdllhflqrqqrvadrvlkqhvqqh lerepgrerqrnlsvcrnpfpgqAQ[AQ]$_n$AQalsaartqaetp tvaspaprnhsspwrqlpgsarnaasalrraepgsrghapappt nrrpgttpspafggaaqggiarsagwvvpsagerafsglcscag grgcrgraapgralqaakrlgkalsg;

(xi) SEQ ID NO: 35:
spplpsapaarsrpraqtaratapgtgagarastqpqrlpepvp ragagagagGP[GP]$_x$GPvcgpnagrnphrrvarapqplltmap apgfgsqcg;

(xii) SEQ ID NO: 36:
ptacsnstcnstwngsrgasvnatsasagtrsqgrrrrrrPR [PR]$_y$PRpclrperrpkpppsrrprpattphhgassrvrlamrl arsgarnqapeatppppppriggrgrhhlrplegpprvvspgara gwcrarasgpfpasaaaragvvagdarppvghcrrrndlgrpfr gnspvpdvlvi, wherein m is an integer of 10 or more, preferably 15, 20 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1,000, 1,500, 2,000, 2,500, 3,000, 3,500, 4,000, 4,500, 5,000 or more; "o" is an integer of 10 or more, preferably 15, 20 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1,000, 1,500, 2,000, 2,500, 3,000, 3,500, 4,000, 4,500, 5,000 or more; "p" is an integer of 10 or more, preferably 15, 20 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1,000, 1,500, 2,000, 2,500, 3,000, 3,500, 4,000, 4,500, 5,000 or more; "q" is an integer of 10 or more, preferably 15, 20 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1,000, 1,500, 2,000, 2,500, 3,000, 3,500, 4,000, 4,500, 5,000 or more; "r" is an integer of 10 or more, preferably 15, 20 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1,000, 1,500, 2,000, 2,500, 3,000, 3,500, 4,000, 4,500, 5,000 or more; "s" is an integer of 10 or more, preferably 15, 20 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1,000, 1,500, 2,000, 2,500, 3,000, 3,500, 4,000, 4,500, 5,000 or more; "t" is an integer of 10 or more, preferably 15, 20 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1,000, 1,500, 2,000, 2,500, 3,000, 3,500, 4,000, 4,500, 5,000 or more; "u" is an integer of 10 or more, preferably 15, 20 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1,000, 1,500, 2,000, 2,500, 3,000, 3,500, 4,000, 4,500, 5,000 or more;

"w" is an integer of 10 or more, preferably 15, 20 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1,000, 1,500, 2,000, 2,500, 3,000, 3,500, 4,000, 4,500, 5,000 or more; "x" is an integer of 10 or more, preferably 15, 20 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1,000, 1,500, 2,000, 2,500, 3,000, 3,500, 4,000, 4,500, 5,000 or more; and "y" is an integer of 10 or more, preferably 15, 20 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1,000, 1,500, 2,000, 2,500, 3,000, 3,500, 4,000, 4,500, 5,000 or more.

It is preferred that the C-terminus of the amino acid sequences according to SEQ ID NOs: 14 to 24 is connected via a peptide bond with the N-terminus of the respectively indicated DPR. Preferably, the DPR comprises at least three contiguous, more preferably at least five contiguous amino acids, more preferably at least ten contiguous amino acids of the amino acids according to SEQ ID NOs: 14 to 24, most preferably the entire amino acid sequence.

The term "aggregates" as used herein refers to the intra- or extracellular accumulation of peptides, polypeptides or proteins.

The terms "sample" or "sample of interest" are used interchangeably herein, referring to a part or piece of a tissue, organ or individual, typically being smaller than such tissue, organ or individual, intended to represent the whole of the tissue, organ or individual. Upon analysis a sample provides information about the tissue status or the health or diseased status of an organ or individual. Examples of samples include but are not limited to fluid samples such as blood, serum, plasma, synovial fluid, lymphatic fluid, cerebrospinal fluid, meningeal fluid, glandular fluid, fine needle aspirate, spinal fluid and other body fluids (urine, saliva), as well as biopsy samples or solid samples such as tissue extracts of the brain or spinal cord. Further examples of samples include cell cultures (e.g., patient derived lymphoblasts) or tissue cultures.

Analysis of a sample may be accomplished on a visual or chemical basis. Visual analysis includes but is not limited to microscopic imaging or radiographic scanning of a tissue, organ or individual allowing for the evaluation of a sample. Chemical analysis includes but is not limited to the detection of the presence or absence of specific indicators or the detection of the alterations in their amount or level.

The term "ligand" as used herein refers to any substance or compound that is able to specifically interact with, e.g., to specifically bind to or to form a complex with, the specified molecule, e.g., a polypeptide of the invention comprising or consisting of a dipeptide repeat.

The term "inhibitor" refers to a substance, e.g., a ligand, which blocks the action of another compound, i.e., a receptor molecule. Typically, inhibitors act by binding to the active site of the receptor molecule, or by interacting with unique binding sites not normally involved in the regulation of the activity of the receptor molecule. The activity of the inhibitor may be reversible or irreversible depending on the longevity of the interaction of the inhibitor-receptor molecule complex. Examples of inhibitors include but are not limited to nucleic acid molecules, such as siRNAs or miRNAs, or proteins such as transcription factors, immunoglobulin molecules, antibodies, antibody-like proteins, peptidomimetics, hormones, cytokines, growth factors, or neurotransmitters.

The term "transcription factor" as used herein refers to a protein which binds to a specific nucleic acid sequence and thereby controls the transcription of the genetic information. Transcription factors perform their function alone or in complex with other proteins, by promoting (as an activator), or blocking (as a repressor) e.g., by recruiting the RNA polymerase to a specific gene. Transcription factors may bind to either enhancer or promoter regions in the DNA adjacent to the ORF of the gene they regulate. Transcription factors use a variety of mechanisms to regulate gene expression, e.g., by stabilizing or blocking the binding of the RNA polymerase to the DNA, by catalyzing the acetylation or deacetylation of histone proteins, or by recruiting coactivator or corepressor proteins to the transcription factor-DNA complex. Examples of transcription factors include but are not limited to Leucine zipper factors (bZIP) such as AP-1 (-like) components, CREB, C/EBP-like factors, bZIP/PAR; Helix-loop-helix factors (bHLH) such as ubiquitous (class A) factors, myogenic transcription factors (MyoD), achaete-scute, tal, twist, atonal, hen; Helix-loop-helix/leucine zipper factors (bHLH-ZIP) such as Ubiquitous bHLH-ZIP factors, Cell-cycle controlling factors; NF-1 (A, B, C, X); RF-X (1, 2, 3, 4, 5, ANK); bHSH; Zinc-coordinating DNA-binding domains such as Cys4 zinc finger of nuclear receptor type (Steroid hormone receptors, Thyroid hormone receptor-like factors), diverse Cys4 zinc fingers (GATA-Factors), Cys2His2 zinc finger domain (ubiquitous factors, developmental/cell cycle regulators, large factors with NF-6B-like binding properties); Cys6 cysteine-zinc cluster, Zinc fingers of alternating composition; Helix-turn-helix such as Homeo domain (Homeo domain only, POU domain factors, Homeo domain with LIM region, homeo domain plus zinc finger motifs); paired box (Paired plus homeo domain, Paired domain only); Fork head/winged helix (developmental regulators, tissue-specific regulators, cell-cycle controlling factors, other regulators); Heat Shock Factors, Tryptophan clusters (Myb, Ets-type, interferon regulatory factors); TEA (transcriptional enhancer factor) domain (TEAD1, TEAD2, TEAD3, TEAD4); beta-Scaffold Factors with Minor Groove Contacts such as RHR (Rel/ankyrin, NF-kappaB, NFAT (Nuclear Factor of Activated T-cells), ankyrin); STAT; p53; MADS box (Regulators of differentiation; includes (Mef2), Responders to external signals, SRF (serum response factor) (SRF), Metabolic regulators (ARG80)); beta-Barrel alpha-helix transcription factors; TATA binding proteins, HMG-box (SOX genes, SRY, TCF-1, HMG2-related, SSRP1, MATA); Heteromeric CCAAT factors, Grainyhead; Cold-shock domain factors; Runt, and other transcription factors such as copper fist proteins, HMGI(Y) (HMGA1), Pocket domain, E1A-like factors, AP2/EREBP-related factors (AP2, EREBP, ARF, ABI).

In the context of the present invention the term "RNA interacting factor" is used to refer to further regulatory elements which are involved in the regulation of gene expression, i.e., in the regulation of transcription, RNA splicing, and translation. Such RNA interacting factors include, e.g., a splicing factor, a factor promoting or repressing the activity of a splicing factor, a factor promoting or repressing cytoplasmic mRNA trafficking, factors influencing the nuclear import and export, or factors affecting mRNA stability, turnover, translation, etc. Preferred, RNA interacting factors include but are not limited to heterogeneous nuclear ribonucleoproteins A2/B1 (hnRNP A2/B), heterogeneous nuclear ribonucleoproteins A3 (hnRNP A3), Nucleoporin p62 (p62), the splicing factor proline- and glutamine-rich SFPQ, the splicing factor 3B subunit 3 (SF3B3), the ELAV-like protein 1 (ELAV1), the interleukin enhancer-binding factor 3 (ILF3), the non-POU domain-containing octamer-binding protein (NONO), the heterogeneous nuclear ribonucleoprotein R (HNRPR), the heterogeneous nuclear ribonucleoprotein A3 (ROA3), the heterogeneous nuclear ribonucleoprotein L (HNRPL), the scaffold attachment factor B1 (SAFB1), the insulin-like growth factor 2 mRNA-binding protein 1 (IF2B1), the scaffold attachment factor B2 (SAFB2), the heterogeneous nuclear ribonucleoprotein A1 (ROA1), the double-stranded RNA-specific adenosine deaminase (DSRAD), the putative pre-mRNA-splicing factor ATP-dependent RNA (DHX15), the interleukin enhancer-binding factor 2 (ILF2), the putative ATP-dependent RNA helicase DHX30 (DHX30), the heterogeneous nuclear ribonucleoprotein K (HNRPK), the nucleolar RNA helicase 2 (DDX21), or the RNA-binding protein FUS (FUS). Further examples of RNA interacting factors include but are not limited to EIF2S1, EIF2S2, EIF2S3, eIF4E, eIF4G1, eIF4G2, eIF4A1, eIF4A2, eIF4A3, eIF4B, eIF2B1, eIF2B2, eIF2B3, eIF2B4, eIF2B5, Dbr1, RPL38, HNRNPK, HNRNPE, HNRNPL, HNRNPA1, HNRNPA3 and HNRNPC.

The term "ligand" is used in the present invention to refer to a chemical moiety that specifically binds to an antigen, preferably a polypeptide of the invention. Preferred ligands are antibodies or antigen-binding fragments thereof, antibody-like proteins or peptidomimetics.

The term "immunoglobulin (Ig)" as used herein refers to immunity conferring glycoproteins of the immunoglobulin superfamily. "Surface immunoglobulins" are attached to the membrane of effector cells by their transmembrane region and encompass molecules such as but not limited to B-cell receptors, T-cell receptors, class I and II major histocompatibility complex (MHC) proteins, beta-2 microglobulin (β2M), CD3, CD4 and CD8. Typically, the term "antibody" as used herein refers to secreted immunoglobulins which lack the transmembrane region and can thus be released into the bloodstream and body cavities. Antibodies are grouped into different isotypes based on the heavy chain they possess. There are five types of human Ig heavy chains denoted by the Greek letters α, δ, ε, γ, and μ. The type of heavy chain present defines the class of antibody, i.e., these chains are found in IgA, IgD, IgE, IgG, and IgM antibodies, respectively, each performing different roles, and directing the appropriate immune response against different types of antigens. Distinct heavy chains differ in size and composition; α and γ comprise approximately 450 amino acids, while μ and ε have approximately 550 amino acids (Janeway et al. (2001) Immunobiology, Garland Science). Antibodies comprise four polypeptide chains, namely two heavy (H) chains and two light (L) chains inter-connected by disulfide bonds. Each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. CDRs for heavy and light chains can be determined as known in the art. For example, the following set of rules may be used to find the CDRs within an antibody light and heavy chain sequence, respectively:

Light chain CDR-1: Start: approx. residue 24, Residue before the CDR-1 always a Cys, Residue after the CDR1 always a Trp. Typically Trp-Tyr-Gln, but also, Trp-Leu-Gln, Trp-Phe-Gln, Trp-Tyr-Leu; Length: 10 to 17 residues.

Light chain CDR-2: Start: always 16 residues after the end of L1, residues before generally Ile-Tyr, but also Val-Tyr, Ile-Lys, Ile-Phe, Length always 7 residues.

Light chain CDR-3: Start: always 33 residues after end of CDR-2; residue before always Cys, Residues after always Phe-Gly-XXX-Gly, Length: 7 to 11 residues.

Heavy chain CDR-1: Start: approx. residue 26, always 4 after a Cys (based on the Chothia AbM definition, Kabat definition starts 5 residues later); residues before always Cys-XXX-XXX-XXX; residues after always a Trp. Typically Trp-Val, but also Trp-Ile, Trp-Ala, Length: 10 to 12 residues (AbM definition, Chothia definition excludes the last 4 residues).

Heavy chain CDR-2: Start: always 15 residues after the end of Kabat/AbM definition, of heavy chain CDR-1; residues before: typically Leu-Glu-Trp-Ile-Gly, but a number of variations, residues after Lys/Arg-Leu/Ile/Val/Phe/Thr/Ala-Thr/Ser/Ile/Ala, Length Kabat definition 16 to 19 residues (definition according to AbM; Chothia definition ends 7 residues earlier).

Heavy chain CDR-3: Start: always 33 residues after end of heavy chain CDR-2 (always 2 amino acid residues after a Cys); Residues before always Cys-XXX-XXX (typically Cys-Ala-Arg); Residues after always Trp-Gly-XXX-Gly; Length: 3 to 25 residues. This set of rules is known to the skilled person and can also be found at Worlwide Website bioinf.org.uk/abs/#cdrid.

The term "human antibody", as used herein, is intended to include antibodies having variable and constant regions derived from human germline immunoglobulin sequences. The human mAbs may include amino acid residues not encoded by human germline immunoglobulin sequences (e.g., mutations introduced by random or site-specific mutagenesis in vitro or by somatic mutation in vivo), for example in the CDRs. However, the term "human antibody", as used herein, is not intended to include "humanized antibodies" in which the CDR sequences derived from the germline of another mammalian species (e.g., mouse) have been grafted onto human FR sequences. Human antibodies also include antibodies isolated from human immunoglobulin libraries or from animals transgenic for one or more human immunoglobulin and that do not express endogenous immunoglobulins.

The term "monoclonal antibody", as used herein, refers to a preparation of antibody molecules of a single molecular composition. A monoclonal antibody displays a single binding specificity and affinity for a particular epitope. In one embodiment, the monoclonal antibodies are produced by a hybridoma which includes a B-cell obtained from a non-human animal, e.g., mouse, fused to an immortalized cell. The term "recombinant antibody", as used herein, includes all antibodies that are prepared, expressed, created or isolated by recombinant means, such as (a) antibodies isolated from an animal (e.g., a mouse) that is transgenic or transchromosomal with respect to the immunoglobulin genes or a hybridoma prepared therefrom, (b) antibodies isolated from a host cell transformed to express the antibody, e.g., from a transfectoma, (c) antibodies isolated from a recombinant, combinatorial antibody library, and (d) antibodies prepared, expressed, created or isolated by any other means that involves splicing of immunoglobulin gene sequences to other DNA sequences. As used herein, a "heterologous antibody" is defined in relation to a transgenic organism producing such an antibody. This term refers to an antibody having an amino acid sequence or an encoding nucleic acid sequence corresponding to that found in an organism not consisting of the transgenic organism, and being generally derived from a species other than the transgenic organism. As used herein, a "heterohybrid antibody" refers to an antibody having light and heavy chains originating from different organisms. For example, an antibody having a human heavy chain associated with a murine light chain is a heterohybrid antibody.

The term "antigen-binding fragments" refers to fragments of an antibody which retain the function of specifically binding an antigen or antigenic protein but which lack some or all other structural features of an antibody or artificial constructs that comprise parts of antibodies. Preferred examples of antigen-binding fragments include but are not limited to the following: Fab fragments, Fc fragment, Fab' fragment, F(ab')$_2$, single domain antibodies (sdAb), Nanobodies, single chain Fv, Divalent single-chain variable fragments (di-scFvs), tandem scFvs, diabodies, single-chain diabodies (scDB), triabodies, Bi-specific T-cell engagers (BiTEs), or dual affinity retargeting molecules (DART molecules).

"Fab fragments" (also referred to as "Fab portion" or "Fab region") each with a single antigen binding site, and a residual "Fc fragment" (also referred to as "Fc portion" or "Fc region") whose name reflects its ability to crystallize readily. "Fab' fragment", which refers to a Fab fragment additionally comprising the hinge region of an Ig molecule, while "F(ab')$_2$ fragments" are understood to comprise two Fab' fragments being either chemically linked or connected via a disulfide bond. While sdAb (Desmyter et al. 1996) and "Nanobodies" only comprise a single $V_H$ domain, "single chain Fv (scFv)" fragments comprise the heavy chain variable domain joined via a short linker peptide to the light chain variable domain (Huston et al. 1988). di-scFvs can be engineered by linking two scFvs (scFvA-scFvB). This can be done by producing a single peptide chain with two $V_H$ and two $V_L$ regions, yielding "tandem scFvs" ($V_H$A-$V_L$A-$V_H$B-$V_L$B). Another possibility is the creation of scFvs with linkers that are too short for the two variable regions to fold together, forcing scFvs to dimerize. Usually linkers with a length of 5 residues are used to generate these dimers. This type is known as "diabodies". Still shorter linkers (one or two amino acids) between a $V_H$ and $V_L$ domain lead to the formation of monospecific trimers, so-called "triabodies" or "tribodies". Bi-specific diabodies are formed by expressing two chains with the arrangement $V_H$A-$V_L$B and $V_H$B-$V_L$A or $V_L$A-$V_H$B and $V_L$B-$V_H$A, respectively. Single-chain diabodies (scDb) comprise a $V_H$A-$V_L$B and a $V_H$B-$V_L$A fragment which are linked by a linker peptide (P) of 12-20 amino acids, preferably 14 amino acids ($V_H$A-$V_L$B-P-$V_H$B-$V_L$A). "Bi-specific T-cell engagers (BiTEs)" are fusion proteins consisting of two scFvs of different antibodies wherein one of the scFvs binds to T cells via the CD3 receptor, and the other to a tumor cell via a tumor specific molecule (Kufer et al. 2004). Dual affinity retargeting molecules ("DART" molecules) are diabodies additionally stabilized through a C-terminal disulfide bridge.

The term "antibody-like protein" refers to a protein having similar properties to an antibody in that it binds to an antigen or antigenic protein without necessarily having the structural features of an antibody. Antibody-like proteins may occur naturally or may be designed artificially, e.g., biotechnologically. Examples of naturally occurring antibody-like proteins include but are not limited to antigen-binding proteins such as the family of lipocalins, which represent a family of diverse proteins which normally serve for the storage or transport of physiologically important compounds. They share a conserved barrel of eight antiparallel β-strands as their central folding motif and comprise at one end of this barrel structure six hypervariable loops which are connected to each pair of β-strands. These loops form the entrance to the binding pocket. The structural diversity among the members of the lipocalin family reflects the differing shapes and chemical properties of their binding partners. Thus, although being composed of a single polypeptide chain and being much smaller than immunoglobulins, they exhibit a vast potential to bind antigens of differing specificities. Examples of artificially designed antibody-like proteins include scaffold-based proteins which are generated by fusing peptides with known affinity towards a certain target or by inserting said peptides into a carrier protein to combine the binding properties of the peptide with the desired favorable characteristics of the scaffold carrier.

In the context of the present invention the term "peptidomimetics" is used to refer to any molecule whose essential elements (pharmacophore) mimic a natural peptide or protein in 3D space and which retains the ability to interact with the biological target and produce the same biological effect. Peptidomimetics include small protein-like chains designed to mimic a peptide which may typically be obtained either by modifying an existing peptide, or by designing similar systems that mimic peptides, such as peptoids and β-peptides. Irrespective of the approach, the altered chemical structure is designed to adjust the molecular properties advantageously in that, e.g., the stability or biological activity is increased or decreased. According modifications involve changes to the peptide that will not occur naturally including but not limited to altered backbones and the incorporation of non-natural amino acids.

The terms "specific binding" or "specifically binding" to an antigen refers to the ability of a ligand to bind to an antigenic determinant of an antigen with high affinity. In that context "high affinity" means that the $K_d$ for the interaction is below $1\times10^{-5}$ M, preferably below $1\times10^{-6}$ M, more preferably below $1\times10^{-7}$, even more preferably below $1\times10^{-8}$ M and most preferably below $1\times10^{-9}$ M.

The terms "pharmaceutical", "pharmaceutical composition", "medicament", "medical agent", "agent" and "drug" are used interchangeably herein referring to a substance and/or a combination of substances being used for the identification, prevention or treatment of a tissue status or disease "Pharmaceutically acceptable" means approved by a regulatory agency of the federal or a state government or listed in the U.S. Pharmacopeia or other generally recognized pharmacopeia for use in animals, and more particularly in humans.

The term "active ingredient" refers to the substance in a pharmaceutical composition or formulation that is biologically active, i.e., that provides pharmaceutical value. A pharmaceutical composition may comprise one or more active ingredients which may act in conjunction with or independently of each other. The active ingredients can be formulated as neutral or salt forms. Pharmaceutically acceptable salts include those formed with free amino groups such as those derived from hydrochloric, phosphoric, acetic, oxalic, and tartaric acids, etc., and those formed with free carboxyl groups, such as but not limited to those derived from sodium, potassium, ammonium, calcium, ferric hydroxides, isopropylamine, triethylamine, 2-ethylamino ethanol, histidine, procaine, and the like.

The term "carrier", as used herein, refers to a pharmacologically inactive substance, such as but not limited to a diluent, excipient, or vehicle, with which the therapeutically active ingredient is administered. Such pharmaceutical carriers can be liquid or solid. Liquid carriers include but are not limited to sterile liquids, such as saline solutions in water and oils, including those of petroleum, animal, vegetable or synthetic origin, such as peanut oil, soybean oil, mineral oil, sesame oil and the like. Saline solutions and aqueous dextrose and glycerol solutions can also be employed as liquid carriers, particularly for injectable solutions. A saline solution is a preferred carrier when the pharmaceutical composition is administered intravenously. Examples of suitable pharmaceutical carriers are described in "Remington's Pharmaceutical Sciences" by E. W. Martin.

Suitable pharmaceutical "excipients" include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like.

The term "adjuvant" refers to agents that augment, stimulate, activate, potentiate, or modulate the immune response to the active ingredient of the composition at either the cellular or humoral level, e.g., immunological adjuvants stimulate the response of the immune system to the actual antigen, but have no immunological effect themselves. Examples of such adjuvants include but are not limited to inorganic adjuvants (e.g., inorganic metal salts such as aluminium phosphate or aluminium hydroxide), organic adjuvants (e.g., saponins or squalene), oil-based adjuvants (e.g., Freund's complete adjuvant and Freund's incomplete adjuvant), cytokines (e.g., IL-1β, IL-2, IL-7, IL-12, IL-18, GM-CFS, and INF-γ), particulate adjuvants (e.g., immunostimulatory complexes (ISCOMS), liposomes, or biodegradable microspheres), virosomes, bacterial adjuvants (e.g., monophosphoryl lipid A or muramyl peptides), synthetic adjuvants (e.g., non-ionic block copolymers, muramyl peptide analogues, or synthetic lipid A), or synthetic polynucleotides adjuvants (e.g., polyarginine or polylysine).

Pharmaceuticals are administered via a route of administration suitable to the case. Administration routes include but are not limited to intranasal administration, intramuscular administration, subcutaneous administration, oral administration, and topical administration.

An "intranasal administration" is the administration of a pharmaceutical to the mucosa of the complete respiratory tract including the lung. Typically, the pharmaceutical is administered to the mucosa of the nose. An intranasal administration is achieved by means of instillation, spray or aerosol. Preferably, said administration does not involve perforation of the mucosa by mechanical means such as a needle.

The term "intramuscular administration" refers to the injection of a pharmaceutical into any muscle of an individual or a patient. Preferred intramuscular injections are administered into the deltoid, vastus lateralis or the ventrogluteal and dorsogluteal areas.

The term "subcutaneous administration" refers to the injection of a pharmaceutical into the hypodermis.

The term "oral administration" refers to the administration of a pharmaceutical via the mouth to the gastric system.

A "topical administration" is the administration of a pharmaceutical to any part of the skin without penetrating the skin with a needle or a comparable device. The pharmaceutical may also be administered topically to the mucosa of the mouth, nose, genital region and rectum.

The term "data carrier" refers to any storage medium usable to provide information to the user. These may include but are not limited to manuals, books, booklets, flyers, brochures, and paper, as well as computer readable storage media. The term "computer readable storage medium" as used herein refers to any medium capable of storing data in a format readable by a mechanical device such as a computer. Examples of media include but are not limited to a magnetic disk, an optical disk, a hard disk, RAM, ROM, EEPROM (for example flash memory), an EPROM, a DVD, a Blu-Ray Disc, a floppy disk, a DVD-RW disc, a barcode, and magnetic ink characters.

Embodiments

In the following passages different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous. In the work leading to the present invention, it was surprisingly shown that intronic RNA transcribed from hexanucleotide repeats present in the genome could also be translated by RAN-translation. Based on this result the present invention provides in a first aspect a method of detecting a disease characterized by an expansion of genomic hexanucleotide repeats comprising:

(i) providing a sample from a patient suspected of having or being susceptible to a disease characterized by an expansion of genomic hexanucleotide repeats, and (ii) detecting expression of one or more polypeptides comprising dipeptide-repeats encoded by the genomic hexanucleotide repeats, wherein the expression of said polypeptides indicates the presence of or susceptibility to a disease characterized by an expansion of genomic hexanucleotide repeats.

Preferably the disease characterized by an expansion of genomic hexanucleotide repeats is a neurological disease, more preferably a neurodegenerative disease. In further preferred embodiments the genomic hexanucleotide repeats are selected from the group consisting of GGGGCC and GGCCTG on one DNA stand and the hexanucleotide repeats GGCCCC and CAGGCC on the respective complementary DNA strand, i.e., the disease is characterized by an expansion of the hexanucleotide repeats GGGGCC and/or GGCCTG on one DNA strand and the hexanucleotide repeats GGCCCC and CAGGCC on the respective complementary DNA strand. Preferably, the expansion of genomic hexanucleotide repeats GGGGCC (and/or the complementary hexanucleotide repeats GGCCCC) characterizes a disease selected from the group consisting of ALS, FTD, and ALS-FTD, and the expansion of genomic hexanucleotide repeats GGCCTG (and/or the complementary hexanucleotide repeats CAGGCC) characterizes the disease SCA36. Accordingly, the expansion of the genomic hexanucleotide repeats GGGGCC and/or GGCCTG on one DNA strand and the hexanucleotide repeats GGCCCC and CAGGCC on the respective complementary DNA strand is an indicator of the respective diseases.

The sample provided in (i) may be a fluid sample or a solid sample. In embodiments wherein the sample is a fluid sample, said sample is preferably selected from the group consisting of a sample from blood, serum, plasma, synovial fluid, lymphatic fluid, cerebrospinal fluid, meningeal fluid, glandular fluid, fine needle aspirate, spinal fluid and other body fluids (urine, saliva). In embodiments wherein the sample is a solid sample, said sample may be biopsy sample, i.e., a sample from tissue extracts of the brain or spinal cord. Preferably the sample is a blood sample, plasma sample, serum sample, body fluid sample, sample of the cerebrospinal fluid, lymph fluid sample, meningeal fluid sample, glandular fluid sample, fine needle aspirate sample, spinal fluid sample, and biopsy sample. Furthermore, the sample may be a cell culture or tissue culture. It is particularly preferred that the sample is selected from the group consisting of cerebrospinal fluid, blood, and patient-derived cells, preferably patient-derived fibroblasts or lymphoblasts. Accordingly, the sample may be provided by the patient directly before the method of the present invention is performed or may have been provided earlier and was maintained, e.g., cultured, before said method was performed.

In preferred embodiments, the patient suspected of having a disease characterized by the expansion of genomic hexanucleotide repeats shows early signs or symptoms of said disease.

In preferred embodiments, the patient susceptible to a disease characterized by the expansion of genomic hexanucleotide repeats does not show any symptoms of said disease yet but is vulnerable to the emergence of a disease due to genetic predisposition, lack of vaccination, poorly developed or immature immunity, and/or poor nutritional status.

In preferred embodiment, the expression of one or more polypeptides in step (ii) is detected by detecting the polypeptide comprising dipeptide-repeats encoded by the genomic hexanucleotide repeats. If the polypeptide is detected, it is preferred that a ligand specifically binding to the polypeptide is used. Preferably an antibody or polypeptide binding fragment thereof is used to detect the polypeptide. The ligand may specifically bind to an epitope formed by dipeptide repeat itself, to an epitope formed by the junction between the dipeptide repeat and the N- or C-terminal non-repetitive sequence or to an epitope in the N- or C-terminal sequence. In case that the epitope is formed by the junction between the dipeptide repeats and the N- or C-terminal non-repetitive sequence, it is preferred that the epitope comprises between 3 and 20 amino acids, preferably between 5 and 16 amino acids, more preferably between 7 and 10 amino acids, or the dipeptide repeat sequence and between 3 and 17 amino acids, preferably between 5 and 10 amino acids of the N- or C-terminal non-repetitive sequence. It is preferred that a polypeptide as described in the second and/or third aspect of the present invention is detected. Alternatively, the RNA encoding said polypeptide may be detected. In such detection reaction nucleotides comprising the hexanucleotide repeat, the nucleotides 5' or 3' of the hexanucleotide repeats or both may be detected. It is particularly preferred that mRNA encoding by antisense strand of the respective hexanucleotide repeat region is detected. The present inventors noted that mRNA comprising hexanucleotide repeats specifically interacts with certain nuclear proteins. Accordingly, the expression of one or more polypeptides in step (ii) may also be detected by binding of the mRNA to an RNA interacting factor. RNA transcription products detected in this way preferably comprise GGGGCC-repeats, GGCCCC-repeats, GGCCUG-repeats or CAGGCC-repeats. Preferred RNA interacting factors binding to the GGGGCC hexanucleotide repeats and which may be used for detection include but are not limited to hnRNP A2/B, p62, SFPQ, SF3B3, ELAV1, ILF3, NONO, HNRPR, ROA3, HNRPL, SAFB1, IF2B1, SAFB2, ROA1, DSRAD, DHX15, ILF2, DHX30, HNRPK, DDX21, or FUS, particularly preferred is hnRNP A3. Thus, in a particularly preferred embodiment expression of one or more polypeptides in step (ii) is detected by detecting complexes, preferably agglomerates of hnRNP A3 and mRNA comprising hexanucleotide repeats, preferably GGGGCC-repeats, GGC-CCC-repeats, GGCCUG-repeats or CAGGCC-repeats. This may be affected by antibodies against the RNA interaction factor, preferably hnRNP 3.

In a second aspect, the present invention provides a polypeptide comprising or consisting of dipeptide-repeats with a sequence selected from the group consisting of $(Gly-Ala)_a$, $(Gly-Pro)_b$, $(Gly-Arg)_c$, $(Ala-Pro)_d$, $(Pro-Arg)_e$, $(Gly-Leu)_f$, $(Ala-Trp)_g$, $(Pro-Gly)_h$, $(Ala-Gln)_j$, $(Gly-Pro)_k$, and $(Pro-Arg)_l$ wherein a is an integer of 16 or more, preferably 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1000, 1500, 2000, 2500, 3000, 3500, 4000, 4500, 5000 or more; b is an integer of 28 or more, preferably 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1,000, 1,500, 2,000, 2,500, 3,000, 3,500, 4,000, 4,500, 5,000 or more; c is an integer of 21 or more, preferably 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1,000, 1,500, 2,000, 2,500, 3,000, 3,500, 4,000, 4,500, 5,000 or more; d is an integer of 17 or more, preferably 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1,000, 1,500, 2,000, 2,500, 3,000, 3,500, 4,000, 4,500, 5,000 or more; e is an integer of 24 or more, preferably 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1,000, 1,500, 2,000, 2,500, 3,000, 3,500, 4,000, 4,500, 5,000 or more; f is an integer of 15 or more, preferably 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1,000, 1,500, 2,000, 2,500, 3,000, 3,500, 4,000, 4,500, 5,000 or more; g is an integer of 9 or more, preferably 10, 15, 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1,000, 1,500, 2,000, 2,500, 3,000, 3,500, 4,000, 4,500, 5,000 or more; h is an integer of 28 or more, preferably 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1,000, 1,500, 2,000, 2,500, 3,000, 3,500, 4,000, 4,500, 5,000 or more; j is an integer of 16 or more, preferably 20, 25, 30, 35, 40, 45, 50, 55, 60 or more; k is an integer of 28 or more, preferably 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1,000, 1,500, 2,000, 2,500, 3,000, 3,500, 4,000, 4,500, 5,000 or more; and l is an integer of 24 or more, preferably 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1,000, 1,500, 2,000, 2,500, 3,000, 3,500, 4,000, 4,500, 5,000 or more.

In embodiments of the second aspect, the polypeptide comprises further amino acids at its C-Terminus and/or at its N-Terminus. Preferably the polypeptide comprises or consists of (i) $(Gly-Ala)_a$ dipeptide repeats, wherein a is an integer of 16 or more, preferably 20 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1,000, 1,500, 2,000, 2,500, 3,000, 3,500, 4,000, 4,500, 5,000 or more; at least three contiguous amino acids of the amino acid sequences according to SEQ ID NO: 3 are comprised at its C-terminus; or at least three contiguous amino acids of the amino acid sequences according to SEQ ID NO: 14 are comprised at its N-terminus; or at least three contiguous amino acids of the amino acid sequences according to SEQ ID NO: 3 are comprised at its C-terminus and at least three contiguous amino acids of the amino acid sequences according to SEQ ID NO: 14 are comprised at its N-terminus;

(ii) $(Gly-Pro)_b$ dipeptide repeats, wherein b is an integer of 28 or more, preferably 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1,000, 1,500, 2,000, 2,500, 3,000, 3,500, 4,000, 4,500, 5,000 or more; and at least three contiguous amino acids of the amino acid sequences according to SEQ ID NO: 4 or are comprised at its C-terminus; or at least three contiguous amino acids of the amino acid sequences according to SEQ ID NO: 15 are comprised at its N-terminus; at least three contiguous amino acids of the amino acid sequences according to SEQ ID NO: 4 or are comprised at its C-terminus and at least three contiguous amino acids of the amino acid sequences according to SEQ ID NO: 15 are comprised at its N-terminus;

(iii) $(Gly-Arg)_c$ dipeptide repeats, wherein c is an integer of 21 or more, preferably 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1,000, 1,500, 2,000, 2,500, 3,000, 3,500, 4,000, 4,500, 5,000 or more; at least three contiguous amino acids of the amino acid sequences according to SEQ ID NO: 5 are comprised at its C-terminus; or at least three contiguous amino acids of the amino acid sequences according to SEQ ID NO: 16 are comprised at its N-terminus; at least three contiguous amino acids of the amino acid sequences according to SEQ ID NO: 5 are comprised at its C-terminus and at least three contiguous amino acids of the amino acid sequences according to SEQ ID NO: 16 are comprised at its N-terminus;

(iv) $(Ala-Pro)_d$ dipeptide repeats, wherein d is an integer of 17 or more, preferably 20 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1,000, 1,500, 2,000, 2,500, 3,000, 3,500, 4,000, 4,500, 5,000 or more; at least three contiguous amino acids of the amino acid sequences according to SEQ ID NO: 6 are comprised at its C-terminus; or at least three contiguous amino acids of the amino acid sequences according to SEQ ID NO: 17 are comprised at its N-terminus; at least three contiguous amino acids of the amino acid sequences according to SEQ ID NO: 6 are comprised at its C-terminus and at least three contiguous amino acids of the amino acid sequences according to SEQ ID NO: 17 are comprised at its N-terminus;

(v) $(Pro-Arg)_e$ dipeptide repeats, wherein e is an integer of 24 or more, preferably 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1,000, 1,500, 2,000, 2,500, 3,000, 3,500, 4,000, 4,500, 5,000 or more; at least three contiguous amino acids of the amino acid sequences according to SEQ ID NO: 7 are comprised at its C-terminus; or at least three contiguous amino acids of the amino acid sequences according to SEQ ID NO: 18 are comprised at its N-terminus; at least three contiguous amino acids of the amino acid sequences according to SEQ ID NO: 7 are comprised at its C-terminus and at least three contiguous amino acids of the amino acid sequences according to SEQ ID NO: 18 are comprised at its N-terminus;

(vi) $(Gly-Leu)_f$ dipeptide repeats, wherein f is an integer of 15 or more, preferably 20 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1,000, 1,500, 2,000, 2,500, 3,000, 3,500, 4,000, 4,500, 5,000 or more; and at least three contiguous amino acids of the amino acid sequences according to SEQ ID NO: 8 are comprised at its C-terminus; or at least three contiguous amino acids of the amino acid sequences according to SEQ ID NO: 19 are comprised at its N-terminus; at least three contiguous amino acids of the amino acid sequences according to SEQ ID NO: 8 are comprised at its C-terminus and at least three contiguous amino acids of the amino acid sequences according to SEQ ID NO: 19 are comprised at its N-terminus;

(vii) $(Ala-Trp)_g$ dipeptide repeats, wherein g is an integer of 9 or more, preferably 10, 15, 20 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1,000, 1,500, 2,000, 2,500, 3,000, 3,500, 4,000, 4,500, 5,000 or more; at least three contiguous amino acids of the amino acid sequences according to SEQ ID NO: 9 are comprised at its C-terminus; or at least three contiguous amino acids of the amino acid sequences according to SEQ ID NO: 20 are comprised at its N-terminus; at least three contiguous amino acids of the amino acid sequences according to SEQ ID NO: 9 are comprised at its C-terminus and at least three contiguous amino acids of the amino acid sequences according to SEQ ID NO: 20 are comprised at its N-terminus;

(viii) $(Pro-Gly)_h$ dipeptide repeats, wherein h is an integer of 28 or more, preferably 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1,000, 1,500, 2,000, 2,500, 3,000, 3,500, 4,000, 4,500, 5,000 or more; at least three contiguous amino acids of the amino acid sequences according to SEQ ID NO: 10 are comprised at its C-terminus; or at least three contiguous amino acids of the amino acid sequences according to SEQ ID NO: 21 are comprised at its N-terminus; at least three contiguous amino acids of the amino acid sequences according to SEQ ID NO: 10 are comprised at its C-terminus and at least three contiguous amino acids of the amino acid sequences according to SEQ ID NO: 21 are comprised at its N-terminus;

(ix) $(Ala-Gln)_j$ dipeptide repeats, wherein j is an integer of 16 or more, preferably 20 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1,000, 1,500, 2,000, 2,500, 3,000, 3,500, 4,000, 4,500, 5,000 or more; at least three contiguous amino acids of the amino acid sequences according to SEQ ID NO: 11 are comprised at its C-terminus; or at least three contiguous amino acids of the amino acid sequences according to SEQ ID NO: 22 are comprised at its N-terminus; at least three contiguous amino acids of the amino acid sequences according to SEQ ID NO: 11 are comprised at its C-terminus and at least three contiguous amino acids of the amino acid sequences according to SEQ ID NO: 22 are comprised at its N-terminus;

(x) (Gly-Pro)$_k$ dipeptide repeats, wherein k is an integer of 28 or more, preferably 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1,000, 1,500, 2,000, 2,500, 3,000, 3,500, 4,000, 4,500, 5,000 or more; at least three contiguous amino acids of the amino acid sequences according to SEQ ID NO: 12 are comprised at its C-terminus; or at least three contiguous amino acids of the amino acid sequences according to SEQ ID NO: 23 are comprised at its N-terminus; or at least three contiguous amino acids of the amino acid sequences according to SEQ ID NO: 12 are comprised at its C-terminus and at least three contiguous amino acids of the amino acid sequences according to SEQ ID NO: 23 are comprised at its N-terminus; or (xi) (Arg-Pro)$_l$ dipeptide repeats, wherein l is an integer of 24 or more, preferably 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1,000, 1,500, 2,000, 2,500, 3,000, 3,500, 4,000, 4,500, 5,000 or more; at least three contiguous amino acids of the amino acid sequences according to SEQ ID NO: 13 are comprised at its C-terminus; or at least three contiguous amino acids of the amino acid sequences according to SEQ ID NO: 25 are comprised at its N-terminus; at least three contiguous amino acids of the amino acid sequences according to SEQ ID NO: 13 are comprised at its C-terminus and at least three contiguous amino acids of the amino acid sequences according to SEQ ID NO: 25 are comprised at its N-terminus.

In these polypeptides it is preferred that the N-terminus of the non-repetitive amino acid sequence according to SEQ ID NOs: 3 to 13 is linked via a peptide bond to the C-terminus of the respectively indicated DPR. In another preferred embodiment the C-terminus of the non-repetitive amino acid sequence according to SEQ ID NOs: 14 to 24 is linked via a peptide bond to the N-terminus of the respectively indicated DPR.

The length of the contiguous amino acid sequence is preferably 5 amino acids, 10 amino acids, 15 amino acids or the entire sequence according to SEQ ID NOs: 3 to 24.

In preferred embodiments, a detectable tag is attached, preferably covalently bound, to said polypeptide. Suitable tags are preferably selected from the group consisting of a fluorophore, a chromophore, a radiolabel, a metal colloid, an enzyme, a chemiluminescent or a bioluminescent molecule. It is particularly preferred that the detectable tag is a fluorophore, preferably GFP, or an enzyme, preferably a luciferase.

In a third aspect the present invention provides a polypeptide comprising or consisting of:

(i) (Gly-Ala)$_m$ dipeptide repeats, wherein m is an integer of 10 or more, preferably 15, 20 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1,000, 1,500, 2,000, 2,500, 3,000, 3,500, 4,000, 4,500, 5,000 or more; at least three contiguous amino acids of the amino acid sequences according to SEQ ID NO: 3 at its C-terminus; or at least three contiguous amino acids of the amino acid sequences according to SEQ ID NO: 14 at its N-terminus; or at least three contiguous amino acids of the amino acid sequences according to SEQ ID NO: 3 at its C-terminus and at least three contiguous amino acids of the amino acid sequences according to SEQ ID NO: 14 at its N-terminus;

(ii) (Gly-Pro)$_o$ dipeptide repeats, wherein o is an integer of 10 or more, preferably 15, 20 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1,000, 1,500, 2,000, 2,500, 3,000, 3,500, 4,000, 4,500, 5,000 or more; at least three contiguous amino acids of the amino acid sequences according to SEQ ID NO: 4 at its C-terminus; or at least three contiguous amino acids of the amino acid sequences according to SEQ ID NO: 15 at its N-terminus; or at least three contiguous amino acids of the amino acid sequences according to SEQ ID NO: 4 at its C-terminus and at least three contiguous amino acids of the amino acid sequences according to SEQ ID NO: 15 at its N-terminus;

(iii) (Gly-Arg)$_p$ dipeptide repeats, wherein p is an integer of 10 or more, preferably 15, 20 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1,000, 1,500, 2,000, 2,500, 3,000, 3,500, 4,000, 4,500, 5,000 or more; at least three contiguous amino acids of the amino acid sequences according to SEQ ID NO: 5 at its C-terminus; or at least three contiguous amino acids of the amino acid sequences according to SEQ ID NO: 16 at its N-terminus; or at least three contiguous amino acids of the amino acid sequences according to SEQ ID NO: 5 at its C-terminus and at least three contiguous amino acids of the amino acid sequences according to SEQ ID NO: 16 at its N-terminus;

(iv) (Ala-Pro)$_q$ dipeptide repeats, wherein q is an integer of 10 or more, preferably 15, 20 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1,000, 1,500, 2,000, 2,500, 3,000, 3,500, 4,000, 4,500, 5,000 or more; at least three contiguous amino acids of the amino acid sequences according to SEQ ID NO: 6 at its C-terminus; or at least three contiguous amino acids of the amino acid sequences according to SEQ ID NO: 17 at its N-terminus; or at least three contiguous amino acids of the amino acid sequences according to SEQ ID NO: 6 at its C-terminus and at least three contiguous amino acids of the amino acid sequences according to SEQ ID NO: 17 at its N-terminus;

(v) (Pro-Arg)$_r$ dipeptide repeats, wherein r is an integer of 10 or more, preferably 1,000, 1,500, 2,000, 2,500, 3,000, 3,500, 4,000, 4,500, 5,000 or more; at least three contiguous amino acids of the amino acid sequences according to SEQ ID NO: 7 at its C-terminus; or at least three contiguous amino acids of the amino acid sequences according to SEQ ID NO: 18 at its N-terminus; or at least three contiguous amino acids of the amino acid sequences according to SEQ ID NO: 7 at its C-terminus, and/or at least three contiguous amino acids of the amino acid sequences according to SEQ ID NO: 18 at its N-terminus;

(vi) (Gly-Leu)$_s$ dipeptide repeats, wherein s is an integer of 10 or more, preferably 15, 20 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1,000, 1,500, 2,000, 2,500, 3,000, 3,500, 4,000, 4,500, 5,000 or more; at least three contiguous amino acids of the amino acid sequences according to SEQ ID NO: 8 at its C-terminus; or at least three contiguous amino acids of the amino acid sequences according to SEQ ID NO: 19 at its N-terminus; or at least three contiguous amino acids of the amino acid sequences according to SEQ ID NO: 8 at its C-terminus, and/or at least three contiguous amino acids of the amino acid sequences according to SEQ ID NO: 19 at its N-terminus;

(vii) (Ala-Trp)$_t$ dipeptide repeats, wherein t is an integer of 10 or more, preferably 15, 20 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1,000, 1,500, 2,000, 2,500, 3,000, 3,500, 4,000, 4,500, 5,000 or more; at least three contiguous amino acids of the amino acid sequences according to SEQ ID NO: 9 at its C-terminus; or at least three contiguous amino acids of the amino acid sequences according to SEQ ID NO: 20 at its N-terminus; or at least three contiguous amino acids of the amino acid sequences according to SEQ ID NO: 9 at its C-terminus, and/or at least three contiguous amino acids of the amino acid sequences according to SEQ ID NO: 20 at its N-terminus;

(viii) (Pro-Gly)$_u$ dipeptide repeats, wherein u is an integer of 10 or more, preferably 15, 20 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1,000, 1,500, 2,000, 2,500, 3,000, 3,500, 4,000, 4,500, 5,000 or more, at least three contiguous amino acids of the amino acid sequences according to SEQ ID NO: 10 at its C-terminus; or at least three contiguous amino acids of the amino acid sequences according to SEQ ID NO: 21 at its N-terminus; or at least three contiguous amino acids of the amino acid sequences according to SEQ ID NO: 10 at its C-terminus and at least three contiguous amino acids of the amino acid sequences according to SEQ ID NO: 21 at its N-terminus;

(ix) (Ala-Gln)$_w$ dipeptide repeats, wherein w is an integer of 10 or more, preferably 15, 20 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1,000, 1,500, 2,000, 2,500, 3,000, 3,500, 4,000, 4,500, 5,000 or more; at least three contiguous amino acids of the amino acid sequences according to SEQ ID NO: 11 at its C-terminus; or at least three contiguous amino acids of the amino acid sequences according to SEQ ID NO: 22 at its N-terminus; or at least three contiguous amino acids of the amino acid sequences according to SEQ ID NO: 11 at its C-terminus and at least three contiguous amino acids of the amino acid sequences according to SEQ ID NO: 22 at its N-terminus;

(x) (Gly-Pro)$_x$ dipeptide repeats, wherein x is an integer of 10 or more, preferably 15, 20 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1,000, 1,500, 2,000, 2,500, 3,000, 3,500, 4,000, 4,500, 5,000 or more; at least three contiguous amino acids of the amino acid sequences according to SEQ ID NO: 12 at its C-terminus; or at least three contiguous amino acids of the amino acid sequences according to SEQ ID NO: 23 at its N-terminus; or at least three contiguous amino acids of the amino acid sequences according to SEQ ID NO: 12 at its C-terminus, and at least three contiguous amino acids of the amino acid sequences according to SEQ ID NO: 23 at its N-terminus; or (xi) (Arg-Pro)$_y$ dipeptide repeats, wherein y is an integer of 10 or more, preferably 15, 20 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1,000, 1,500, 2,000, 2,500, 3,000, 3,500, 4,000, 4,500, 5,000 or more; at least three contiguous amino acids of the amino acid sequences according to SEQ ID NO: 13 at its C-terminus; or at least three contiguous amino acids of the amino acid sequences according to SEQ ID NO: 24 at its N-terminus; or at least three contiguous amino acids of the amino acid sequences according to SEQ ID NO: 13 at its C-terminus and at least three contiguous amino acids of the amino acid sequences according to SEQ ID NO: 24 at its N-terminus.

In these polypeptides it is preferred that the N-terminus of the non-repetitive amino acid sequence according to SEQ ID NOs: 3 to 13 is linked via a peptide bond to the C-terminus of the respectively indicated DPR. In another preferred embodiment the C-terminus of the non-repetitive amino acid sequence according to SEQ ID NOs: 14 to 24 is linked via a peptide bond to the N-terminus of the respectively indicated DPR.

The length of the contiguous amino acid sequence is preferably 5 amino acids, 10 amino acids, 15 amino acids or the entire sequence according to SEQ ID NOs: 3 to 24.

In further embodiments, the polypeptide comprises or consists of a sequence according to any one of the following sequences:

(i) SEQ ID NO: 25:
qalelrsralGA[GA]$_m$GAwsgrargrarggaavavpapaaea qavasg;

(ii) SEQ ID NO: 26:
GP[GP]$_o$GPgrgrggpgggpgaglrlrclrprrrrrrrwrvge;

(iii) SEQ ID NO: 27:
greskeearspslvpapppppppppgspgpgcrqfhqsleakra hpsavremrgkvkmrralrrapastrassrqpnpkqpparmpp phsptrhrlrlrrrgrrhrnrspapgpppgpprprpGP[GP]$_o$

GP;

(iv) SEQ ID NO: 28:
rltrrkqggkqpqpvassgtqesrarGR[GR]$_p$GRgvvgagpga gpgrgcgcgacarggggagggewveseeaaswrvavwgsaagkr rg;

(v) SEQ ID NO: 29:
geppllpaplpgsrtpnshppgcrllthplatacasaaagagta tapprarprarpdhAP[AP]$_q$APsarllssracyrlrlfpslf ssg;

(vi) SEQ ID NO: 30:
sprrqgpsrvpseprlgpqkpraahppafpqarplstrgslfss pqrqrsqrvpgketarvlragkqgrgqipipcpcaaaaaaakp garmqaippvargesptpsfgqrneresknasssseesprfyprl fpaaepqtatrqdaassslthspppappppraqapqpqprpgpap gpapttPR[PR]$_r$PRplards;

(vii) SEQ ID NO: 31:
gvvagrgrrdgggfglrsgrrqGL[GL]$_s$GLrlrlrlpwervpa daevaltlaprlpfqvllhvlfehavgyallalkeveeisllqp qvgeirgllwrprrpssrgsqhaqraptwpaerfgaggrawkal dpgvftlthg;

(viii) SEQ ID NO: 32:
qehqepdyyperafprfaacsarpgaarprqprppaqlqrpeka rspalgttqpalraippwaappkagdgvvpglrlvggagawple pgsarrsalaalraepgswrhgeewlrgagdatvgvsacvraad rAW[AW]$_t$AWacacacacpgngfrqtlrlr;

-continued (ix) SEQ ID NO: 33:
phcepnpgagamvrsgcgaratrrwgfrpafgpqtgPG[PG]$_n$P

Gpapapapalgtgsgrr;

(x) SEQ ID NO: 34:
gsagppkeptdlthlrlqqtdllhfqrqqrvadrvlkqhvqqhl erepgrerqrnlsvcrnpfpgqAQ[AQ]$_o$AQalsaartqaetpt vaspaprnhsspwrqlpgsarnaasalrraepgsrghapapptn rrpgttpspafggaaqggiarsagwvvpsagerafsglcscagg rgcrgraapgralqaakrlgkalsg;

(xi) SEQ ID NO: 35:
spplpsapaarsrpraqtaratapgtgagarastqpqrlpepvp ragagagagGP[GP]$_k$GPvcgpnagrnphrrvarapqplltmap apgfgsqcg;

(xii) SEQ ID NO: 36:
ptacsnstcnstwngsrgasvnatsasagtrsqgrrrrrrrPR

[PR]$_y$PRpclrperrpkpppsrrprpattphhgassrvrlamrl arsgarnqapeatppppripiggrgrhhlrplcgpprvvspgara gwcrarasgpfpasaaaragvvagdarppvghcrrrndlgrpfr gnspvpdvlvi, wherein m is an integer of 10 or more, preferably 15, 20 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1,000, 1,500, 2,000, 2,500, 3,000, 3,500, 4,000, 4,500, 5,000 or more, o is an integer of 10 or more, preferably 15, 20 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1,000, 1,500, 2,000, 2,500, 3,000, 3,500, 4,000, 4,500, 5,000 or more, p is an integer of 10 or more, preferably 15, 20 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1,000, 1,500, 2,000, 2,500, 3,000, 3,500, 4,000, 4,500, 5,000 or more, q is an integer of 10 or more, preferably 15, 20 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1,000, 1,500, 2,000, 2,500, 3,000, 3,500, 4,000, 4,500, 5,000 or more, r is an integer of 10 or more, preferably 15, 20 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1,000, 1,500, 2,000, 2,500, 3,000, 3,500, 4,000, 4,500, 5,000 or more, s is an integer of 10 or more, preferably 15, 20 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1,000, 1,500, 2,000, 2,500, 3,000, 3,500, 4,000, 4,500, 5,000 or more, t is an integer of 10 or more, preferably 15, 20 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1,000, 1,500, 2,000, 2,500, 3,000, 3,500, 4,000, 4,500, 5,000 or more, u is an integer of 10 or more, preferably 15, 20 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1,000, 1,500, 2,000, 2,500, 3,000, 3,500, 4,000, 4,500, 5,000 or more, w is an integer of 10 or more, preferably 15, 20 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1,000, 1,500, 2,000, 2,500, 3,000, 3,500, 4,000, 4,500, 5,000 or more, x is an integer of 10 or more, preferably 15, 20 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1,000, 1,500, 2,000, 2,500, 3,000, 3,500, 4,000, 4,500, 5,000 or more, and y is an integer of 10 or more, preferably 15, 20 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1,000, 1,500, 2,000, 2,500, 3,000, 3,500, 4,000, 4,500, 5,000 or more.

In preferred embodiments, a detectable tag is attached, preferably covalently bound, to said polypeptide. Suitable tags are preferably selected from the group consisting of a fluorophore, a chromophore, a radiolabel, a metal colloid, an enzyme, a chemiluminescent or a bioluminescent molecule. It is particularly preferred that the detectable tag is a fluorophore, preferably GFP, or an enzyme, preferably a luciferase.

In a fourth aspect the present invention provides a ligand which specifically binds to or forms a complex with a polypeptide according to the second and/or third aspect of the present invention or an RNA molecule encoding a polypeptide according to the second and/or third aspect of the present invention. Accordingly, in embodiments of the fourth aspect the ligand interacts with a polypeptide according to the second aspect of the invention, i.e., a polypeptide comprising or consisting of dipeptide-repeats with a sequence selected from the group consisting of (Gly-Ala)$_a$, (Gly-Pro)$_b$, (Gly-Arg)$_c$, (Ala-Pro)$_d$, (Pro-Arg)$_e$, (Gly-Leu)$_f$, (Ala-Trp)$_g$, (Pro-Gly)$_h$, (Ala-Gln)$_j$, (Gly-Pro)$_k$, and (Pro-Arg)$_l$ wherein a is an integer of 16 or more, preferably 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1000, 1500, 2000, 2500, 3000, 3500, 4000, 4500, 5000 or more; b is an integer of 28 or more, preferably 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1,000, 1,500, 2,000, 2,500, 3,000, 3,500, 4,000, 4,500, 5,000 or more; c is an integer of 21 or more, preferably 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1000, 1500, 2000, 2500, 3000, 3500, 4000, 4500, 5000 or more; d is an integer of 17 or more, preferably 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1,000, 1,500, 2,000, 2,500, 3,000, 3,500, 4,000, 4,500, 5,000 or more; e is an integer of 24 or more, preferably 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1,000, 1,500, 2,000, 2,500, 3,000, 3,500, 4,000, 4,500, 5,000 or more; f is an integer of 15 or more, preferably 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1,000, 1,500, 2,000, 2,500, 3,000, 3,500, 4,000, 4,500, 5,000 or more; g is an integer of 9 or more, preferably 10, 15, 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1,000, 1,500, 2,000, 2,500, 3,000, 3,500, 4,000, 4,500, 5,000 or more; h is an integer of 28 or more, preferably 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1,000, 1,500, 2,000, 2,500, 3,000, 3,500, 4,000, 4,500, 5,000 or more; j is an integer of 16 or more, preferably 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1,000, 1,500, 2,000, 2,500, 3,000, 3,500, 4,000, 4,500, 5,000 or more; k is an integer of 28 or more, preferably 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1,000, 1,500, 2,000, 2,500, 3,000, 3,500, 4,000, 4,500, 5,000 or more; and l is an integer of 24 or more, preferably 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1,000, 1,500, 2,000, 2,500, 3,000, 3,500, 4,000, 4,500, 5,000 or more and/or optionally further N- and/or C-terminal non-repetitive sequences. Preferably, the ligand binds to an epitope formed by dipeptide repeat itself, to an epitope formed by the junction between the dipeptide repeat and the N- or C-terminal non-repetitive sequence or to an epitope in the N- or C-terminal non-repetitive sequence.

In embodiments wherein the ligand binds to a polypeptide according to the third aspect of the present invention, it may specifically bind to an epitope formed by dipeptide repeat itself, to an epitope formed by the junction between the dipeptide repeat and the N- or C-terminal non-repetitive sequence or to an epitope in the N- or C-terminal sequence. In case that the epitope is formed by the junction between the dipeptide repeat and the N- or C-terminal non-repetitive sequence, it is preferred that the epitope comprises between 3 and 17 amino acids, preferably between 5 and 10 amino acids of the dipeptide repeat sequence and between 3 and 20 amino acids, preferably between 5 and 16 amino acids, more preferably between 7 and 10 amino acids, of the N- or C-terminal non-repetitive sequence.

In preferred embodiments of the fourth aspect, the ligand is selected from the group consisting of:
(a) antibodies or antigen-binding fragments thereof;
(b) antibody-like proteins; or
(c) peptidomimetics.

Preferably, the antibody is selected from the group consisting of polyclonal, monoclonal, monovalent, bispecific, heteroconjugate, multispecific, recombinant, heterologous, heterohybrid, chimeric, humanized (in particular CDR-grafted), deimmunized, or human antibodies. More preferably the antibody is a humanized antibody. In further preferred embodiments the antibody is an IgG antibody. In further preferred embodiments, the antigen-binding fragment is selected from the group consisting of Fc fragment, Fab fragments, Fab' fragment, F(ab')$_2$ fragments, single domain antibodies (sdAb), nanobodies, single chain Fv (scFv), tandem scFvs, diabodies, bispecific diabodies, single-chain diabodies (scDb), triabodies, bi-specific T-cell engagers (BiTEs), and dual affinity retargeting molecules (DART).

In a further preferred embodiment the antibody or antigen-binding fragment thereof comprises
(i) a heavy chain CDR3 sequence comprising, essentially consisting of, or consisting of the following amino acid sequence: GDX$_1$X$_2$NSHFX$_3$Y (SEQ ID NO: 50), wherein X$_1$ is any amino acid, preferably an aromatic amino acid, more preferably W, Y or F, most preferably Y or F; X$_2$ is any amino acid, preferably a polar amino acid, more preferably a polar uncharged amino acid, most preferably S or T; and X$_3$ is any amino acid, preferably an aliphatic or polar amino acid, more preferably an aliphatic or polar uncharged amino acid, and most preferably A or T; and wherein said amino acid sequence optionally comprises 1, 2 or 3 amino acid exchanges outside X$_1$, X$_2$ and X$_3$, and/or 1, 2 or 3 amino acid deletions and/or 1, 2 or 3 additions, preferably 1, 2, or 3 exchanges, most preferably 1 exchange; and
(ii) a light chain CDR3 sequence comprising, essentially consisting of, or consisting of the following amino acid sequence: QQLVEYPLT (SEQ ID NO: 53), wherein said amino acid sequence optionally comprises 1, 2 or 3 amino acid exchanges, 1, 2 or 3 deletions and/or 1, 2 or 3 additions.

In the context of the present invention the term "aromatic amino acid" refers to F, W, F or H, the term "aliphatic amino acids" comprises non-polar and hydrophobic amino acids, the term "non-polar amino acid" refers to G or A, the term "hydrophobic amino acids" refers to V, L and I, the term "polar amino acids" comprises "polar charged amino acids" and "polar uncharged amino acids", the term "polar uncharged amino acids" refers to S, C, N, Q, T and Y, and the term "polar charged amino acids" refers to D, E, K, R, and H. It is noted that some of these definitions overlap, e.g., H is both an aromatic amino acid and a polar charged amino acid.

Preferably said antibody or antigen-binding fragment thereof comprises a heavy chain CDR3 sequence comprising, essentially consisting of, or consisting of the amino acid sequence GDX$_1$X$_2$NSHFX$_3$Y (SEQ ID NO: 50) modified wherein 1 or 2 or 3 amino acids are exchanged at position 1, 2, 5, 6, 7, 8 and/or 10 and/or wherein 1 or 2 or 3 amino acids are deleted at position 1, 2, 5, 6, 7, 8 and/or 10 and/or wherein 1, 2 or 3 amino acids are added at position 1, 2, 5, 6, 7, 8 and/or 10 or wherein X$_1$ is selected from the group W or Y or F; X$_2$ is selected from the group D, E, K, R, H, S, C, N, Q, T, or Y; or X$_3$ is selected from the group G, A, V, L, I, S, C, N, Q, T and Y, more preferably the heavy chain CDR3 comprises, essentially consists of, or consists of the following amino acid sequences: GDYSNSHFAY (SEQ ID NO: 57) or GDFTNSHFTY (SEQ ID NO: 58) or GDYSNSHFTY (SEQ ID NO: 59) or GDFTNSHFAY (SEQ ID NO: 60) or GDYSNSHFAY (SEQ ID NO 61) or GDFSNSHFTY (SEQ ID NO: 62) or GDFSNSHFAY (SEQ ID NO: 63) or GDYTNSHFAY (SEQ ID NO: 64) and a light chain CDR3 sequence comprising, essentially consisting of, or consisting of amino acid sequence QQLVEYPLT (SEQ ID NO: 53) optionally modified wherein 1 or 2 or 3 amino acids are exchanged at position 1, 2, 3, 4, 5, 6, 7, 8 and/or 9, or wherein 1 or 2 or 3 amino acids are deleted at position 1, 2, 3, 4, 5, 6, 7, 8 and/or 9, or wherein 1, 2 or 3 amino acids are added at position 1, 2, 3, 4, 5, 6, 7, 8 and/or 9, preferably 1, 2, or 3 exchanged, most preferably 1 exchange.

In a further preferred embodiment said antibody or antigen-binding fragment further comprises one or more of the following sequences:
(i) a heavy chain CDR2 sequence comprising, essentially consisting of, or consisting of the amino acid sequence EX$_4$LPGSGX$_5$TK (SEQ ID NO: 51), wherein X$_4$ is any amino acid, preferably an aliphatic or polar amino acid, more preferably a hydrophobic or polar uncharged amino acid, most preferably I or N; and X$_5$ is any amino acid, preferably a polar amino acid, more preferably a polar uncharged amino acid, most preferably S or T and wherein the heavy chain CDR2 sequence optionally comprises 1, 2 or 3 amino acid exchanges outside X$_4$ and X$_5$, 1, 2 or 3 amino acid deletions, and/or 1, 2, 3, 4, 5, 6, 7, 8 or 9 amino acid additions, preferably 1, 2, or 3 exchanges, most preferably 1 exchange and/or up to 7 amino acid additions;

(ii) a heavy chain CDR1 sequence comprising, essentially consisting of, or consisting of the amino acid sequence GYX$_8$FX$_9$GYWIE (SEQ ID NO: 52), wherein X$_8$ is any amino acid, preferably a polar amino acid, more preferably T or K; and X$_9$ is any amino acid, preferably an aliphatic or polar amino acid, more preferably a hydrophobic or uncharged polar amino acid, most preferably I or T; and wherein said amino acid sequence optionally comprises 1, 2 or 3 amino acid exchanges outside X$_8$ and X$_9$, 1, 2 or 3 amino acid deletions, and/or 1, 2 or 3 additions, preferably 1, 2, or 3 exchanges, most preferably 1 exchange;

(iii) a light chain CDR2 comprising, essentially consisting of, or consisting of the amino acid sequence LMSTRAS (SEQ ID NO: 54), wherein said amino acid sequence optionally comprises 1, 2 or 3 amino acid exchanges, 1, 2 or 3 deletions and/or 1, 2 or 3 additions, preferably 1, 2, or 3 exchanges, most preferably 1 exchange; and/or (iv) a light chain CDR1 comprising, essentially consisting of, or consisting of the amino acid sequence RSSKSLLYKDGKTYLN (SEQ ID NO: 55), wherein said amino acid sequence optionally comprises 1, 2 or 3 amino acid exchanges, 1, 2 or 3 deletions and/or 1, 2 or 3 additions, preferably 1, 2, or 3 exchanges, most preferably 1 exchange.

Preferably, said antibody or antigen-binding fragment thereof further comprises a heavy chain CDR2 sequence comprising, essentially consisting of, or consisting of the amino acid sequence EX$_4$LPGSGX$_5$TK (SEQ ID NO: 51), optionally modified wherein 1 or 2 or 3 amino acids are exchanged at position 1, 3, 4, 5, 6, 7, 9 and/or 10 or wherein 1 or 2 or 3 amino acids are deleted at position 1, 3, 4, 5, 6, 7, 9 and/or 10 or wherein 1, 2 or 3 amino acids are added at position 1, 3, 4, 5, 6, 7, 9 and/or 10, preferably 1, 2, or 3 exchanges, most preferably 1 exchange, wherein X$_4$ is preferably selected from the group A, S, C, N, Q, T Y, V, L and I; X$_5$ is preferably selected from the group D, E, K, R, H, S, C, N, Q, T and Y, more preferably the heavy chain CDR2 comprises, essentially consists, or consists of the following amino acid sequences: EILPGSGSTK (SEQ ID NO: 64) or ENLPGSGSTK (SEQ ID NO: 65) or ENLPGSGTTK (SEQ ID NO: 66) or EILPGSGTTK (SEQ ID NO: 67); and/or a heavy chain CDR1 sequence comprising, essentially consisting of, or consisting of the amino acid sequence GYX$_8$FX$_9$GYWIE (SEQ ID NO: 52), optionally modified wherein 1 or 2 or 3 amino acids are exchanged at position 1, 2, 4, 6, 7, 8, 9 and/or 10 or wherein 1 or 2 or 3 amino acids are deleted at position 1, 2, 4, 6, 7, 8, 9 and/or 10 or wherein 1, 2 or 3 amino acids are added at position 1, 2, 4, 6, 7, 8, 9 and/or 10; X$_8$ is preferably selected from the group R, N, D, C, Q, E, K, S, and T; X$_9$ is preferably selected from the group A, R, N, D, C, Q, E, I, L, M, K, S, T, and V; more preferably the heavy chain CDR1 comprises, essentially consists, or consists of the following amino acid sequences: GYTFTGYWIE (SEQ ID NO: 68) or GYKFIGYWIE (SEQ ID NO: 69) or GYKFTGYWIE (SEQ ID NO: 70) or GYTFIGYWIE (SEQ ID NO: 71).

Preferably the antibody or antigen-binding fragment thereof comprises within its heavy chain variable region the above outlined heavy chain CDRs: CDR3; CDR3 and CDR2; CDR3 and CDR1; or CDR3, CDR2, and CDR1. In each case it is preferred that the one or more CDRs are flanked by one or more of the heavy chain framework regions as set out in FIG. 13.

Preferably, said antibody or antigen-binding fragment thereof further comprises a light chain CDR2 sequence comprising, essentially consisting of, or consisting of the amino acid sequence LMSTRAS (SEQ ID NO: 54), optionally modified wherein 1 or 2 or 3 amino acids are exchanged at position 1, 2, 3, 4, 5, 6, 7, 8, 9 and/or 10 or wherein 1 or 2 or 3 amino acids are deleted at position 1, 2, 3, 4, 5, 6, 7, 8, 9 and/or 10 or wherein 1, 2 or 3 amino acids are added at position 1, 2, 3, 4, 5, 6, 7, 8, 9 and/or 10.

Preferably, said antibody or antigen-binding fragment thereof further comprises a light chain CDR1 sequence comprising, essentially consisting of, or consisting of the amino acid sequence RSSKSLLYKDGKTYLN (SEQ ID NO: 55), modified wherein 1 or 2 or 3 amino acids are exchanged at position 1, 2, 3, 4, 5, 6, 7, 8, 9, 10, 11, 12, 13, 14, 15 and/or 16 wherein 1 or 2 or 3 amino acids are deleted at position 1, 2, 3, 4, 5, 6, 7, 8, 9, 10, 11, 12, 13, 14, 15 and/or 16 or wherein 1, 2 or 3 amino acids are added at position 1, 2, 3, 4, 5, 6, 7, 8, 9, 10, 11, 12, 13, 14, 15 and/or 16.

Preferably, the antibody or antigen-binding fragment thereof comprises within its light chain variable region the above outlined light chain CDRs: CDR3; CDR3 and CDR2; CDR3 and CDR1; or CDR3, CDR2, and CDR1. In each case it is preferred that the one or more CDRs are flanked by one or more of the light chain framework regions as set out in FIG. 13.

In yet another preferred embodiment the heavy chain CDR2 of said antibody or antigen-binding fragment comprises, essentially consists of, or consists of the amino acid sequence EX$_4$LPGSGX$_5$TKYNEX$_6$FX$_7$G (SEQ ID NO: 56), wherein X$_4$ is any amino acid, preferably an aliphatic or polar amino acid, more preferably a hydrophobic or polar uncharged amino acid, most preferably I or N; X$_5$ is any amino acid, preferably a polar amino acid, more preferably a polar uncharged amino acid, most preferably S or T; X$_6$ is any amino acid, preferably an aliphatic amino acid, more preferably N or K; and X$_7$ is any amino acid, preferably an aliphatic or aromatic amino acid, more preferably R or K; and wherein said amino acid sequence optionally comprises 1, 2 or 3 amino acid exchanges outside X$_4$, X$_5$, X$_6$, and X$_7$, and/or 1, 2 or 3 amino acid deletions. Preferably, said antibody or antigen-binding fragment thereof comprises, essentially consists of, or consists of the amino acid sequence SEQ ID NO: 56, optionally modified wherein 1 or 2 or 3 amino acids are exchanged at position 1, 3, 4, 5, 6, 7, 9,10, 11, 12, 13, 15 and/or 17 or wherein 1 or 2 or 3 amino acids are deleted at position 1, 3, 4, 5, 6, 7, 9,10, 11, 12, 13, 15 and/or 17; and/or wherein X$_4$ is selected from the group A, R, N, D, C, Q, E, I, L, M, K, S, T, and V; X$_5$ is selected from the group R, N, D, C, Q, E, K, S, and T; X$_6$ is selected from the group A, R, N, D, C, Q, E, G, H, I, L, K, M, F, S, T, W, Y, and V; X$_7$ is selected from the group A, R, N, D, C, Q, E, G, H, I, L, K, M, F, S, T, W, Y, and V; and more preferably the heavy chain CDR2 comprises, essentially consists of, or consists of the following amino acid sequences: EILPGSGSTKYNENFRG (SEQ ID NO: 72), ENLPGSGSTKYNEKFKG (SEQ ID NO: 73), ENLPGSGTTKYNENFRG (SEQ ID NO: 74), EILPGSGSTKYNENFKG (SEQ ID NO: 75), EILPGSGTTKYNENFRG (SEQ ID NO: 76), ENLPGSGTTKYNEKFKG (SEQ ID NO: 77), ENLPGSGTTKYNENFKG (SEQ ID NO: 78).

In a further embodiment it is preferred that the heavy chain of said antibody or antigen-binding fragment thereof comprises a heavy chain CDR3, CDR2 and CDR1.

Preferably, the heavy chain of the CDR3 sequence comprises, essentially consists of, or consists of the amino acid sequence GDX$_1$X$_2$NSHFX$_3$Y (SEQ ID NO: 50), modified wherein 1 or 2 or 3 amino acids are exchanged at position 1, 2, 5, 6, 7, 8 and/or 10 or wherein 1 or 2 or 3 amino acids are deleted at position 1, 2, 5, 6, 7, 8 and/or 10 or wherein 1, 2 or 3 amino acids are added at 1, 2, 5, 6, 7, 8 and/or 10 or wherein X$_1$ is selected from the group W or Y or F; and/or X$_2$ is selected from the group R, N, D, C, Q, E, K, S, and T; and/or X$_3$ is selected from the group A, R, N, D, C, Q, E, I, L, M, K, S, T, and V; more preferably the heavy chain CDR3 comprises, essentially consists of, or consists of the following amino acid sequences: GDYSNSHFAY (SEQ ID NO: 57) or GDFTNSHFTY (SEQ ID NO: 58) or GDYSNSHFTY (SEQ ID NO: 59) or GDFTNSHFAY (SEQ ID NO: 60) or GDFSNSHFTY (SEQ ID NO: 61) or GDFSNSHFAY (SEQ ID NO: 62) or GDYTNSHFAY (SEQ ID NO: 63); and/or a heavy chain CDR2 sequence comprising, essentially consisting of, or consisting of the amino acid sequence EX$_4$LPGSGX$_5$TK (SEQ ID NO: 51), modified wherein 1 or 2 or 3 amino acids are exchanged at position 1, 3, 4, 5, 6, 7, 9 and/or 10 or wherein 1 or 2 or 3 amino acids are deleted at position 1, 3, 4, 5, 7, 9 and/or 10 or wherein 1, 2 or 3 amino acids are added at position 1, 3, 4, 5, 7, 9 and/or 10; wherein X$_8$ is preferably selected from the group R, N, D, C, Q, E, K, S, and T; X$_9$ is selected from the group A, R, N, D, C, Q, E, I, L, M, K, S, T, and V; more preferably the heavy chain CDR2 comprises, essentially consists, or consists of the following amino acid sequences: EILPGSGSTK (SEQ ID NO: 64) or ENLPGSGSTK (SEQ ID NO: 65) or ENLPGSGTTK (SEQ ID NO: 66) or EILPGSGTTK (SEQ ID NO: 67); or the heavy chain CDR2 of said antibody or antigen-binding fragment comprises, essentially consists of, or consists of the amino acid sequence EX$_4$LPGSGX$_5$TKYNEX$_6$FX$_7$G (SEQ ID NO: 56), wherein X$_4$ is any amino acid, preferably an aliphatic amino acid, more preferably I or N; X$_5$ is any amino acid, preferably an aliphatic or polar amino acid, more preferably S or T; X$_6$ is any amino acid, preferably an aliphatic or aromatic amino acid, more preferably N or K; X$_7$ is any amino acid, preferably an aliphatic or aromatic amino acid, more preferably R or K and wherein said amino acid sequence optionally comprises 1, 2 or 3 amino acid exchanges outside X$_4$, X$_5$, X$_6$, and X$_7$ and/or 1, 2 or 3 amino acid deletions. Preferably said antibody or antigen-binding fragment thereof comprises, essentially consists of, or consists of the amino acid sequence EX$_4$LPGSGX$_5$TKYNEX$_6$FX$_7$G (SEQ ID NO: 56) optionally modified wherein 1 or 2 or 3 amino acids are exchanged at position 1, 3, 4, 5, 6, 7, 9, 10, 11, 12, 13, 15 and/or 17; and/or wherein 1 or 2 or 3 amino acids are deleted at position 1, 3, 4, 5, 6, 7, 9, 10, 11, 12, 13, 15 and/or 17; and/or wherein 1, 2 or 3 amino acids are added at position 1, 3, 4, 5, 6, 7, 9,10, 11, 12, 13, 15 and/or 17, wherein X$_4$ is preferably selected from the group A, R, N, D, C, Q, E, I, L, M, K, S, T, and V; X$_5$ is selected from the group R, N, D, C, Q, E, K, S, and T; X$_6$ is selected from the group A, R, N, D, C, Q, E, G, H, I, L, K, M, F, S, T, W, Y, and V; X$_7$ is selected from the group A, R, N, D, C, Q, E, G, H, I, L, K, M, F, S, T, W, Y, and V; more preferably the heavy chain CDR2 comprises the following amino acid sequences: EILPGSGSTKYNENFRG (SEQ ID NO: 72), ENLPGSGSTKYNEKFKG (SEQ ID NO: 73), ENLPGSGTTKYNENFRG (SEQ ID NO: 74), EILPGSGSTKYNENFKG (SEQ ID NO: 75), EILPGSGTTKYNENFRG (SEQ ID NO: 76), ENLPGSGTTKYNEKFKG (SEQ ID NO: 77), ENLPGSGTTKYNENFKG (SEQ ID NO: 78) and a heavy chain CDR1 sequence comprising, essentially consisting of, or consisting of amino acid sequence GYX$_8$FX$_9$GYWIE (SEQ ID NO: 52), optionally modified wherein 1 or 2 or 3 amino acids are exchanged at position 1, 2, 4, 6, 7, 8, 9 and/or 10; and/or wherein 1 or 2 or 3 amino acids are deleted at position 1, 2, 4, 6, 7, 8, 9 and/or 10; and/or wherein 1, 2 or 3 amino acids are added at position 1, 2, 4, 6, 7, 8, 9 and/or 10; wherein X$_8$ is preferably selected from the group R, N, D, C, Q, E, K, S, and T; X$_9$ is preferably selected from the group A, R, N, D, C, Q, E, I, L, M, K, S, T, and V; more preferably the heavy chain CDR1 comprises, essentially consists of, or consists of the following amino acid sequences: GYTFTGYWIE (SEQ ID NO: 68) or GYKFIGYWIE (SEQ ID NO: 69) or GYKFTGYWIE (SEQ ID NO: 70) or GYTFIGYWIE (SEQ ID NO: 71).

In a further embodiment it is preferred that the light chain of said antibody or antigen-binding fragment thereof comprises a light chain CDR3, CDR2, and CDR1. More preferably, said antibody or antigen-binding fragment thereof comprises a light chain CDR3 sequence comprising the amino acid sequence QQLVEYPLT (SEQ ID NO: 53), optionally modified wherein 1 or 2 or 3 amino acids are exchanged at position 1, 2, 3, 4, 5, 6, 7, 8 and/or 9; and/or wherein 1 or 2 or 3 amino acids are deleted at position 1, 2, 3, 4, 5, 6, 7, 8, and/or 9; and/or wherein 1, 2 or 3 amino acids are added at position 1, 2, 3, 4, 5, 6, 7, 8, and/or 9 and a light chain CDR2 sequence comprising the amino acid sequence LMSTRAS (SEQ ID NO: 54), optionally modified wherein 1 or 2 or 3 amino acids are exchanged at position 1, 2, 3, 4, 5, 6 and/or 7; and/or wherein 1 or 2 or 3 amino acids are deleted at position 1, 2, 3, 4, 5, 6, and/or 7; and/or wherein 1, 2 or 3 amino acids are added at position 1, 2, 3, 4, 5, 6 and/or 7 and a light chain CDR1 sequence comprising, essentially consisting of, or consisting of the amino acid sequence RSSKSLLYKDGKTYLN (SEQ ID NO: 55), optionally modified wherein 1 or 2 or 3 amino acids are exchanged at position 1, 2, 3, 4, 5, 6, 7, 8, 9, 10, 11, 12, 13, 14, 15 and/or 16 or wherein 1 or 2 or 3 amino acids are deleted at position 1, 2, 3, 4, 5, 6, 7, 8, 9, 10, 11, 12, 13, 14, 15 and/or 16 or wherein 1, 2 or 3 amino acids are added at position 1, 2, 3, 4, 5, 6, 7, 8, 9, 10, 11, 12, 13, 14, 15 and/or 16.

In a preferred embodiment the light chain comprises a CDR3 sequence comprising, essentially consisting of, or consisting of the amino acid sequence QQLVEYPLT (SEQ ID NO: 53); a light chain CDR2 sequence comprising essentially consisting of, or consisting of the amino acid sequence LMSTRAS (SEQ ID NO: 54) and a light chain CDR1 sequence comprising, essentially consisting of, or consisting of the amino acid sequence RSSKSLLYKDGKTYLN (SEQ ID NO: 55).

It is also preferred that the heavy chain comprises a CDR3 sequence comprising, essentially consisting of, or consisting of the amino acid sequence GDFTNSHFAY (SEQ ID NO: 60); a heavy chain CDR2 sequence comprising essentially consisting of, or consisting of the amino acid sequence EILPGSGSTK (SEQ ID NO: 64) and a heavy chain CDR1 sequence comprising, essentially consisting of, or consisting of the amino acid sequence GYTFTGYWIE (SEQ ID NO: 68), preferably this antibody comprises one or more, most preferably all of the framework regions of the antibody GA 1A12;

or the heavy chain comprises a CDR3 sequence comprising, essentially consisting of, or consisting of the amino acid sequence GDYSNSHFAY (SEQ ID NO: 57); a heavy chain CDR2 sequence comprising essentially consisting of, or consisting of the amino acid sequence ENLPGSGSTK (SEQ ID NO: 65) and a heavy chain CDR1 sequence comprising, essentially consisting, or consisting of the amino acid sequence GYTFTGYWIE (SEQ ID NO: 68), preferably this antibody comprises one or more, most preferably all of the framework regions of the antibody GA 5E9;

or the heavy chain comprises a CDR3 sequence comprising, essentially consisting of, or consisting of the amino acid sequence GDYSNSHFTY (SEQ ID NO: 59); a heavy chain CDR2 sequence comprising essentially consisting of, or consisting of the amino acid sequence ENLPGSGTTK (SEQ ID NO: 67) and a heavy chain CDR1 sequence comprising, essentially consisting of, or consisting of the amino acid sequence GYKFIGYWIE (SEQ ID NO: 69), preferably this antibody comprises one or more, most preferably all of the framework regions of the antibody GA 5F2.

In still another embodiment, the invention provides an antibody, or an antigen-binding fragment thereof, with a light chain variable region (LCVR) comprising, consisting essentially of or consisting of the amino acid sequence of SEQ ID NO: 80 and a heavy chain variable region (HCVR) comprising consisting essentially of or consisting of the amino acid sequence selected from the group of SEQ ID NOs: 80, 81, and 82.

In preferred embodiments of the fourth aspect, said antibody or antigen-binding fragment specifically binds to the (Gly-Ala)$_a$ polypeptide according to the second and third aspect with a K$_d$ value of 10 nM or less, preferably 9 nM or less, more preferably 8 nM or less, more preferably 7 nM or less, more preferably 6 nM or less, more preferably 5 nM or less, more preferably 4 nM or less, more preferably 3 nM or less, more preferably 2 nM or less, and even more preferably 1 nM or less.

In embodiments wherein the ligand binds to an RNA molecule encoding a polypeptide according to the second and/or third aspect of the present invention it is preferred that the ligand is an oligonucleotide, preferably an oligonucleotide having a nucleotide sequence which is complementary to the sequence of the RNA molecule encoding a polypeptide according to the second and/or third aspect of the present invention.

In preferred embodiments, a detectable tag is attached, preferably covalently bound, to the ligand. Suitable tags are preferably selected from the group consisting of a fluorophore, a chromophore, a radiolabel, a metal colloid, an enzyme, and a chemiluminescent or a bioluminescent molecule. It is particularly preferred that the detectable tag is a fluorophore, preferably GFP, or an enzyme, preferably a luciferase.

In a fifth aspect the present invention provides a method of identifying an inhibitor of expression of a polypeptide comprising or consisting of dipeptide-repeats, comprising the steps of:
(i) providing a cell comprising a polynucleotide sequence encoding said polypeptide,
(ii) contacting the cell with a potential inhibitor of expression of said polypeptide, and
(iii) detecting expression of said polypeptide,
wherein the reduction of expression in comparison to a control cell not contacted with the potential inhibitor indicates that the potential inhibitor inhibits expression of said polypeptide.

In preferred embodiments, the cell provided in step (i) is a prokaryotic or eukaryotic cell, more preferably selected from the group consisting of a bacterial cell, yeast cell, isolated primary cell or cell line. Preferably the isolated primary cell or the cell line is mammalian derived, more preferably human derived.

Preferably said polynucleotide comprises a hexanucleotide repeat, more preferably having a sequence selected from the group consisting of GGGGCC and GGCCTG with genomic flanking regions from human C9orf72 or NOP56, respectively.

In preferred embodiments, said cell comprises said polynucleotide, preferably comprising said hexanucleotide repeats, in its genome, preferably in the first intron of C9orf72 and/or NOP56. In further embodiments said cell comprises said polynucleotide, preferably comprising said hexanucleotide repeats, outside its genome, preferably comprised in a vector, preferably comprised in an intron or exon of said vector. Preferably said vector allows for the expression of the polynucleotide in the cell, i.e., said vector may further comprise regulatory elements such as promoters, enhancers and the like, and optionally also one or more selection markers allowing for the selection, identification, and/or isolation of cells comprising the vector over cells not comprising the vector. The hexanucleotide repeat is present in a number that corresponds to the number of hexanucleotide repeats characteristic of the diseased state. For methods aiming to identify an inhibitor of expression of the hexanucleotide repeats responsible for ALS, FTD, or ALS-FTD, the hexanucleotide is (GGGGCC)$_n$ or the reverse complementary hexanucleotide in the complementary strand (GGCCCC)$_n$ and the number "n" is at least 35, 40, 45, 50, 60, 70, 80, 90, 100, 110, 120, 130, 140, 150, 160, 170, 180, 190, 200, 250, 300, 350, 400, 450, and 500 or more. For methods aiming to identify an inhibitor of expression of the hexanucleotide repeats responsible for SCA36, the hexanucleotide is (GGCCTG)$_n$ or the hexanucleotide in the complementary strand (CAGGCC)$_n$ and the number "n" is at least 20, 25, 30, 35, 40, 45, 50, 60, 70, 80, 90, 100, 110, 120, 130, 140, 150, 160, 170, 180, 190, 200, 250, 300, 350, 400, 450, and 500 or more.

In preferred embodiments, the expression of the polypeptide is detected by a biotechnological method described above, preferably selected from the group consisting of RT-PCR, quantitative real-time PCR, competitive RT-PCR, Southern blotting, NPA, Western blot, ELISA, FACS, and immunocytochemistry (e.g., via fluorescence microscopy or electron microscopy), or any other method known to the skilled artisan.

The polypeptide used in this aspect of the invention is identical to the polypeptide of the second or third aspect described above.

Preferably, the expression of the polypeptide is reduced by at least 10%, more preferably by at least 20%, more preferably by at least 30%, more preferably by at least 40% and even more preferably by at least 50% or more.

The present inventors have discovered that the following proteins specifically bind to RNA comprising (GGGGCC)$_n$ repeats. It is, therefore, credible that the binding of these proteins to the RNA comprising (GGGGCC)$_n$ repeats has a role in the expression of polypeptides comprising or consisting of dipeptide-repeats. Accordingly, the inhibitor may interfere with the expression, preferably translation of hnRNP A2/B, hnRNP A3, p62, SFPQ, SF3B3, ELAV1, ILF3, NONO, HNRPR, ROA3, HNRPL, SAFB1, IF2B1, SAFB2, ROA1, DSRAD, DHX15, ILF2, DHX30, HNRPK, DDX21, or FUS or, alternatively, with the interaction between these proteins and the RNA comprising (GGGGCC)$_n$ repeats or may be a ligand specifically binding to one of these proteins.

In a sixth aspect the present invention provides a method of identifying an inhibitor of the toxic effect of a polypeptide comprising or consisting of dipeptide-repeats, comprising the steps of:
(i) providing a cell comprising a polynucleotide sequence encoding said polypeptide,
(ii) contacting the cell with a potential inhibitor of the toxic effect of said polypeptide, and
(iii) detecting the toxic effect of said polypeptide,
wherein the reduction of the toxic effect in comparison to a control cell not contacted with the potential inhibitor indicates that the potential inhibitor inhibits the toxic effect of said polypeptide.

In preferred embodiments, the cell provided in step (i) is a prokaryotic or eukaryotic cell, more preferably selected from the group consisting of a bacterial cell, yeast cell, isolated primary cell or cell line. Preferably the isolated primary cell or the cell line is mammalian derived, more preferably a human derived cell.

Preferably said polynucleotide comprises a hexanucleotide repeat, more preferably having a sequence selected from the group consisting of GGGGCC and GGCCTG.

In preferred embodiments, said cell comprises said polynucleotide, preferably comprising said hexanucleotide repeats, in its genome, preferably in the first intron of C9orf72 and/or NOP56. In further embodiments said cell comprises said polynucleotide, preferably comprising said hexanucleotide repeats, outside its genome, preferably comprised in a vector, preferably comprised in an intron or exon of said vector. Preferably said vector allows for the expression of the polynucleotide in the cell, i.e., said vector may further comprise regulatory elements such as promoters, enhancers and the like, and optionally also one or more selection markers allowing for the selection, identification, and/or isolation of cells comprising the vector over cells not comprising the vector. The hexanucleotide repeat is present in a number that corresponds to the number of hexanucleotide repeats characteristic of the diseased state. For methods aiming to identify an inhibitor of the toxic effect of the polypeptide encoded by the hexanucleotide repeats responsible for ALS, FTD or ALS-FTD, the hexanucleotide is $(GGGGCC)_n$ and the number "n" is at least 35, 40, 45, 50, 60, 70, 80, 90, 100, 110, 120, 130, 140, 150, 160, 170, 180, 190, 200, 250, 300, 350, 400, 450, and 500 or more. For methods aiming to identify an inhibitor of the toxic effect of the polypeptide encoded by the hexanucleotide repeats responsible for SCA36, the hexanucleotide is $(GGCCTG)_n$ and the number "n" is at least 35, 40, 45, 50, 60, 70, 80, 90, 100, 110, 120, 130, 140, 150, 160, 170, 180, 190, 200, 250, 300, 350, 400, 450, and 500 or more.

In preferred embodiments, the toxic effect of the polypeptide is detected by a biotechnological method described above, preferably selected from the group consisting of MTT assay, LDH assay, or any other method known to the skilled artisan.

The polypeptide used in this aspect of the invention is identical to the polypeptide of the second or third aspect described above.

Preferably, the expression of the polypeptide is reduced by at least 10%, more preferably by at least 20%, more preferably by at least 30%, more preferably by at least 40% and even more preferably by at least 50% or more.

In a seventh aspect the present invention provides a method of identifying an inhibitor of the formation of aggregates comprising a polypeptide comprising or consisting of dipeptide-repeats, comprising the steps of:
(i) providing a cell expressing a polynucleotide sequence encoding said polypeptide or a cell free system comprising said polypeptide,
(ii) contacting the cell or the cell free system with a potential inhibitor of formation of aggregates of said polypeptide, and
(iii) detecting formation of aggregates of said polypeptide, wherein the reduction of formation of aggregates in comparison to a control cell or cell free system not contacted with the potential inhibitor indicates that the potential inhibitor inhibits formation of aggregates.

In preferred embodiments, the cell provided in step (i) is a prokaryotic or eukaryotic cell, more preferably selected from the group consisting of a bacterial cell, yeast cell, isolated primary cell or cell line. Preferably the isolated primary cell or the cell line is mammalian derived.

Preferably, said polynucleotide comprises a hexanucleotide repeat, more preferably having a sequence selected from the group consisting of GGGGCC and GGCCTG. The hexanucleotide repeat is present in a number that corresponds to the number of hexanucleotide repeats characteristic of the diseased state. For methods aiming to identify an inhibitor of the formation of aggregates responsible for ALS, FTD, or ALS-FTD, the hexanucleotide is $(GGGGCC)_n$ and the number "n" is at least 35, 40, 45, 50, 60, 70, 80, 90, 100, 110, 120, 130, 140, 150, 160, 170, 180, 190, 200, 250, 300, 350, 400, 450, and 500 or more. For methods aiming to identify an inhibitor of the formation of aggregates responsible for SCA36, the hexanucleotide is $(GGCCTG)_n$ and the number "n" is at least 35, 40, 45, 50, 60, 70, 80, 90, 100, 110, 120, 130, 140, 150, 160, 170, 180, 190, 200, 250, 300, 350, 400, 450, and 500 or more.

In preferred embodiments, said cell comprises said polynucleotide, preferably comprising said hexanucleotide repeats, in its genome, preferably in the first intron of C9orf72 and/or NOP56. In further embodiments said cell comprises said polynucleotide, preferably comprising said hexanucleotide repeats, outside its genome, preferably comprised in a vector, preferably comprised in an intron or exon of said vector. Preferably said vector allows for the expression of the polynucleotide in the cell, i.e., said vector may further comprise regulatory elements such as promoters, enhancers and the like, and optionally also one or more selection marker allowing for the selection, identification, and/or isolation of cells comprising the vector over cells not comprising the vector. In embodiments wherein a cell-free system is used, it is preferred that said cell-free system comprises one or more of the subcellular fractions selected from the list consisting of nucleoli, nucleus, ribosome, endoplasmatic reticulum, and Golgi apparatus. In alternative embodiments a cell-free expression system is used to identify an inhibitor of the formation of aggregates.

In preferred embodiments, the formation of aggregates is detected by a biotechnological method, preferably selected from the group consisting of filter trap assay, Western blot, size-exclusion chromatography (e.g., gel-filtration chromatography or gel permeation chromatography), and immunocytochemistry (e.g., via fluorescence microscope or electron microscopy), or any other method known to the skilled artisan or described in the Examples section.

Preferably, formation of aggregates is reduced by at least 10%, more preferably by at least 20%, more preferably by at least 30%, more preferably by at least 40% and even more preferably by at least 50% or more.

In further preferred embodiments, the inhibitor is selected from the group consisting of hexanucleotide-specific siRNA, the ligand of the fourth aspect of the present invention, hnRNP A3 and p62.

In further preferred embodiments, additional compounds may be provided which may be involved in the formation of aggregates such as compounds binding to or forming complexes with said polypeptide. In preferred embodiments, the additional compound is selected from the group consisting of hippuristanol and a small molecule inhibitor of the eIF4A helicase.

The polypeptide used in this aspect of the invention is identical to the polypeptide of the second or third aspect described above.

In an eighth aspect the present invention provides an inhibitor of the expression of a polypeptide comprising dipeptide-repeats, an inhibitor of a toxic effect of a polypeptide comprising dipeptide-repeats, or an inhibitor of the formation of aggregates comprising a polypeptide comprising dipeptide-repeats for treating or preventing a disease characterized by an expansion of genomic hexanucleotide repeats.

In preferred embodiments the inhibitor reduces or completely abolishes the expression of the hexanucleotide into the polypeptide comprising dipeptide-repeats. In preferred embodiments, the inhibitor reduces or abolishes the transcription, RNA splicing, translation or protein folding into the polypeptide comprising dipeptide-repeats, preferably by binding to or forming a complex with a factor involved in the expression of said polypeptide, which is subsequently not able to fulfill its function anymore, resulting the prevention of the expression of the polypeptide. Preferably such factor is a transcription factor or an RNA interacting factor. By interacting with said factor, the expression of said polypeptide is reduced or abolished, resulting in a reduction or complete disappearance of signs or symptoms of the disease. Accordingly, in preferred embodiments the inhibitor or a nucleic acid encoding said inhibitor is provided to a healthy individual before the onset of the disease or to a patient having or being suspected of having or being susceptible to said disease in order to treat said disease or to prevent the onset or the progression of the disease, i.e., for prophylactic reasons.

In preferred embodiments, the inhibitor reduces the expression, i.e., the transcription, the RNA splicing and/or the translation, of the polypeptide by at least 10%, more preferably by at least 20%, more preferably by at least 30%, more preferably by at least 40% and even more preferably by at least 50% or more. In further embodiments the inhibitor reduces or completely blocks the toxic effect of the polypeptide comprising dipeptide-repeats and thereby the damage caused by the expression of said polypeptide or the formation of aggregates of said polypeptide, to the cell.

In preferred embodiments the inhibitor reduces the toxic effect of the polypeptide by reducing the damaging effect the polypeptide has on the cell, by activating cellular processes restoring the cell, and/or by activating cellular processes prolonging the cell's viability which was reduced due to the toxic effect of the polypeptide.

Preferably, the inhibitor reduces the toxic effect of the polypeptide by at least 10%, more preferably by at least 20%, more preferably by at least 30%, more preferably by at least 40% and even more preferably by at least 50% or more.

In further embodiments, the inhibitor reduces or completely blocks the accumulation of the polypeptide comprising dipeptide-repeats and thereby the formation of aggregates. In preferred embodiments the inhibitor reduces or completely blocks the accumulation of the polypeptide comprising dipeptide-repeats by effecting or altering the electrostatic interaction properties of said polypeptide, by altering the 3-dimensional structure of the polypeptide or by altering or preventing the 3-dimensional folding of the polypeptide after translation. Preferably, the inhibitor reduces the formation of aggregates by at least 10%, more preferably by at least 20%, more preferably by at least 30%, more preferably by at least 40% and even more preferably by at least 50% or more. In embodiments of the eighth aspect of the present invention, the inhibitor is used to treat or prevent a disease characterized by an expansion of genomic hexanucleotide repeats through administration of said inhibitor or a nucleic acid encoding said inhibitor is administered to a patient having, suspected of having or being susceptible to said disease.

In preferred embodiments, the inhibitor is selected from the group consisting of hexanucleotide specific siRNA, the ligand of the fourth aspect of the present invention, or siRNAs specifically inhibiting expression of hnRNP A2/B, hnRNP A3, p62, SFPQ, SF3B3, ELAV1, ILF3, NONO, HNRPR, ROA3, HNRPL, SAFB1, IF2B1, SAFB2, ROA1, DSRAD, DHX15, ILF2, DHX30, HNRPK, DDX21, or FUS or a ligand specifically binding to these proteins. The skilled person is well aware how to design such siRNAs based on the publicly available nucleic acid sequences encoding these proteins. In preferred embodiments, a detectable tag is attached, preferably covalently bound, to the inhibitor. Suitable tags are preferably selected from the group consisting of a fluorophore, a chromophore, a radiolabel, a metal colloid, an enzyme, and a chemiluminescent or a bioluminescent molecule.

In embodiments of the eighth aspect of the present invention, the inhibitor is used to treat or prevent a disease characterized by an expansion of genomic hexanucleotide repeats through administration of said inhibitor or a nucleic acid encoding said inhibitor to a patient having, suspected of having or being susceptible to said disease.

In preferred embodiments, the patient susceptible to a disease characterized by the expansion of genomic hexanucleotide repeats does not show any symptoms of said disease yet but is vulnerable to the emergence of a disease due to genetic predisposition. In preferred embodiments, the patient suspected of having a disease characterized by the expansion of genomic hexanucleotide repeats shows early signs or symptoms of said disease. In embodiments wherein the patient has a disease characterized by the expansion of genomic hexanucleotide repeats, said patient shows more signs or symptoms or more pronounced signs or symptoms of the disease.

In further preferred embodiments of the eighth aspect of the present invention, the disease characterized by an expansion of hexanucleotide repeats is selected from amyotrophic lateral sclerosis (ALS), frontotemporal dementia (FTD), amyotrophic lateral sclerosis-frontotemporal dementia (ALS-FTD) and spinocerebellar ataxia (SCA36).

In a ninth aspect the present invention provides the polypeptide of the second or third aspect of the present invention, the ligand of the fourth aspect of the present invention, the inhibitor of the eighth aspect of the present invention and/or a nucleotide sequence encoding said polypeptide, said ligand or said inhibitor for use in diagnosis, prophylaxis, or treatment of a disease characterized by an expansion of genomic hexanucleotide repeats.

The nucleic acid encoding said ligand or said inhibitor can only be used in this and the other aspects of the invention, if said ligand or inhibitor is a polypeptide. Accordingly, it is preferred that a nucleic acid is used if the ligand or inhibitor is an antibody, an antigen-binding fragment thereof or an antibody-like protein.

In preferred embodiments the polypeptide of the second or third aspect of the present invention is used for diagnosing a disease characterized by an expansion of genomic hexanucleotide repeats, preferably by detecting said polypeptide in an individual having, suspected of having, or being susceptible to said disease. Preferably, said polypeptide is detected by any of the above described methods, preferably by means of a Western blot, ELISA, FACS, and immunocytochemistry (e.g., via fluorescence microscopy or electron microscopy). In preferred embodiments the detection of the polypeptide of the second or third aspect of the present invention is an indicator of the presence of the disease.

In further preferred embodiments the polypeptide of the second or third aspect of the present invention is used for prophylaxis or treatment of said disease, preferably via immunization, more preferably via passive immunization of the individual or patient. It is preferred that the ligands of the invention, preferably antibodies of the invention or nucleic acids encoding these, are administered to a patient to bind the DPRs formed, to prevent aggregation and to remove the DPRs from the brain. Alternatively, the immune system of the individual/patient is primed/activated/strengthened to react against the polypeptide, i.e., by activating the proliferation of B- or T-cells and/or the production of antibodies directed against said polypeptide.

It is preferred that said polypeptide or a nucleic acid encoding said polypeptide is provided to a healthy individual before the onset of the disease. In further embodiments the polypeptide is provided to a patient having said disease, being suspected of having said disease or being susceptible to said disease in order to treat the disease.

The activation of the immune system may lead to a bettering or complete disappearance of the symptoms and/or cause of the disease. In preferred embodiments the polypeptide is provided to the individual or patient in the form of a vaccine.

In further embodiments the ligand of the fourth aspect of the present invention is used in diagnosing a disease characterized by an expansion of genomic hexanucleotide repeats. For diagnostic purposes the ligand itself may be detected in a sample provided by a patient by any of the methods described above. Alternatively, the ligand, preferably a ligand further comprising a detectable tag, may be used to detect the presence of the polypeptide of the second and third aspect of the present invention, or an mRNA molecule encoding said polypeptide, in the sample from the individual or patient. Suitable tags are preferably selected from the group consisting of a fluorophore, a chromophore, a radiolabel, a metal colloid, an enzyme, and a chemiluminescent or a bioluminescent molecule.

In further embodiments the ligand is for use in the passive and/or active immunization of an individual or a patient.

In preferred embodiments, the ligand of the fourth aspect of the present invention may be used to treat a disease characterized by the expansion of genomic hexanucleotide repeats. In such embodiments the ligand binds to or forms a complex with the polypeptide of the second or third aspect of the present invention, thereby preventing the formation of polypeptide aggregates. Alternatively, the ligand binds to or forms a complex with a factor involved in the expression, i.e., the transcription, RNA splicing or translation, of said polypeptide. Accordingly, it is preferred that said ligand or a nucleic acid encoding said ligand is provided to a healthy individual before the onset of the disease or to a patient having, being suspected of having, or being susceptible to said disease. It is preferred to use the ligand of the fourth aspect of the present invention for passive immunization of an individual or a patient.

In preferred embodiments the ligand of the fourth aspect of the present invention may be used for prophylactic purposes in that it is used to induce an immune response against said ligand thereby also inducing an immune response against the ligand in complex with the polypeptide or the ligand in complex with an mRNA molecule encoding said polypeptide. Accordingly, it is preferred that said ligand or a nucleic acid encoding said ligand is provided to a healthy individual before the onset of the disease or to a patient having or being suspected of having said disease. It is preferred to use the ligand of the fourth aspect of the present invention for active immunization of an individual or a patient.

In further embodiments of the ninth aspect of the present invention, the inhibitor of the eighth aspect of the present invention is for use in treating a patient having or suspected of having a disease characterized by an expansion of genomic hexanucleotide repeats, preferably by passive immunization. In such embodiments the inhibitor binds to or forms a complex with a factor involved in the expression, i.e., the transcription, RNA splicing or translation, of said polypeptide, and thereby prevents the expression of the polypeptide. Accordingly, in preferred embodiments the inhibitor or a nucleic acid encoding said inhibitor is provided to a healthy individual before the onset of the disease or to a patient having or being suspected of having said disease. It is preferred to use the inhibitor of the eighth aspect of the present invention for immunization, preferably passive immunization, of an individual or a patient.

In embodiments wherein said polypeptide, said ligand or said inhibitor is used for immunization, i.e., for active or passive immunization, it is preferred that the individual/patient is provided with a vaccine. In further preferred embodiments the vaccine comprises a vector, preferably comprising one or more nucleic acid sequences encoding said polypeptide, said ligand and/or said inhibitor. Said vector preferably comprises further nucleic acid sequences allowing for the expression of the polypeptide, ligand or inhibitor in a cell, preferably in a cell of the individual or patient.

In a tenth aspect the present invention provides a kit of parts for diagnosing, treating or preventing a disease characterized by an expansion of genomic hexanucleotide repeats, comprising the polypeptide of the second aspect of the present invention, the ligand of the fourth aspect of the present invention, the inhibitor of the eighth aspect of the present invention and/or a nucleotide sequence encoding said polypeptide, said ligand or said inhibitor, and optionally further comprising a container and/or a data carrier, preferably comprising instructions for one or more of the methods of the first, fifth, to seventh sixth aspect of the present invention.

In an eleventh aspect the present invention provides a pharmaceutical comprising the polypeptide of the second aspect of the present invention, the ligand of the fourth aspect of the present invention, the inhibitor of the eighth aspect of the present invention and/or a nucleotide sequence encoding said polypeptide, said ligand or said inhibitor.

In preferred embodiments said pharmaceutical is a vaccine, preferably comprising a vector. In further preferred embodiments said vector comprises one or more nucleic acid sequences encoding said polypeptide, said ligand and/ or said inhibitor. Said vector preferably comprises further nucleic acid sequences allowing for the expression of the polypeptide, ligand or inhibitor in a cell, preferably in a cell of the individual or patient.

In preferred embodiments the pharmaceutical further comprises a pharmaceutically acceptable carrier, excipient and/or adjuvant and optionally one or more additional active substances. The additional active substances may be effective against the same or against a different disease or disorder. Accordingly, additional active substances comprise those having a beneficial effect on the treatment of a disease characterized by an expansion of genomic hexanucleotide repeats. Furthermore, additional active substances may be directed at the treatment of different diseases, disorders or conditions and suitable to be administered in combination with the active ingredient for the treatment of a disease characterized by an expansion of genomic hexanucleotide repeats.

Preferably, the pharmaceutical of the eleventh aspect contains a therapeutically effective amount of said polypeptide, ligand, inhibitor or nucleic acid encoding said polypeptide, ligand, or inhibitor, preferably in purified form, together with a suitable amount of carrier and/or excipient so as to provide the form for proper administration to the patient. The formulation should suit the mode of administration.

The pharmaceutical can take the form of solutions, suspensions, emulsion, tablets, pills, capsules, powders, sustained-release formulations and the like. The pharmaceutical can be formulated as a suppository, with traditional binders and carriers such as triglycerides.

For preparing the pharmaceuticals of the present invention, pharmaceutically acceptable carriers can be either solid or liquid. Solid form compositions include powders, tablets, pills, capsules, lozenges, cachets, suppositories, and dispersible granules. A solid excipient can be one or more substances, which may also act as diluents, flavoring agents, binders, preservatives, tablet disintegrating agents, or encapsulating materials. In powders, the excipient is preferably a finely divided solid, which is in a mixture with the finely divided inhibitor of the present invention. In tablets, the active ingredient is mixed with the carrier having the necessary binding properties in suitable proportions and compacted in the shape and size desired. Suitable excipients are magnesium carbonate, magnesium stearate, talc, sugar, lactose, pectin, dextrin, starch, gelatin, tragacanth, methylcellulose, sodium carboxymethylcellulose, low melting wax, cocoa butter, and the like. For preparing suppositories, a low melting wax, such as a mixture of fatty acid glycerides or cocoa butter, is first melted and the active component is dispersed homogeneously therein, such as by stirring. The molten homogeneous mixture is then poured into convenient sized molds, allowed to cool, and thereby to solidify. Tablets, powders, capsules, pills, cachets, and lozenges can be used as solid dosage forms suitable for oral administration.

Liquid form compositions include solutions, suspensions, and emulsions, for example, water, saline solutions, aqueous dextrose, glycerol solutions or water/propylene glycol solutions. For parenteral injections (e.g., intravenous, intra-arterial, intraosseous infusion, intramuscular, subcutaneous, intraperitoneal, intradermal, and intrathecal injections), liquid preparations can be formulated in solution, e.g., aqueous polyethylene glycol solution. A saline solution is a preferred carrier when the pharmaceutical composition is administered intravenously.

Preferably, the pharmaceutical composition is in unit dosage form. In such form the composition may be subdivided into unit doses containing appropriate quantities of the active component. The unit dosage form can be a packaged composition, the package containing discrete quantities of the composition, such as packaged tablets, capsules, and powders in vials or ampoules. Also, the unit dosage form can be a capsule, an injection vial, a tablet, a cachet, or a lozenge itself, or it can be the appropriate number of any of these in packaged form. The composition, if desired, can also contain minor amounts of wetting or emulsifying agents, or pH buffering agents. In preferred embodiments the pharmaceutical is administered via an administration route selected from the group consisting of intranasal administration, intramuscular administration, subcutaneous administration, oral administration, and topical administration.

In a twelfth aspect the present invention provides the pharmaceutical of the tenth aspect of the present invention for use in diagnosis, prophylaxis, or treatment of a disease characterized by an expansion of genomic hexanucleotide repeats.

In preferred embodiments of the eleventh aspect of the present invention, the disease characterized by an expansion of hexanucleotide repeats is selected from amyotrophic lateral sclerosis (ALS), frontotemporal dementia (FTD), amyotrophic lateral sclerosis-frontotemporal dementia (ALS-FTD) and spinocerebellar ataxia (SCA36).

In the preferred embodiments, the hexanucleotide repeats have a sequence selected from the group consisting of GGGGCC and GGCCTG. Preferably, the hexanucleotide $(GGGGCC)_n$ is responsible for the formation of aggregates responsible for ALS, FTD or ALS-FTD, and the number "n" is at least 35, 40, 45, 50, 60, 70, 80, 90, 100, 110, 120, 130, 140, 150, 160, 170, 180, 190, 200, 250, 300, 350, 400, 450, and 500 or more. In further embodiments the hexanucleotide $(GGCCTG)_n$ is responsible for the formation of aggregates responsible for SCA36, and the number "n" is at least 35, 40, 45, 50, 60, 70, 80, 90, 100, 110, 120, 130, 140, 150, 160, 170, 180, 190, 200, 250, 300, 350, 400, 450, and 500 or more.

In preferred embodiments the pharmaceutical is administered to a healthy individual in order to prevent the onset of the disease or to a patient having, being suspected of having or being susceptible to said disease in order to prevent the progression of the disease or in order to treat said disease.

In preferred embodiments, the pharmaceutical reduces the expression, i.e., the transcription, the RNA splicing and/or the translation, of the polypeptide by at least 10%, more preferably by at least 20%, more preferably by at least 30%, more preferably by at least 40% and even more preferably by at least 50% or more, and thereby treats said disease or prevents the progression or onset of said disease.

Preferably, the pharmaceutical reduces the toxic effect of the polypeptide by at least 10%, more preferably by at least 20%, more preferably by at least 30%, more preferably by at least 40% and even more preferably by at least 50% or more, and thereby treats said disease or prevents the progression or onset of said disease.

Preferably, the pharmaceutical reduces the formation of aggregates by at least 10%, more preferably by at least 20%, more preferably by at least 30%, more preferably by at least 40% and even more preferably by at least 50% or more, and thereby treats said disease or prevents the progression or onset of said disease.

Various modifications and variations of the invention will be apparent to those skilled in the art without departing from the scope of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the relevant fields are intended to be covered by the present invention.

The following examples and figures are merely illustrative of the present invention and should not be construed to limit the scope of the invention as indicated by the appended claims in any way.

EXAMPLES

Example 1—Antibodies

In order to directly detect expression of the postulated repeat proteins, we raised antibodies (anti-GA and anti-GP) against $(GA)_{15}$ and $(GP)_{15}$ peptides fused to maltose binding protein and tested a monoclonal antibody (anti-GR) that was originally raised against an EBNA2A epitope including a $(GR)_6$ repeat (Kremmer et al., 1995).

Rabbits were immunized with MBP-fusion proteins containing either $(GA)_{15}$ or $(GP)_{15}$ repeats at the C-terminus (Eurogentec). The resulting serum was purified with GST-fusion proteins containing either $(GA)_{15}$ or $(GP)_{15}$ at the C-terminus. Briefly E. coli expressed protein was cross-linked to Glutathione Sepharose (Pierce) and bound antibodies were eluted by pH-shift (0.15 M NaCl, 0.1 M glycine pH=2.5) and immediately neutralized (0.1 volume 1 M Tris pH=9.5). Rat monoclonal poly-GR-repeat-specific antibody 5A2 was originally generated against peptide antigen (GQSRGQSRGRGRGRGRGRGKGK; SEQ ID NO: 47) from EBNA2 and detects specifically GST-$(GR)_{15}$ (FIG. 1A) (Kremmer et al., 1995). p62 (mouse, BD Transduction), rabbit TDP (Proteintech) phospho-TDP-43 (Ser409/Ser410, clone 1D3) (Neumann at al., 2009) and rat GST antibody (6G9, Sigma) are commercially available.

All three DPR antibodies detected the respective repeat antigens by immunoblotting without cross-reaction with the other two DPR proteins (FIG. 1A).

Example 2—Hexanucleotide Repeat Constructs

To test whether such repeat proteins can be translated in the absence of a start codon, we cloned the repeat region from C9orf72 patients into a mammalian expression vector using repeat primed PCR.

The hexanucleotide repeat was amplified by repeat primed PCR (6) from patient lymphoblasts (AGTACTCGCTGAGGGTGAAC, SEQ ID NO: 48; and CGTACGC ATCCCAGTTTGAGAGCCCCGGCCCCGGCCCCGGCCCC, SEQ ID NO: 49) and topo-cloned into pEF6-V5/His (Invitrogen). Neither the multiple cloning site nor the C9orf72 genomic sequence contain ATG start codons. Additionally, multiple stop codons are present in all reading frames upstream of the GGGGCC repeat. Plasmids were transformed into Stbl2 bacteria (Invitrogen) that were grown at 32° C. to avoid recombination. Because of the extreme GC-content only ~20 repeats could be sequenced. Higher repeat numbers were therefore estimated by restriction digest (FIG. 1B).

For the longer constructs we could only use restriction digest to estimate the repeat number ranging from ~28 to ~145, because the extreme GC-content precludes sequencing (FIG. 1B, upper panel). The region upstream of the GGGGCC-repeat lacks ATG start codons, and constructed into HEK293 cells (grown with DMEM supplemented with 10% FCS and penicillin/streptomycin), anti-GA antibodies detected proteins of increasing size starting with a faint product from ~38 repeats, suggesting that the translation mechanism requires a minimal repeat length (FIG. 1B, arrow). Nevertheless, we cannot exclude translation of shorter polypeptides that were not detected due to rapid degradation or a lower number of repeat epitopes. We did not detect poly-GR products (data not shown) and only the longest construct with ~145 repeats additionally expressed detectable amounts of poly-GP (FIG. 1B). Together these data indicate that medium-length GGGGCC-repeats are predominantly translated into poly-GA and lesser amounts of poly-GP proteins in HEK293 cells (FIG. 1B).

Example 3—Filter Trap Assay

To analyze poly-GA aggregation we performed filter trap assays from human post-mortem cerebella of healthy controls and FTLD/ALS-TDP patients with and without the C9orf72 hexanucleotide repeat expansion. This method is well established for the study of poly-Q aggregation (Li et al., 2003).

Patient material was provided by the Neurobiobank Munich, Ludwig-Maximilians-University Munich and the Antwerp Bio Bank at the Institute Born-Bunge, University of Antwerp and was collected and distributed according to the guidelines of the local ethical committees.

Cerebellum was homogenized in PBS containing 1% Triton-X 100, 15 mM $MgCl_2$ and 0.2 mg/ml DNase I. Upon centrifugation (180,000 g for 30 min at 12° C.) the insoluble pellet was resuspended in 2% SDS 100 mM Tris pH=7 and incubated at room temperature for 1 h and then filtered through a cellulose acetate membrane with 0.2 µm pore size (Li et al., 2003).

We observed a strong poly-GA signal only in FTLD/ALS patients with hexanucleotide repeat expansion (FIG. 1C), indicating that poly-GA forms SDS-insoluble aggregates in the cerebellum. Additionally, we also detected insoluble poly-GP and poly-GR in C9orf72 patients (FIG. 1C). The 2% SDS-insoluble material was partially solubilized upon boiling in 8% SDS and could be analyzed via SDS-PAGE. All three DPR-specific antibodies detected high-molecular weight aggregates at the top of the gel in C9orf72 mutation carriers, but not in controls (FIG. 1D). These findings indicate that aggregating DPR proteins are generated in all three reading frames, specifically in patients with C9orf72 mutations.

Example 4—Immunostaining

Paraffin-embedded sections were first deparaffinized with xylene and ethanol. After brief wash with deionized water, antigen retrieval was performed by microwaving sections six times 3 min in 100 mM citrate buffer (pH 6.0). Sections were allowed to settle for 20 min followed by a brief wash with deionized water. Endogenous peroxidase was blocked with 5% $H_2O_2$ in methanol for 16 min. After rinse with deionized water, sections were settled in PBS with 0.05% Brij35. Blocking was performed with 2% FCS in PBS for 5 min. Primary antibodies were diluted with blocking solution and incubated overnight at 4° C. For the rat monoclonal antibodies 5A2 and 1D3, rabbit anti-rat secondary antibody (PARIS Anticorps) was additionally used at 1:2000 dilution for 1 h. Sections were washed two times with PBS with 0.05% Brij35 for 5 min and developed with IHC-Kit DCS SuperVision 2 HRP (DCS) or NovoLink Polymer Detection System for rat antibodies (Leica) using DAB as chromogen. Microscopic images were obtained with a BX50 microscope and Cell-D software (Olympus). For immunofluorescence species specific secondary antibodies conjugated with Alexa-488 or Alexa-544 (Invitrogen) were used for double staining. TOPRO-3 (Invitrogen) was used as nuclear stain. Autofluorescence was reduced with 0.3% Sudan Black. Confocal images were obtained with LSM510 (Zeiss) with a 63×/1.4 oil immersion lens, using a pinhole diameter of 1 Airy unit. Brightness and contrast of each image were linearly enhanced using LSM software (Zeiss).

Example 5—Cellular Distribution Patterns of the DPR Proteins

Figure 3:
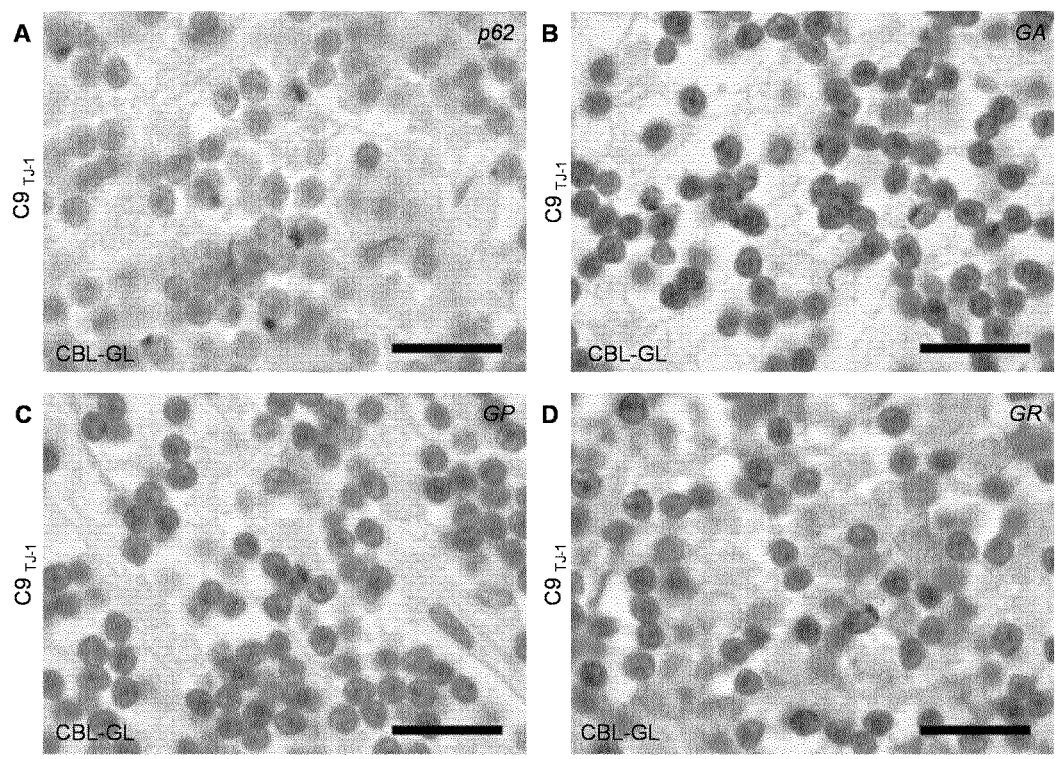
FIG. 3: Overview of DPR pathology in the cerebellum. Immunohistochemistry in the cerebellar granular layer comparing inclusions stained with p62, poly-GA, poly-GP and poly-GR specific antibodies in an FTLD/ALS patient with C9orf72 mutation (TJ-1). The number of p62-positive aggregates (A) is similar to the number of poly-GA aggregates (B), whereas poly-GP and poly-GR aggregates are less frequent (C, D). In patients and controls poly-GR antibodies additionally showed faint nuclear and cytoplasmic staining, probably due to cross-reactivity with natural short Gly-Arg repeats present in several DNA/RNA-binding proteins. Scale bars denote 20 µm. CBL-GL cerebellar granular layer.
Figure 4:
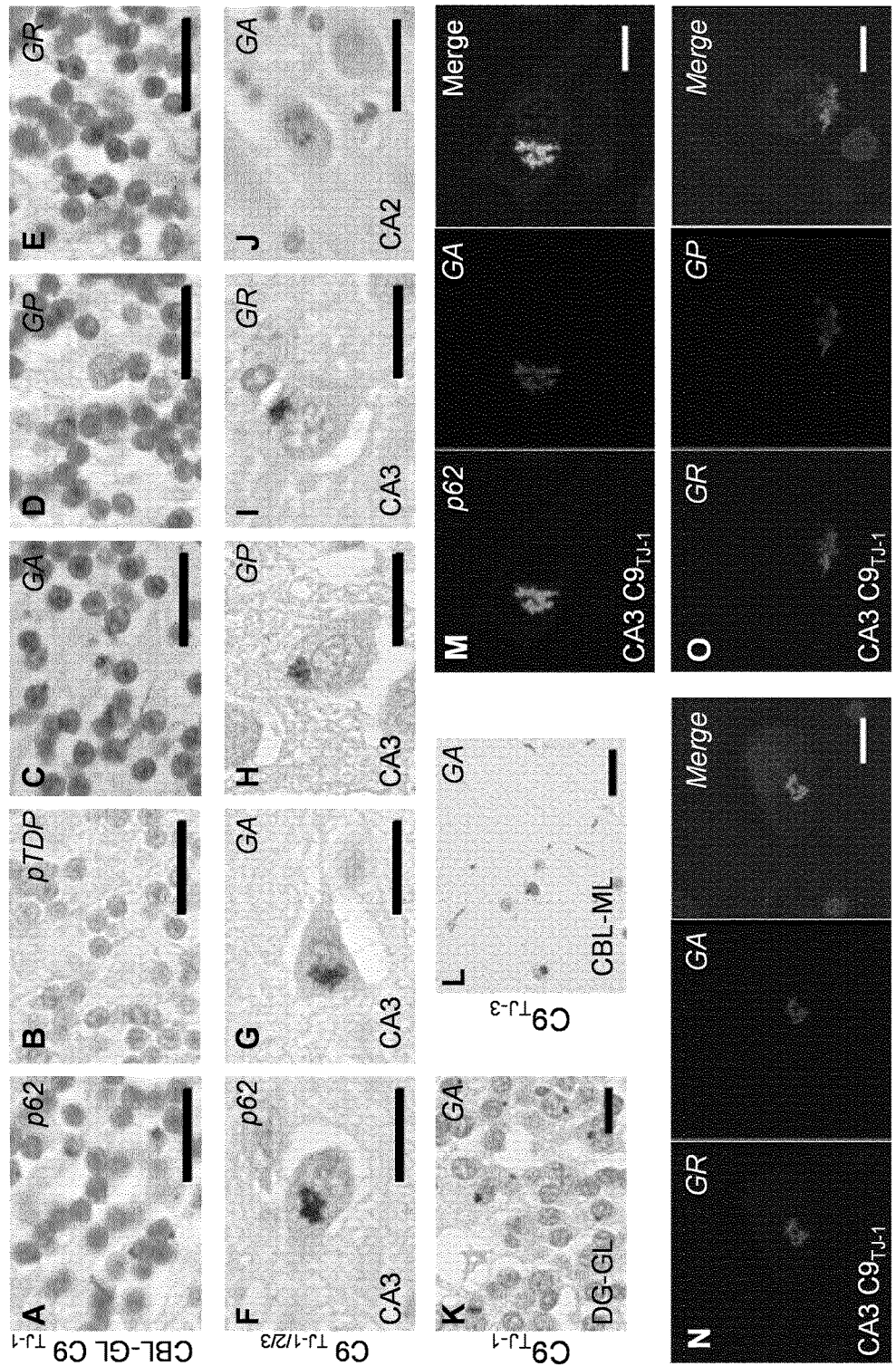
FIG. 4: DPR proteins form the characteristic TDP-43-negative inclusions in C9orf72 patients. Immunohistochemistry with DPR-specific antibodies (GA, GP, GR) reveals poly-GA, poly-GP and poly-GR inclusions resembling the p62-positive aggregates in FTLD/ALS patients with C9orf72 mutation (compare FIG. 2). Dot-like and thread-like inclusions in cerebellar granular layer (CBL-GL) (A-E). Star-shaped cytoplasmic (F-I) and dot-like intranuclear (J) inclusions in hippocampal cornu ammonis regions 2 and 3 (CA2 and CA3). Inclusion of mixed morphology in cerebellar molecular layer (CBL-ML) and dentate gyrus granular layer (DG-GL) (K, L). Note that in patients and controls poly-GR antibodies additionally showed faint nuclear and cytoplasmic staining. Scale bars denote 20 µm. Anti-GA and anti-GP specificity was confirmed by preincubation experiments with recombinant antigens (FIGS. 5A-F). Validation of anti-GR was only possible by immunoblot experiments (FIG. 1A), because the poly-GR antigen itself bound to the tissue directly (FIGS. 5G-K). (M-O) Double immunofluorescence reveals composition of DPR-aggregates in C9orf72 FTLD/ALS patient TJ-1. No colocalization of DPR-proteins was observed with phospho-TDP-43 (see FIG. 6). Scale bars denote 10 µm.
Figure 5:
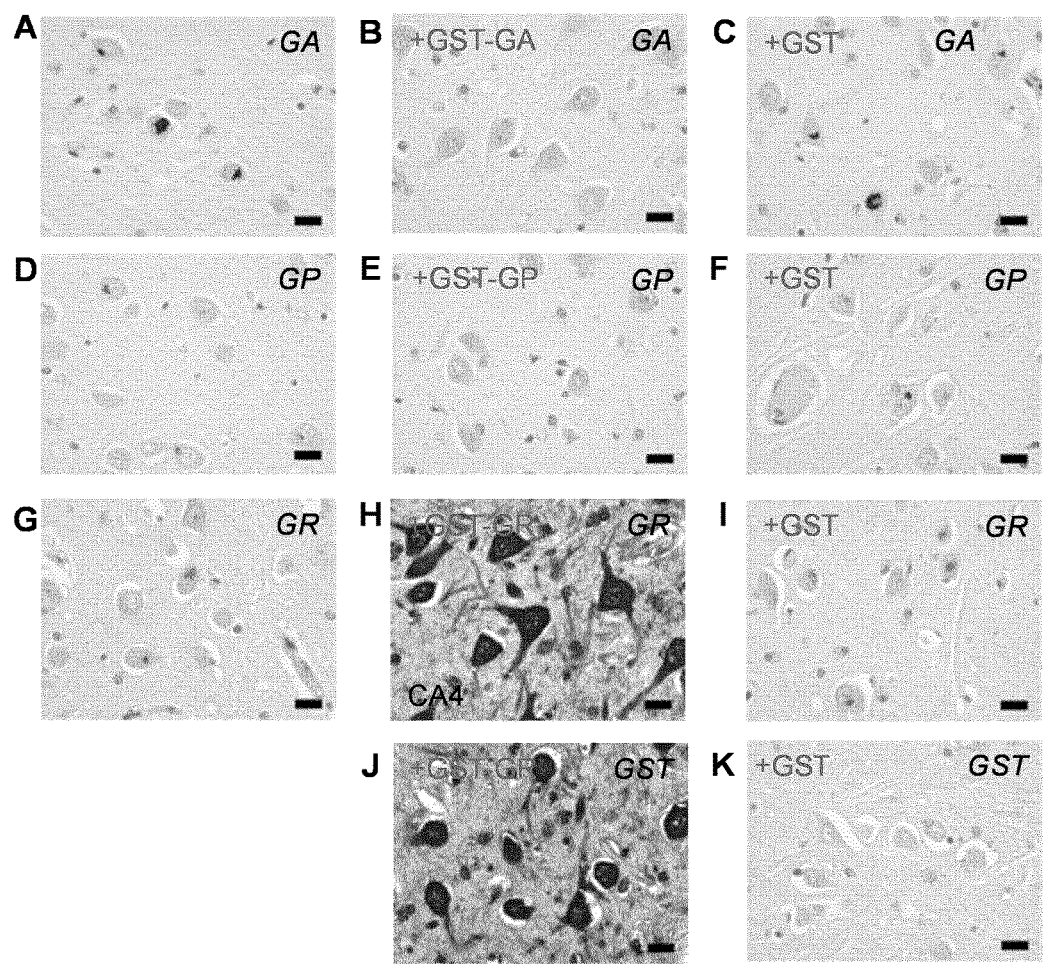
FIG. 5: Preincubation with poly-(Gly-Ala) and poly-(Gly-Pro) antigens confirms the specificity of anti-GA and anti-GP antibodies. Immunohistochemistry in the hippocampal CA4 region of C9orf72 mutation case TJ-1 stained with antibodies against poly-GA, poly-GP and poly-GR preincubated with GST-(GA)$_{15}$, GST-(GP)$_{15}$, GST-(GR)$_{15}$ or GST (indicated in pink). Preincubation with GST-(GA)$_{15}$ and GST-(GP)$_{15}$ completely blocked staining signals (compare (A) and (B) for anti-GA and (D) and (E) for anti-GP). Surprisingly, GST-(GR)$_{15}$ strongly enhanced apparent poly-GR signals (compare (G) and (H)). This was due to direct binding of the positively charged GST-(GR)$_{15}$ protein to the tissue (presumably to DNA, RNA and phospholipids), since an anti-GST antibody showed identical enhanced staining pattern when preincubated with GST-(GR)$_{15}$ (compare panels (J) and (K)). Preincubation with GST did not impair the immunohistochemical detection of poly-GA, poly-GP and poly-GR (C, F, I). Scale bars denote 20 µm.

To determine the cellular distribution patterns of these DPR proteins in patients with C9orf72 mutations, we focused on the cerebellum and hippocampus in the immunohistochemical analysis as these brain regions contain abundant inclusion pathology (Al-Sarraj et al., 2011; Mahoney et al., 2012; Bigio et al., 2012) (FIGS. 3A and 4A-B). Strikingly, in all cases with C9orf72 repeat expansion, poly-GA specific antibodies detected dot-like neuronal cytoplasmic inclusions (FIGS. 3B and 4C). Their shape and abundance was similar to the p62 positive/TDP-43 negative inclusions considered to be pathognomonic for C9orf72 mutation cases. Furthermore, these types of inclusions were also detected by antibodies against poly-GP and poly-GR, although to a much lesser extent (FIGS. 3C-D and 4D-E). This suggests that in comparison to poly-GA proteins, poly-GP and poly-GR proteins are either less efficiently translated or have lower aggregation propensity (compare FIG. 1B). In the hippocampus most inclusions stained by the three DPR antibodies resembled the p62-positive star-shaped inclusions typical for C9orf72 patients (FIGS. 4F-I and 5). As reported for p62 stainings (Al-Sarraj et al., 2011; Bigio et al., 2012), we also observed some DPR-positive neuronal intranuclear inclusions (FIG. 4J). Similar DPR pathology is visible in other brain regions, including the granular layer of the dentate gyrus, the molecular layer of the cerebellum and the neocortex (FIGS. 4K-L and FIG. 2).

Example 6—Co-Localization of DPR-Positive and p62-Positive Aggregates

Figure 6:
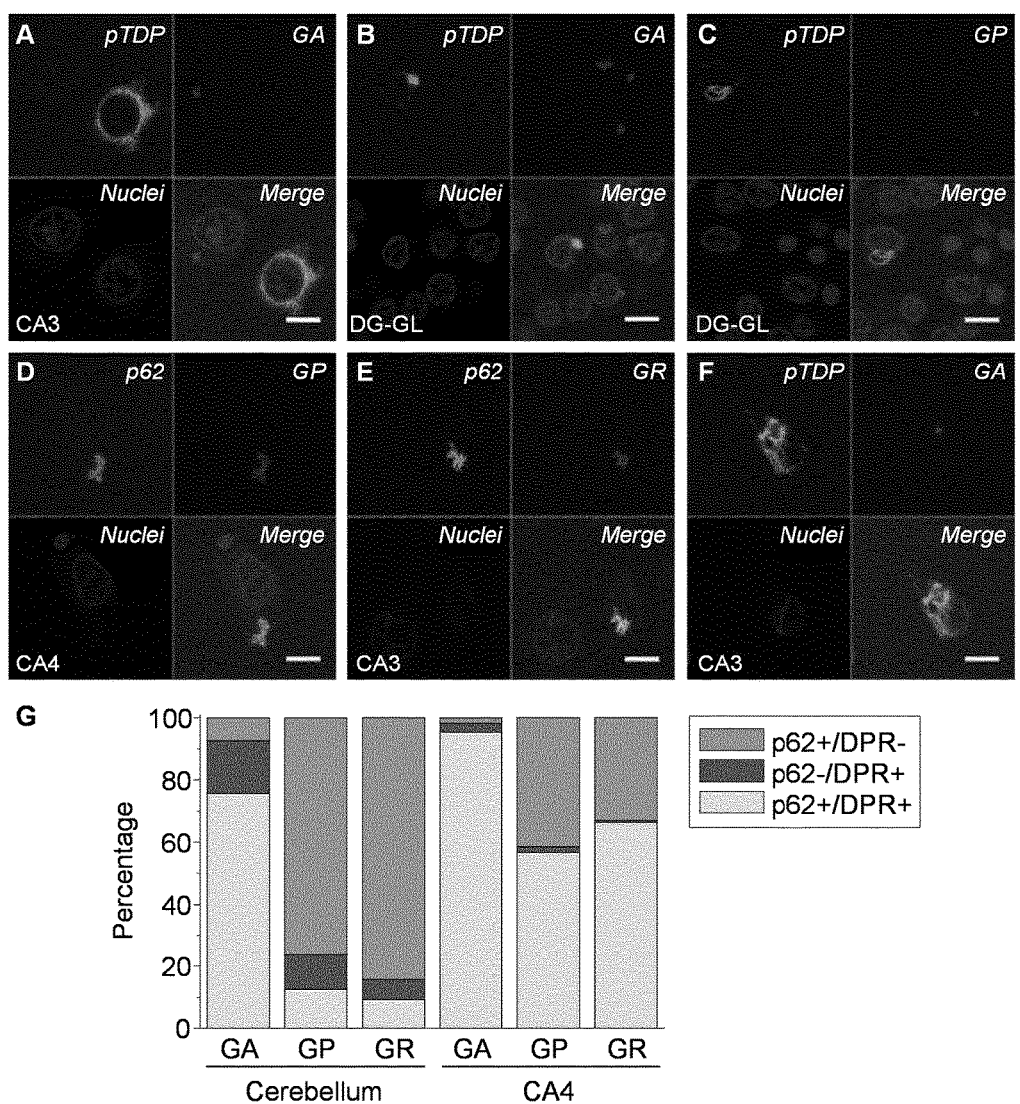
FIG. 6: DPR-aggregates colocalize with p62 but not TDP-43. Immunofluorescence of C9orf72 patient TJ-1 with indicated antibodies reveals no co-aggregation of poly-GA and poly-GP with phospho-TDP-43-positive aggregates in the hippocampus (A-C). However, similar to poly-GA (FIG. 4M), poly-GP and poly-GR colocalized with p62-positive aggregates (D, E). Poly-GA deposition was occasionally observed within phospho-TDP-43 aggregates, but never vice versa, indicating that poly-GA deposition precedes TDP-43 aggregation (F). Colocalization of p62 and DPR positive inclusions in cerebellum and hippocampal region CA4 quantified by double immunofluorescence in three patients with C9orf72 mutation (TJ-1, TJ-2 and TJ-3). In the cerebellum in total 370 to 822 (poly-GA analysis), 123 to 566 (poly-GP analysis) and 211 to 596 (poly-GR analysis) inclusions were counted per patient. In CA4 in total 48-73 inclusions were analyzed per patient for each DPR species (G). Scale bars denote 10 µm. CA3 and CA4, hippocampal cornu ammonis regions 3 and 4; DG-GL, granular layer of the dentate gyrus.
Figure 7:
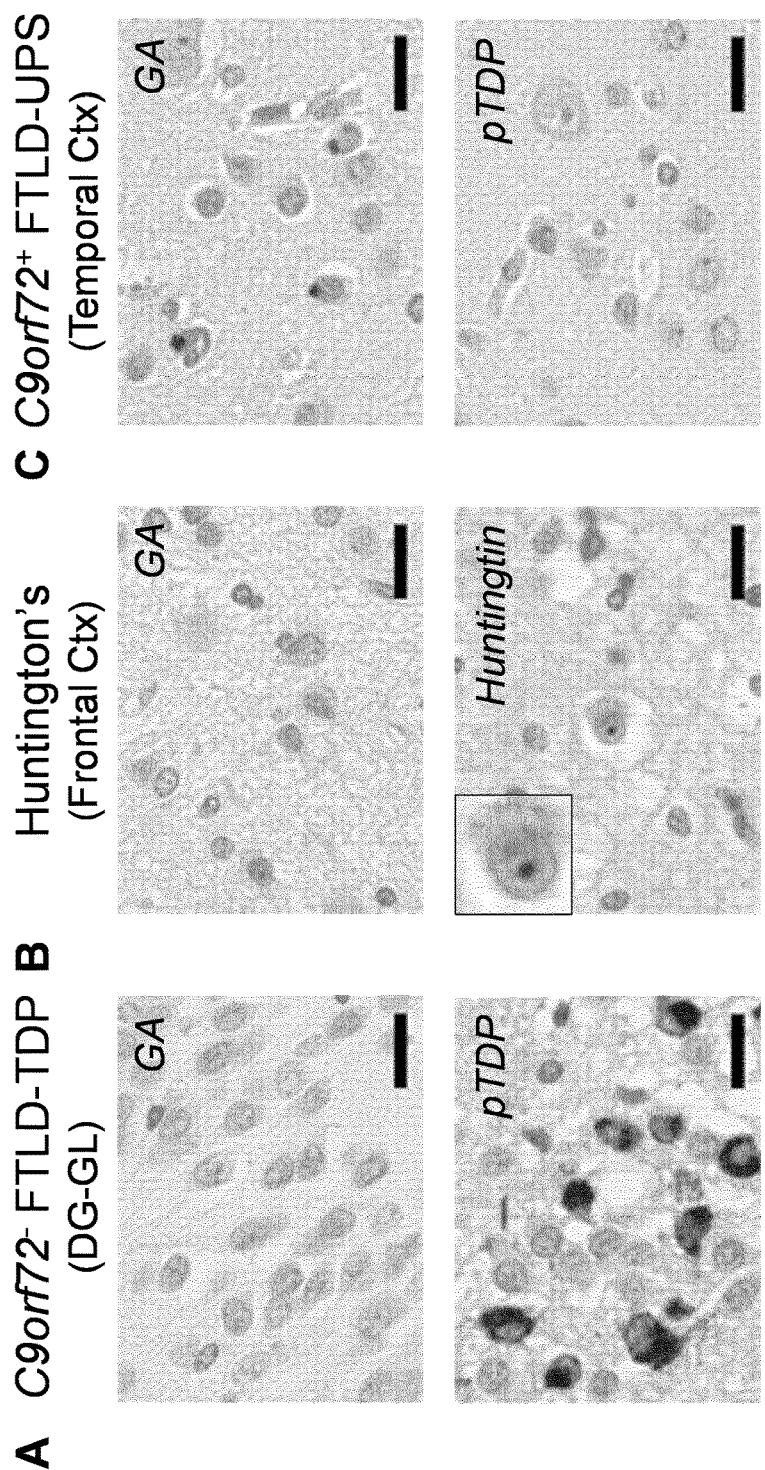
FIG. 7: DPR pathology is specific to patients with C9orf72 hexanucleotide repeat expansion. (A, B) Immunohistochemistry with poly-GA specific antibodies (GA) detects no aggregates in an FTLD-TDP patient (TJ-13) without C9orf72 repeat expansion and a case with Huntington's disease (TJ-11). Phospho-TDP-43 and Huntingtin inclusions are readily detectable. Granular layer of dentate gyrus (DG-GL) and frontal cortex, respectively. (C) Poly-GA-positive inclusions but no phospho-TDP-43 inclusions in temporal cortex of patient TJ-10 with C9orf72 mutation diagnosed with FTLD-UPS. Scale bars denote 20 µm.

We next analyzed whether the DPR-positive aggregates are identical to the p62-positive aggregates. Dual immunofluorescence in hippocampal sections of a C9orf72 case showed colocalization of poly-GA, poly-GP and poly-GR with p62 in the characteristic star-like inclusions (FIGS. 4M-O and 6D-E). However, there was no coaggreation of phospho-TDP-43 and DPR proteins (FIGS. 6A-C), although occasionally small spherical poly-GA aggregates were surrounded by aggregated phospho-TDP-43 forming a core inside phospho-TDP-43 inclusions (FIG. 6F). Consistent with the filter trap assay (see FIG. 1C), such poly-GA aggregates were not detectable in FTLD-TDP cases without C9orf72 repeat expansions or in cases with Huntington's disease, which features expanded poly-Q stretches (FIGS. 7A-B). In total we identified poly-GA, poly-GP and poly-GR containing intraneuronal aggregates in all seven patients analyzed with genetically confirmed C9orf72 repeat expansion, but not in nine other cases with normal repeat length (see FIG. 2). Interestingly, some patients with C9orf72 mutations show remarkably few phospho-TDP-43 inclusions throughout the brain. So far only a single exceptional case (TJ-9), classified as FTLD-UPS with C9orf72 mutation and prominent ubiquitin-pathology but without detectable TDP-43 pathology, has been reported (3, 6). We discovered abundant poly-GA and some poly-GP and poly-GR aggregates in the temporal cortex of this patient (FIG. 7C and FIG. 2), suggesting that DPR proteins are crucial for FTLD pathogenesis in this case. Therefore we propose that poly-GA is the main aggregating species in FTLD-UPS patients with C9orf72 repeat expansion and may therefore be the major cause of neurodegeneration.

Example 7—RT-PCR Analysis of mRNA Level of C9orf72 and the GGGGCC Repeat

Up to now the most solid data for the pathomechanism in C9orf72 patients supports haploinsufficiency through strongly reduced expression of the mutant allele (DeJesus-Hernandez et al. 2011; Gijselinck et al. 2012; van der Zee et al., Human Mutation, 2012).

To further confirm the DPR-pathomechanism we evaluated the mRNA level of C9orf72 in patients via RT-PCR analysis (the position of the primers used is indicated in FIG. 8A).

Patient RNA was extracted using RNeasy kit (Qiagen) including a DNase I step to remove genomic DNA. Sufficient RNA quality was confirmed using the Agilent RNA 6000 Nano kit on the Agilent 2100 Bioanalyzer. The resulting RIN values (4.7-7.2) were not statistically different between C9orf72 cases and controls (p=0.25, Student's t-test). cDNA was generated using Taqman MicroRNA Reverse Transcription Kit (Life Technologies) with random hexamers or strand-specific primers for C9orf72 (CAATTC-CACCAGTCGCTAGA, SEQ ID NO: 37; and CTGCGGT-TGCGGTGCCTGC, SEQ ID NO: 38). Quantitative PCR was performed using SsoFast EvaGreen (Biorad) using C9orf72 specific intronic primers (AAGAGGCGCGGGTA-GAAG, SEQ ID NO: 39; and AGTCGCTAGAGGC-GAAAGC, SEQ ID NO: 40) and intron-spanning exonic primers for C9orf72 (all isoforms: ACTGGAAT GGGGATCGCAGCA, SEQ ID NO: 41; and ACCCT-GATCTTCCATTCTCTCTGTGCC, SEQ ID NO: 42; isoforms containing alternative exon 1b: CTGCGGTTGCG-GTGCCTGC, SEQ ID NO: 43; and AGCTGGAGATGGCGGTGGGC, SEQ ID NO: 44) and the house-keeping gene YWHAZ (TGAACAAAAGACG-GAAGGTGCTG, SEQ ID NO: 45; and TCTGATAGGAT-GTGTTGGTTGCA, SEQ ID NO: 46).

We confirmed that C9orf72 mRNA levels are reduced ~50% in patient brain (FIG. 8B). However, expression of intron 1 (where the GGGGCC repeat is located) is strongly increased in C9orf72 patients arguing for a selective stabilization of repeat containing pre-mRNA (or the excised intron 1 alone). We established that in addition to the sense transcripts, the antisense transcripts are also increased in C9orf72 patients (see FIG. 8B). This finding has important implications for therapeutic efforts using antisense oligonucleotides as a treatment for C9orf72 patients and links the three proposed disease mechanisms: haploinsufficiency, capture of RNA-binding proteins and RAN-translation.

Example 8—Quantitative Analysis of the Colocalization of p62 and Poly-GA/GP/GR Inclusions To analyze which fraction of individual cell types in any affected brain region show accumulations of the dipeptide repeat and to evaluate the precise degree of colocalization of poly-GA/GP/GR immunoreactive inclusions with those immunolabeled by the p62 antibody, we quantitatively analyzed the colocalization of poly-GA with p62 in the characteristic inclusions in three patients (see FIG. 6G). Colocalization of p62 and DPR positive inclusions in cerebellum and hippocampal region CA4 quantified by double immunofluorescence in three patients with C9orf72 mutations (TJ-1, TJ-2 and TJ-3). In the cerebellum in total 370 to 822 (poly-GA analysis), 123 to 566 (poly-GP analysis) and 211 to 596 (poly-GR analysis) inclusions were counted per patient. In CA4 in total 48-73 inclusions were analyzed per patient for each DPR species. In the cerebellum more than 90% of p62-positive inclusions were also positive for poly-GA. In the hippocampus this number was even higher: 98%. Additionally we analyzed colocalization of all poly-GP and poly-GR in CA4. Consistent with the impression from the immunohistochemical analysis (see above), poly-GA is the predominant DPR species. This strongly suggests that poly-GA is the main component in p62-positive and TDP-43 negative inclusions and thus, an important new disease protein in C9orf72 patients allowing for the diagnosis, prophylaxis and treatment of the disease.

Figure 9:
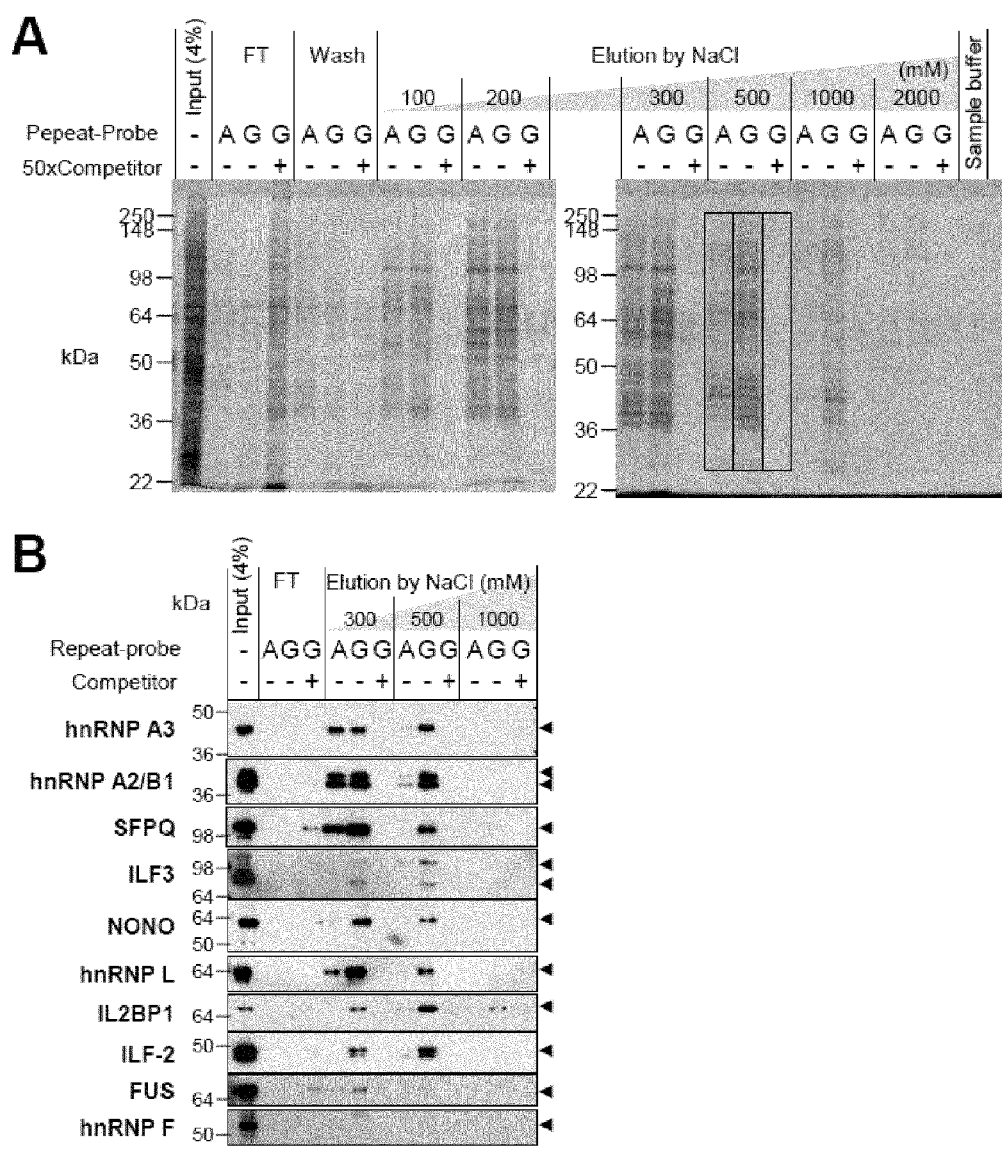
FIG. 9: Identification of GGGGCC-hexanucleotide repeat specific binding proteins. (A) Representative silver-stained gels showing proteins pulled down by the respective repeat containing RNAs. HEK293 nuclear extracts were incubated with indicated RNA probes with (+) or without (−) 50 fold excess of non-biotinylated RNA competitor. RNA/protein bindings were weakened with increasing concentration of NaCl. In the presence of GGGGCC competitor (G+), RNA-protein binding was inhibited, and proteins in the flow through (FL) fraction increased. Boxed lanes in 500 mM NaCl elution fractions were excised for protein identification by LC-MS/MS. (B) Western blot analysis confirming GGGGCC-repeat specific binding of selected proteins. Aliquots of proteins eluted at different salt concentrations were subjected to electrophoresis, and Western blotting was performed using the indicated antibodies. All proteins show GGGGCC-repeat specific binding at high NaCl concentrations. Note that binding was completely blocked by a 50-fold excess of non-labeled GGGGCC (+). HnRNP F, which is not one of the 20 GGGGCC-repeat specific binding proteins, is used as negative control. A, AAAACC repeats; FL, flow through; G, GGGGCC repeats.

Example 9—Identification of GGGGCC-Hexanucleotide Repeat Specific Binding Proteins To identify proteins which could be bound by GGGGCC hexanucleotide repeats, we performed pull down assays using in vitro transcribed biotinylated RNAs containing either 23 GGGGCC or 17 AAAACC repeats as controls. Biotinylated in vitro transcribed RNA probes were incubated with nuclear extracts from HEK 293 cells (Nuclear extract was prepared as previously described (Dignam et al., 1983). Protein concentration was determined by the BCA method) in the absence or presence of a 50-fold excess of non-biotinylated competitor RNA containing the GGGGCC repeat (FIG. 9A). The competitor RNA prevented binding as indicated by strongly enhanced flow through (FIG. 9A; lane 4). Using increasing salt concentrations for the elution of bound proteins, we observed differential protein binding affinity to the GGGGCC/AAAACC repeats upon elution with 500 mM NaCl (FIG. 9A). Proteins eluting with 500 mM NaCl from the GGGGCC or the AAAACC repeats were subjected to LC-MS/MS. This allowed the identification of 235 proteins in three replicates. 188 proteins were identified at least twice in the three pull down experiments. Of these 188 proteins, binding of 127 proteins could be competed with an excess of non-biotinylated GGGGCC probes. 72 proteins showed at least a 2-fold binding to GGGGCC over AAAACC. All proteins with abundance ≥20 in the GGGGCC sample were finally selected. These stringent filtering criteria resulted in 20 top candidate proteins, of which most were known RNA interacting factors such as heterogenous ribonucleoproteins (hnRNPs), splicing factors and mRNA binding proteins (FIG. 10). A selection of these 20 proteins for which specific antibodies were commercially available was then confirmed by Western blotting of the elution fractions. For hnRNP A3, hnRNP A2B1, SFPQ, ILF3, NONO, hnRNP L, IL2BP1, ILF-2, and FUS strong and selective binding to the GGGGCC repeat could be confirmed in the 500 mM NaCl fraction, and these signals were completely blocked by 50-fold excess of the non-labeled GGGGCC probe (FIG. 9B).

Example 10—Identification of Antibodies Specifically Binding to the GGGGCC-Repeat To determine whether antibodies are specifically binding with high affinity to a polypeptide consisting of dipeptide-repeats of the sequence (Gly-Ala), three different mouse monoclonal antibodies were raised (GA-5E9, GA-5F2 and GA-1A12). Generation of monoclonal antibodies with the strategy published in Mori et al. (Science, 2013) failed, because predominantly IgM were induced, which are not stable in hybridoma cells and have poor affinity. Only immunization of aggregated $GA_{10}$ peptides resulted in IgG anti-GA antibodies. Antibodies were generated by immunizing CBL mice subcutaneously and intraperitoneally with 30 µg aggregated recombinant peptide containing a $GA_{10}$ linked to polyethylene glycol (C-PEG-$(GA)_{10}$) subcutaneously and intraperitoneally with a mixture of 5 nmol CpG 2006 oligonucleotide (Tib Molbiol, Berlin, Germany), 150 µl PBS and 150 µl incomplete Freund's adjuvant. Mice were boosted with 30 µg peptide in PBS after 6 weeks. Hyperimmune spleen cells were fused with the mouse myeloma cell line P3X63Ag8.653 using standard procedures. Supernatants were screened by ELISA, immunoblot and immunohistochemistry. The clones GA 1A12 and GA 5E9 of subclass IgG and clone GA 5F2 of subclass IgG2a were stably subcloned.

Aliquots of purified GST-fusion proteins containing GA-DPR $(GA)_{15}$, GP-DPR $(GP)_{15}$, GR-DPR $(GR)_{15}$, AP-DPR $(AP)_{15}$, and PR-DPR $(PR)_{15}$ were subjected to electrophoresis, and Western blotting was performed using the indicated antibodies (GA 5E9, GA 5F2, and GA 1A12). GST-fusion proteins containing GP-, GR-, AP-, and PR-DPRs were used as control for GA-binding specificity. To gain more information about the affinity of the antibodies used, an ELISA assay was performed according to the following experimental procedure:

Taken together these data demonstrate that translation of the intronic GGGGCC-repeat expansion in FTLD/ALS patients leads to accumulation of insoluble DPR aggregates. Poly-GA, the most hydrophobic DPR, was most robustly detected upon transfection of GGGGCC-repeats in HEK293 cells and in the filter trap assay from human cerebellum. Furthermore, poly-GA antibodies stained over 90% of the enigmatic p62 positive/TDP-43 negative inclusions exclusively found in FTLD/ALS cases with C9orf72 mutations. To a lesser extent, poly-GP and poly-GR proteins were also detectable in these aggregates. Neither product is encoded by an open reading frame.

Ample evidence suggests a pathogenic role of DPR inclusions in FTLD patients with C9orf72 hexanucleotide repeat expansion. First, DPR pathology is predominant in clinically relevant brain regions (hippocampus and fronto-temporal neocortex) and likely precedes TDP-43 pathology, because we occasionally observed poly-GA in the core of TDP-43 inclusions, but never found phospho-TDP-43 staining inside of DPR inclusions. Second, C9orf72 patients show cerebellar atrophy that does not occur in the other genetic or sporadic variants of FTLD/ALS lacking cerebellar DPR inclusions. Third, DPR pathology is a direct consequence of the hexanucleotide expansion, the most common genetic cause of FTLD/ALS. Finally, at least one C9orf72 expansion carrier had abundant DPR pathology and behavioral variant clinical FTLD, but no detectable TDP-43 inclusion pathology. Thus, DPR-specific antibodies will be a valuable tool to further dissect the role of the abundant TDP-43 negative inclusions in different brain regions.

The dipeptide-repeat proteins are the major disease proteins in the cortical and cerebellar signature inclusions in FTLD/ALS patients with C9orf72 hexanucleotide expansion and are directly linked to the predominant pathology. The unusual translation mechanism and the highly abnormal product facilitate more selective diagnostic and/or therapeutic approaches than possible for other neurodegenerative diseases. Suitable diagnostic and/or therapeutic approaches include the application and/or administration of oligonucleotides, antibodies or antigen-binding fragments thereof, antibody-like proteins, and/or peptidomimetics directed against the hexanucleotide repeats or the DPR-protein.

REFERENCES

1. Al-Sarraj S, King A, Troakes C et al. (2011) p62 positive, TDP-43 negative, neuronal cytoplasmic and intranuclear inclusions in the cerebellum and hippocampus define the pathology of C9orf72-linked FTLD and MND/ALS. Acta Neuropathol 122 (6):691-702.
2. Arai T, Hasegawa M, Akiyama H et al. (2006) TDP-43 is a component of ubiquitin-positive tau-negative inclusions in frontotemporal lobar degeneration and amyotrophic lateral sclerosis. Biochem Biophys Res Commun 351 (3):602-611.
3. Ashizawa T., Ranun L. P. (2012) GGCCTG repeats put a hex on Purkinje cells and motor neurons in SCA36, Neurology 79(4), 302-303.
4. Benajiba L, Le Ber I, Camuzat A et al. (2009) TARDBP mutations in motoneuron disease with frontotemporal lobar degeneration. Ann Neurol 65 (4):470-473.
5. Bigio E H, Weintraub S, Rademakers R, Baker M, Ahmadian S S, Rademaker A, Weitner B B, Mao Q, Lee K H, Mishra M, Ganti R A, Mesulam M M. (2012) Frontotemporal lobar degeneration with TDP-43 proteinopathy and chromosome 9p repeat expansion in C9ORF72: clinicopathologic correlation. Neuropathology doi: 10.1111/j.1440-1789.2012.01332.x.
6. Boxer A L, Mackenzie I R, Boeve B F, Baker M, Seeley W W, Crook R, Feldman H, Hsiung G Y, Rutherford N, Laluz V, Whitwell J, Foti D, McDade E, Molano J, Karydas A, Wojtas A, Goldman J, Mirsky J, Sengdy P, Dearmond S, Miller B L, Rademakers R. (2011) Clinical, neuroimaging and neuropathological features of a new chromosome 9p-linked FTD-ALS family. J Neurol Neurosurg Psychiatry 82(2): 196-203.
7. DeJesus-Hernandez M, Mackenzie I R, Boeve B F et al. (2011) Expanded GGGGCC hexanucleotide repeat in noncoding region of C9ORF72 causes chromosome 9p-linked FTD and ALS. Neuron 72 (2):245-256.
8. Desmyter et al. (1996) Crystal structure of a camel single-domain V H antibody fragment in complex with lysozyme. Nat. Structure Biol. 3, 803-811.
9. Dignam J D, Lebovitz R M, Roeder R G (1983) Accurate transcription initiation by RNA polymerase II in a soluble extract from isolated mammalian nuclei. Nucleic Acids Res 11 (5):1475-1489.
10. Gasser T, Hardy J, Mizuno Y (2011) Milestones in P D genetics. Mov Disord 26 (6):1042-1048.
11. Geall et al. (2012) Non-viral delivery of self-amplifying RNA vaccines. Proc Natl Acad Sci USA, 109, 14604-14609.
12. Gijselinck I, Van Langenhove T, van der Zee J et al. (2012) A C9orf72 promoter repeat expansion in a Flanders-Belgian cohort with disorders of the frontotemporal lobar degeneration-amyotrophic lateral sclerosis spectrum: a gene identification study. Lancet Neurol 11 (1): 54-65.
13. Haass C, Selkoe D J (2007) Soluble protein oligomers in neurodegeneration: lessons from the Alzheimer's amyloid beta-peptide. Nat Rev Mol Cell Biol 8 (2): 101-112.
14. Huston et al. (1988) Protein engineering of antibody binding sites: recovery of specific activity in an anti-digoxin single-chain Fv analogue produced in *Escherichia coli*. Proc. Natl. Acad. Sci. USA 85, 5879-5883.
15. Ivanov I P, Firth A E, Michel A M, Atkins J F, Baranov P V. (2011) Identification of evolutionarily conserved non-AUG-initiated N-terminal extensions in human coding sequences. Nucleic Acids Res 39, 4220.
16. Josephs K A, Hodges J R, Snowden J S, Mackenzie I R, Neumann M, Mann D M, Dickson D W (2011) Neuropathological background of phenotypical variability in frontotemporal dementia. Acta Neuropathol 122(2): 137-153.
17. Kremmer E, Kranz B R, Hille A, Klein K, Eulitz M, Hoffmann-Fezer G, Feiden W, Herrmann K, Delecluse H J, Delsol G, Bornkamm G W, Mueller-Lantzsch N, Grässert F A. (1995) Rat monoclonal antibodies differentiating between the Epstein-Barr virus nuclear antigens 2A (EBNA2A) and 2B (EBNA2B). Virology 208(1):336-42.
18. Kufer P., Lutterbuise R., Baeuerle P. A. (2004) A revival of bispecific antibodies. Trends Biotechnol. 22, 238-244.
19. Li H, Wyman T, Yu Z X, Li S H, Li X J. (2003) Abnormal association of mutant huntingtin with synaptic vesicles inhibits glutamate release. Hum Mol Genet 12, 2021.
20. Ma A S, Moran-Jones K, Shan J et al. (2002) Heterogeneous nuclear ribonucleoprotein A3, a novel RNA trafficking response element-binding protein. J Biol Chem 277 (20):18010-18020.
21. Mackenzie I R, Rademakers R, Neumann M. (2010) TDP-43 and FUS in amyotrophic lateral sclerosis and frontotemporal dementia. Lancet Neurol. 9(10):995-1007.
22. Mahoney C J, Downey L E, Ridgway G R, Beck J, Clegg S, Blair M, Finnegan S, Leung K K, Yeatman T, Golden H, Mead S, Rohrer J D, Fox N C, Warren J D (2012) Longitudinal neuroimaging and neuropsychological profiles of frontotemporal dementia with C9ORF72 expansions. Alzheimers Res Ther. 2012 Sep. 24; 4(5):41.
23. Neumann M, Sampathu D M, Kwong L K et al. (2006) Ubiquitinated TDP-43 in frontotemporal lobar degeneration and amyotrophic lateral sclerosis. Science 314 (5796):130-133.
24. Peabody D S (1989) Translation initiation at non-AUG triplets in mammalian cells. J Biol Chem 264, 5031.
25. Rademakers R, Neumann M, Mackenzie I R (2012) Advances in understanding the molecular basis of frontotemporal dementia. Nat Rev Neurol 8 (8):423-434.
26. Ranum L P, Cooper T A (2006) RNA-mediated neuromuscular disorders. Annu Rev Neurosci 29:259-277.
27. Renton A E, Majounie E, Waite A et al. (2011) A Hexanucleotide Repeat Expansion in C9ORF72 Is the Cause of Chromosome 9p21-Linked ALS-FTD. Neuron 72 (2):257-268.
28. Sieben A, Van Langenhove T, Engelborghs S et al. (2012) The genetics and neuropathology of frontotemporal lobar degeneration. Acta Neuropathol 124 (3):353-372.
29. Sreedharan J, Blair I P, Tripathi V B et al. (2008) TDP-43 mutations in familial and sporadic amyotrophic lateral sclerosis. Science 319 (5870): 1668-1672.
30. Touriol C. et al. (2003) Generation of protein isoform diversity by alternative initiation of translation at non-AUG codons. Biol Cell 95, 169.
31. van der Zee J, Gijselinck I, Dillen L et al. (2012) A Pan-European study of the C9orf72 Repeat Associated with FTLD: Geographic Prevalence, Genomic Instability and Intermediate Repeats. Hum Mutat doi: 10.1002/humu.22244.

32. Vance C, Rogelj B, Hortobagyi T et al. (2009) Mutations in FUS, an RNA processing protein, cause familial amyotrophic lateral sclerosis type 6. Science 323 (5918):1208-1211.
33. Whitwell J L, Weigand S D, Boeve B F, Senjem M L, Gunter J L, DeJesus-Hernandez M, Rutherford N J, Baker M, Knopman D S, Wszolek Z K, Parisi J E, Dickson D W, Petersen R C, Rademakers R, Jack C R Jr, Josephs K A. (2012) Neuroimaging signatures of frontotemporal dementia genetics: C9ORF72, tau, progranulin and sporadics. Brain 135(Pt 3):794-806.
34. Zu T, Gibbens B, Doty N S et al. (2011) Non-ATG-initiated translation directed by microsatellite expansions. Proc Natl Acad Sci USA 108 (1):260-265.

The invention claimed is:

1. An antibody or antigen-binding fragment thereof specifically binding to a polypeptide consisting of (Gly-Ala)$_m$ dipeptide repeats, wherein m is an integer of 10 or more, at least three contiguous amino acids of the amino acid sequences according to SEQ ID NO: 3 at its C-terminus, and/or at least three contiguous amino acids of the amino acid sequences according to SEQ ID NO: 14 at its N-terminus,
  wherein the antibody or antigen-binding fragment thereof comprises:
  (i) a heavy chain CDR3 sequence comprising $$GDX_1X_2NSHFX_3Y, \quad (SEQ\ ID\ NO:\ 50)$$

wherein:
  $X_1$ is F or Y;
  $X_2$ is T or S; and
  $X_3$ is A or T;
  (ii) a light chain CDR3 sequence comprising SEQ ID NO: 53;
  (iii) a heavy chain CDR2 sequence comprising $$EX_4LPGSGX_5TK, \quad (SEQ\ ID\ NO:\ 51)$$

wherein:
  $X_4$ is I or N; and
  $X_5$ is S or T;
  (iv) a heavy chain CDR1 sequence comprising $$GYX_8FX_9GYWIE, \quad (SEQ\ ID\ NO:\ 52)$$

wherein:
  $X_8$ is T or K; and
  $X_9$ is T or I;
  (v) a light chain CDR2 comprising SEQ ID NO: 54; and
  (vi) a light chain CDR1 comprising SEQ ID NO: 55.

2. The antibody or antigen-binding fragment thereof according to claim 1, wherein the heavy chain CDR2 comprises $$EX_4LPGSGX_5TKYNEX_6FX_7G, \quad (SEQ\ ID\ NO:\ 56)$$

wherein:
  $X_4$ is I or N;
  $X_5$ is S or T;
  $X_6$ is N or K; and
  $X_7$ is R or K.

3. The antibody or antigen-binding fragment thereof according to claim 1, wherein the antibody or antibody binding fragment thereof specifically binds to (Gly-Ala)$_a$, with a $K_D$ of $1\times10^{-7}$ mol.

4. A pharmaceutical composition comprising the antibody or antigen-binding fragment thereof according to claim 1.

5. A method of treating a disease characterized by an expansion of genomic hexanucleotide repeats by administering an antibody or antigen-binding fragment thereof according to claim 1 to a subject in need of treatment of said disease, wherein the disease characterized by an expansion of hexanucleotide repeats is selected from amyotrophic lateral sclerosis (ALS), frontotemporal dementia (FTD), frontotemporal lobar degeneration (FTLD), amyotrophic lateral sclerosis-frontotemporal dementia (ALS-FTD) and spinocerebellar ataxia (SCA36).

* * * * *

UNITED STATES PATENT AND TRADEMARK OFFICE
CERTIFICATE OF CORRECTION

PATENT NO. : 10,066,007 B2
APPLICATION NO. : 14/762623
DATED : September 4, 2018
INVENTOR(S) : Dieter Edbauer et al.

It is certified that error appears in the above-identified patent and that said Letters Patent is hereby corrected as shown below:

In the Specification

Column 29,
Line 28, "sequence is the antisense" should read --sequence as the antisense--.
Line 29, "GP-repeat isdirectly followed" should read --GP-repeat is directly followed--.
Lines 29-30, "STOP-codon." should read --STOP-codon;--.

Column 30,
Line 10, "SGPGPAS" should read --SGPFPAS--.
Line 32, "GEPPLPPAP" should read --GEPPLLPAP--.
Line 40, "PAAETQT" should read --PAAEPQT--.

Column 31,
Line 10, "SGQRRRRRR" should read --SQGRRRRRRR--.
Line 18, "qalelrsraGA" should read --qalelrsralGA--.
Line 25, "vpapppppppgs" should read --vpappppppgs--.
Line 43, "armqaippvargcsptpsfgqrneresknassseesprfyprlgp" should read --armqaippvargesptpsfgqrneresknassseesprfyprlfp--.

Column 32,
Line 3, "wgfrpagfpqt" should read --wgfrpafgpqt--.

Column 48,
Line 20, "papaaea" should read --papaaaea--.
Lines 26-27, "leakrahpsavrem" should read --leakarhpasvrem--.
Line 35, "wvesee" should read --wvsee--.
Line 46, "aaaaaaaakp" should read --aaaaaaaagkp--.
Line 60, "afprfaac" should read --afpsrfaac--.

Signed and Sealed this
First Day of October, 2019

Andrei Iancu
*Director of the United States Patent and Trademark Office*

Column 49,
Line 7, "llhfq" should read --llhflq--.
Line 24, "lrplcgpp" should read --lrplegpp--.

Column 72,
Line 20, "subclass IgG" should read --subclass IgGl--.

SEQUENCE LISTING

```
<160> NUMBER OF SEQ ID NOS: 85

<210> SEQ ID NO 1
<211> LENGTH: 888
<212> TYPE: DNA
<213> ORGANISM: Homo sapiens
<220> FEATURE:
<221> NAME/KEY: repeat_region
<222> LOCATION: (321)..(327)
<223> OTHER INFORMATION: /note="hexanucleotide ggggcc is repeated
      n-times"

<400> SEQUENCE: 1
acgtaaccta cggtgtcccg ctaggaaaga gaggtgcgtc aaacagcgac aagttccgcc      60
cacgtaaaag atgacgcttg gtgtgtcagc cgtccctgct gcccggttgc ttctcttttg     120 ggggcgggt  ctagcaagag caggtgtggg tttaggaggt gtgtgttttt gtttttccca    180
ccctctctcc ccactacttg ctctcacagt actcgctgag ggtgaacaag aaaagacctg     240
ataaagatta accagaagaa acaaggagg  gaaacaaccg cagcctgtag caagctctgg     300
aactcaggag tcgcgcgcta ggggccgggg cgtggtcggg gcgggcccgg ggcgggccc      360 ggggcggggc tgcggttgcg gtgcctgcgc ccgcggcggc ggaggcgcag gcggtggcga     420
gtgggtgagt gaggaggcgg catcctggcg ggtggctgtt tggggttcgg ctgccgggaa     480
gaggcgcggg tagaagcggg ggctctcctc agagctcgac gcattttac  tttccctctc     540 atttctctga ccgaagctgg gtgtcgggct ttcgcctcta gcgactggtg gaattgcctg     600
catccgggcc ccgggcttcc cggcggcggc ggcggcggcg gcggcgcagg acaagggat     660 ggggatctgg cctcttcctt gctttcccgc cctcagtacc cgagctgtct ccttcccggg     720
gacccgctgg gagcgctgcc gctgcgggct cgagaaaagg gagcctcggg tactgagagg     780
cctcgcctgg gggaaggccg gagggtgggc ggcgcgcggc ttctgcggac caagtcgggg     840
ttcgctagga acccgagacg gtccctgccg gcgaggagat catgcggg                  888

<210> SEQ ID NO 2
<211> LENGTH: 1196
<212> TYPE: DNA
<213> ORGANISM: Homo sapiens
<220> FEATURE:
<221> NAME/KEY: repeat_region
<222> LOCATION: (590)..(596)
<223> OTHER INFORMATION: /note="hexanucleotide ggcctg is repeated
      n-times"

<400> SEQUENCE: 2
ggctcgtccc cgagtagggg acgggaacgc ctgggtcccg gggacgtggg gcgcagggtc      60
tggggcccga ggccacggac gaagcgggaa gccggctagg cagcggtctc tgtctgggat     120
ggacgccgcg ccccacgcgg acctcccgcc ccgacttcac ccagctctgc tgcccgtaac     180
tcatatgaca agaacatcag gaaccggact attacccccga aagggccttc ccaagtcgtt    240
tcgccgcctg cagtgcccga ccgggggccg cgcgtccccg gcaaccacgc ccgccgcgc     300 agctgcagag gccggaaaag gccgctctgc ccgcgctcgg caccacccag cccgcgctcc     360
```

-continued

```
gggcgatacc accctgggcg gcccctccaa aggccggaga tggtgtcgtc cccggcctcc    420
gattggtcgg gggggcgggg gcgtggcctc tggagcctgg ttccgcgcgc cggagcgcgc    480
tagccgcatt gcgagccgaa cccgggagct ggcgccatgg tgaggagtgg ttgcggggcg    540
cgggcgacgc gacggtgggg gtttcggcct gcgttcgggc cgcagacagg gcctgcgcct    600
gcgcctgcgc ctgccctggg aacgggttcc ggcagacgct gaggttgcgt tgacgctcgc    660
gccccggctc ccgttccagg tgctgttgca cgtgctgttt gagcacgcgg tcggctacgc    720
gctgctggcg ctgaaggaag tggaggagat cagtctgctg cagccgcagg tgggtgagat    780
ccgtgggctc ctttggcggc cccgcagacc ctcatcgcgc gggtcccagc atgcacagcg    840
cgctcccacg tggccggccg agcggttcgg ggcgggggga cgggcctgga aagctctaga    900 tccggggtc tttaccttga cccatgggta gaatcgctct agcaattaga aataagcctc     960
ccggacgccg cccccgaacg attaaagcag aagctgggat gtggggccca ggtatcagca    1020
tattttaaga gcttccaagg ctgagaaccg ctgcttgact gcgccgcaga ggcaggaggg    1080
agggaaggaa accacttagc ctctttctcc ccccaggtgg aggagtctgt gctcaacctg    1140
ggcaaattcc acagcatcgt tcgtctggtg gcctttttgtc cctttgcctc atccca       1196
```

<210> SEQ ID NO 3
<211> LENGTH: 31
<212> TYPE: PRT
<213> ORGANISM: Homo sapiens

<400> SEQUENCE: 3

Trp Ser Gly Arg Ala Arg Gly Arg Ala Arg Gly Gly Ala Ala Val Ala
1               5                   10                  15

Val Pro Ala Pro Ala Ala Ala Glu Ala Gln Ala Val Ala Ser Gly
            20                  25                  30

<210> SEQ ID NO 4
<211> LENGTH: 34
<212> TYPE: PRT
<213> ORGANISM: Homo sapiens

<400> SEQUENCE: 4

Gly Arg Gly Arg Gly Gly Pro Gly Gly Gly Pro Gly Ala Gly Leu Arg
1               5                   10                  15

Leu Arg Cys Leu Arg Pro Arg Arg Arg Arg Arg Arg Trp Arg Val
            20                  25                  30

Gly Glu

<210> SEQ ID NO 5
<211> LENGTH: 54
<212> TYPE: PRT
<213> ORGANISM: Homo sapiens

<400> SEQUENCE: 5

Gly Val Val Gly Ala Gly Pro Gly Ala Gly Pro Gly Arg Gly Cys Gly
1               5                   10                  15

Cys Gly Ala Cys Ala Arg Gly Gly Gly Ala Gly Gly Gly Glu Trp
            20                  25                  30

Val Ser Glu Glu Ala Ala Ser Trp Arg Val Ala Val Trp Gly Ser Ala
        35                  40                  45

Ala Gly Lys Arg Arg Gly
    50

```
<210> SEQ ID NO 6
<211> LENGTH: 23
<212> TYPE: PRT
<213> ORGANISM: Homo sapiens

<400> SEQUENCE: 6

Ser Ala Arg Leu Leu Ser Ser Arg Ala Cys Tyr Arg Leu Arg Leu Phe
1               5                   10                  15

Pro Ser Leu Phe Ser Ser Gly
            20

<210> SEQ ID NO 7
<211> LENGTH: 6
<212> TYPE: PRT
<213> ORGANISM: Homo sapiens

<400> SEQUENCE: 7

Pro Leu Ala Arg Asp Ser
1               5

<210> SEQ ID NO 8
<211> LENGTH: 106
<212> TYPE: PRT
<213> ORGANISM: Homo sapiens

<400> SEQUENCE: 8

Arg Leu Arg Leu Arg Leu Pro Trp Glu Arg Val Pro Ala Asp Ala Glu
1               5                   10                  15

Val Ala Leu Thr Leu Ala Pro Arg Leu Pro Phe Gln Val Leu Leu His
            20                  25                  30

Val Leu Phe Glu His Ala Val Gly Tyr Ala Leu Leu Ala Leu Glu Ile
        35                  40                  45

Ser Leu Leu Gln Pro Gln Val Gly Glu Ile Arg Gly Leu Leu Trp Arg
    50                  55                  60

Pro Arg Arg Pro Ser Ser Arg Gly Ser Gln His Ala Gln Arg Ala Pro
65                  70                  75                  80

Thr Trp Pro Ala Glu Arg Phe Gly Ala Gly Arg Ala Trp Lys Ala Leu
                85                  90                  95

Asp Pro Gly Val Phe Thr Leu Thr His Gly
            100                 105

<210> SEQ ID NO 9
<211> LENGTH: 20
<212> TYPE: PRT
<213> ORGANISM: Homo sapiens

<400> SEQUENCE: 9

Ala Cys Ala Cys Ala Cys Ala Cys Pro Gly Asn Gly Phe Arg Gln Thr
1               5                   10                  15

Leu Arg Leu Arg
            20

<210> SEQ ID NO 10
<211> LENGTH: 16
<212> TYPE: PRT
<213> ORGANISM: Homo sapiens

<400> SEQUENCE: 10

Pro Ala Pro Ala Pro Ala Pro Ala Leu Gly Thr Gly Ser Gly Arg Arg
1               5                   10                  15
```

<210> SEQ ID NO 11
<211> LENGTH: 123
<212> TYPE: PRT
<213> ORGANISM: Homo sapiens

<400> SEQUENCE: 11

```
Ala Leu Ser Ala Ala Arg Thr Gln Ala Glu Thr Pro Thr Val Ala Ser
1               5                   10                  15

Pro Ala Pro Arg Asn His Ser Ser Pro Trp Arg Gln Leu Pro Gly Ser
            20                  25                  30

Ala Arg Asn Ala Ala Ser Ala Leu Arg Arg Ala Glu Pro Gly Ser Ala
        35                  40                  45

Pro Ala Pro Pro Thr Asn Arg Arg Pro Gly Thr Thr Pro Ser Pro Ala
    50                  55                  60

Phe Gly Gly Ala Ala Gln Gly Gly Ile Ala Arg Ser Ala Gly Trp Val
65                  70                  75                  80

Val Pro Ser Ala Gly Glu Arg Ala Phe Ser Gly Leu Cys Ser Cys Ala
                85                  90                  95

Gly Gly Arg Gly Cys Arg Gly Arg Ala Ala Pro Gly Arg Ala Leu Gln
            100                 105                 110

Ala Ala Lys Arg Leu Gly Lys Ala Leu Ser Gly
        115                 120
```

<210> SEQ ID NO 12
<211> LENGTH: 36
<212> TYPE: PRT
<213> ORGANISM: Homo sapiens

<400> SEQUENCE: 12

```
Pro Val Cys Gly Pro Asn Ala Gly Arg Asn Pro His Arg Arg Val Ala
1               5                   10                  15

Arg Ala Pro Gln Pro Leu Leu Thr Met Ala Pro Ala Pro Gly Phe Gly
            20                  25                  30

Ser Gln Cys Gly
        35
```

<210> SEQ ID NO 13
<211> LENGTH: 136
<212> TYPE: PRT
<213> ORGANISM: Homo sapiens

<400> SEQUENCE: 13

```
Pro Cys Leu Arg Pro Glu Arg Arg Pro Lys Pro Pro Ser Arg Arg
1               5                   10                  15

Pro Arg Pro Ala Thr Thr Pro His His Gly Ala Ser Ser Arg Val Arg
            20                  25                  30

Leu Ala Met Arg Leu Ala Arg Ser Gly Ala Arg Asn Gln Ala Pro Glu
        35                  40                  45

Ala Thr Pro Pro Pro Arg Pro Ile Gly Gly Arg Gly Arg His His
    50                  55                  60

Leu Arg Pro Leu Glu Gly Pro Pro Arg Val Val Ser Pro Gly Ala Arg
65                  70                  75                  80

Ala Gly Trp Cys Arg Ala Arg Ala Ser Gly Pro Phe Pro Ala Ser Ala
                85                  90                  95

Ala Ala Arg Ala Gly Val Val Ala Gly Asp Ala Arg Pro Pro Val Gly
            100                 105                 110

His Cys Arg Arg Arg Asn Asp Leu Gly Arg Pro Phe Arg Gly Asn Ser
```

```
                115                 120                 125

Pro Val Pro Asp Val Leu Val Ile
    130                 135

<210> SEQ ID NO 14
<211> LENGTH: 10
<212> TYPE: PRT
<213> ORGANISM: Homo sapiens

<400> SEQUENCE: 14

Gln Ala Leu Glu Leu Arg Ser Arg Ala Leu
1               5                   10

<210> SEQ ID NO 15
<211> LENGTH: 121
<212> TYPE: PRT
<213> ORGANISM: Homo sapiens

<400> SEQUENCE: 15

Gly Arg Glu Ser Lys Glu Glu Ala Arg Ser Pro Ser Leu Val Pro Ala
1               5                   10                  15

Pro Pro Pro Pro Pro Pro Pro Gly Ser Pro Gly Pro Gly Cys Arg
            20                  25                  30

Gln Phe His Gln Ser Leu Glu Ala Lys Ala Arg His Pro Ala Ser Val
        35                  40                  45

Arg Glu Met Arg Gly Lys Val Lys Met Arg Arg Ala Leu Arg Arg Ala
    50                  55                  60

Pro Ala Ser Thr Arg Ala Ser Ser Arg Gln Pro Asn Pro Lys Gln Pro
65                  70                  75                  80

Pro Ala Arg Met Pro Pro His Ser Pro Thr Arg His Arg Leu Arg
                85                  90                  95

Leu Arg Arg Arg Gly Arg Arg His Arg Asn Arg Ser Pro Ala Pro Gly
            100                 105                 110

Pro Pro Pro Gly Pro Pro Arg Pro Arg
            115                 120

<210> SEQ ID NO 16
<211> LENGTH: 25
<212> TYPE: PRT
<213> ORGANISM: Homo sapiens

<400> SEQUENCE: 16

Arg Leu Thr Arg Arg Lys Gln Gly Gly Lys Gln Pro Gln Pro Val Ala
1               5                   10                  15

Ser Ser Gly Thr Gln Glu Ser Arg Ala
            20                  25

<210> SEQ ID NO 17
<211> LENGTH: 59
<212> TYPE: PRT
<213> ORGANISM: Homo sapiens

<400> SEQUENCE: 17

Gly Glu Pro Pro Leu Leu Pro Ala Pro Leu Pro Gly Ser Arg Thr Pro
1               5                   10                  15

Asn Ser His Pro Pro Gly Cys Arg Leu Leu Thr His Pro Leu Ala Thr
            20                  25                  30

Ala Cys Ala Ser Ala Ala Ala Gly Ala Gly Thr Ala Ala Ala Pro
        35                  40                  45
```

```
Pro Arg Ala Arg Pro Arg Ala Arg Pro Asp His
    50                  55
```

<210> SEQ ID NO 18
<211> LENGTH: 160
<212> TYPE: PRT
<213> ORGANISM: Homo sapiens
<400> SEQUENCE: 18

```
Ser Pro Arg Arg Gln Gly Pro Ser Arg Val Pro Ser Glu Pro Arg Leu
1               5                   10                  15

Gly Pro Gln Lys Pro Arg Ala Ala His Pro Ala Phe Pro Gln Ala
            20                  25                  30

Arg Pro Leu Ser Thr Arg Gly Ser Leu Phe Ser Ser Pro Gln Arg Gln
        35                  40                  45

Arg Ser Gln Arg Val Pro Gly Lys Glu Thr Ala Arg Val Leu Arg Ala
    50                  55                  60

Gly Lys Gln Ala Arg Met Gln Ala Ile Pro Pro Val Ala Arg Gly Glu
65                  70                  75                  80

Ser Pro Thr Pro Ser Phe Gly Gln Arg Asn Glu Arg Glu Ser Lys Asn
                85                  90                  95

Ala Ser Ser Ser Glu Glu Ser Pro Arg Phe Tyr Pro Arg Leu Phe Pro
            100                 105                 110

Ala Ala Glu Pro Gln Thr Ala Thr Arg Gln Asp Ala Ala Ser Ser Leu
        115                 120                 125

Thr His Ser Pro Pro Ala Pro Pro Pro Arg Ala Gln Ala Pro
    130                 135                 140

Gln Pro Gln Pro Arg Pro Gly Pro Ala Pro Gly Pro Ala Pro Thr Thr
145                 150                 155                 160
```

<210> SEQ ID NO 19
<211> LENGTH: 22
<212> TYPE: PRT
<213> ORGANISM: Homo sapiens
<400> SEQUENCE: 19

```
Gly Val Val Ala Gly Arg Gly Arg Arg Asp Gly Gly Phe Gly Leu
1               5                   10                  15

Arg Ser Gly Arg Arg Gln
            20
```

<210> SEQ ID NO 20
<211> LENGTH: 134
<212> TYPE: PRT
<213> ORGANISM: Homo sapiens
<400> SEQUENCE: 20

```
Gln Glu His Gln Glu Pro Asp Tyr Tyr Pro Glu Arg Ala Phe Pro Ser
1               5                   10                  15

Arg Phe Ala Ala Cys Ser Ala Arg Pro Gly Ala Ala Arg Pro Arg Gln
            20                  25                  30

Pro Arg Pro Pro Ala Gln Leu Gln Arg Pro Glu Lys Ala Arg Ser Pro
        35                  40                  45

Ala Leu Gly Thr Thr Gln Pro Ala Leu Arg Ala Ile Pro Pro Trp Ala
    50                  55                  60

Ala Pro Pro Lys Ala Gly Asp Gly Val Val Pro Gly Leu Arg Leu Val
65                  70                  75                  80

Gly Gly Ala Gly Ala Trp Pro Leu Glu Pro Gly Ser Ala Arg Arg Ser
```

```
                    85                  90                  95

Ala Leu Ala Ala Leu Arg Ala Glu Pro Gly Ser Trp Arg His Gly Glu
            100                 105                 110

Glu Trp Leu Arg Gly Ala Gly Asp Ala Thr Val Gly Val Ser Ala Cys
            115                 120                 125

Val Arg Ala Ala Asp Arg
            130

<210> SEQ ID NO 21
<211> LENGTH: 36
<212> TYPE: PRT
<213> ORGANISM: Homo sapiens

<400> SEQUENCE: 21

Pro His Cys Glu Pro Asn Pro Gly Ala Gly Ala Met Val Arg Ser Gly
1               5                   10                  15

Cys Gly Ala Arg Ala Thr Arg Arg Trp Gly Phe Arg Pro Ala Phe Gly
            20                  25                  30

Pro Gln Thr Gly
            35

<210> SEQ ID NO 22
<211> LENGTH: 67
<212> TYPE: PRT
<213> ORGANISM: Homo sapiens

<400> SEQUENCE: 22

Gly Ser Ala Gly Pro Pro Lys Glu Pro Thr Asp Leu Thr His Leu Arg
1               5                   10                  15

Leu Gln Gln Thr Asp Leu Leu His Phe Leu Gln Arg Gln Gln Arg Val
            20                  25                  30

Ala Asp Arg Val Leu Lys Gln His Val Gln Gln His Leu Glu Arg Glu
            35                  40                  45

Pro Gly Arg Glu Arg Gln Arg Asn Leu Ser Val Cys Arg Asn Pro Phe
        50                  55                  60

Pro Gly Gln
65

<210> SEQ ID NO 23
<211> LENGTH: 53
<212> TYPE: PRT
<213> ORGANISM: Homo sapiens

<400> SEQUENCE: 23

Ser Pro Pro Leu Pro Ser Ala Pro Ala Ala Arg Ser Arg Pro Arg Ala
1               5                   10                  15

Gln Thr Ala Arg Ala Thr Ala Pro Gly Thr Gly Ala Gly Ala Arg Ala
            20                  25                  30

Ser Thr Gln Pro Gln Arg Leu Pro Glu Pro Val Pro Arg Ala Gly Ala
            35                  40                  45

Gly Ala Gly Ala Gly
        50

<210> SEQ ID NO 24
<211> LENGTH: 41
<212> TYPE: PRT
<213> ORGANISM: Homo sapiens

<400> SEQUENCE: 24
```

```
Pro Thr Ala Cys Ser Asn Ser Thr Cys Asn Ser Thr Trp Asn Gly Ser
1               5                   10                  15

Arg Gly Ala Ser Val Asn Ala Thr Ser Ala Ser Ala Gly Thr Arg Ser
            20                  25                  30

Gln Gly Arg Arg Arg Arg Arg Arg
        35                  40

<210> SEQ ID NO 25
<211> LENGTH: 47
<212> TYPE: PRT
<213> ORGANISM: Homo sapiens
<220> FEATURE:
<221> NAME/KEY: REPEAT
<222> LOCATION: (13)..(14)
<223> OTHER INFORMATION: dipeptide GA is repeated m-times

<400> SEQUENCE: 25

Gln Ala Leu Glu Leu Arg Ser Arg Ala Leu Gly Ala Gly Ala Gly Ala
1               5                   10                  15

Trp Ser Gly Arg Ala Arg Gly Arg Ala Arg Gly Ala Ala Val Ala
            20                  25                  30

Val Pro Ala Pro Ala Ala Glu Ala Gln Ala Val Ala Ser Gly
        35                  40                  45

<210> SEQ ID NO 26
<211> LENGTH: 40
<212> TYPE: PRT
<213> ORGANISM: Homo sapiens
<220> FEATURE:
<221> NAME/KEY: REPEAT
<222> LOCATION: (3)..(4)
<223> OTHER INFORMATION: dipeptide GP is repeated o-times

<400> SEQUENCE: 26

Gly Pro Gly Pro Gly Pro Gly Arg Gly Arg Gly Gly Pro Gly Gly Gly
1               5                   10                  15

Pro Gly Ala Gly Leu Arg Leu Arg Cys Leu Arg Pro Arg Arg Arg
            20                  25                  30

Arg Arg Arg Trp Arg Val Gly Glu
        35                  40

<210> SEQ ID NO 27
<211> LENGTH: 128
<212> TYPE: PRT
<213> ORGANISM: Homo sapiens
<220> FEATURE:
<221> NAME/KEY: REPEAT
<222> LOCATION: (125)..(126)
<223> OTHER INFORMATION: dipeptide GP is repeated o-times

<400> SEQUENCE: 27

Gly Arg Glu Ser Lys Glu Glu Ala Arg Ser Pro Ser Leu Val Pro Ala
1               5                   10                  15

Pro Pro Pro Pro Pro Pro Pro Pro Gly Ser Pro Gly Pro Gly Cys Arg
            20                  25                  30

Gln Phe His Gln Ser Leu Glu Ala Lys Ala Arg His Pro Ala Ser Val
        35                  40                  45

Arg Glu Met Arg Gly Lys Val Lys Met Arg Arg Ala Leu Arg Arg Ala
    50                  55                  60

Pro Ala Ser Thr Arg Ala Ser Ser Arg Gln Pro Asn Pro Lys Gln Pro
65                  70                  75                  80

Pro Ala Arg Met Pro Pro Pro His Ser Pro Thr Arg His Arg Leu Arg
```

```
                    85                  90                  95
Leu Arg Arg Arg Gly Arg Arg His Arg Asn Arg Ser Pro Ala Pro Gly
                100                 105                 110

Pro Pro Pro Gly Pro Pro Arg Pro Arg Pro Gly Pro Gly Pro Gly Pro
            115                 120                 125
```

<210> SEQ ID NO 28
<211> LENGTH: 86
<212> TYPE: PRT
<213> ORGANISM: Homo sapiens
<220> FEATURE:
<221> NAME/KEY: REPEAT
<222> LOCATION: (29)..(30)
<223> OTHER INFORMATION: dipeptide GR is repeated p-times

<400> SEQUENCE: 28

```
Arg Leu Thr Arg Arg Lys Gln Gly Gly Lys Gln Pro Gln Pro Val Ala
1               5                   10                  15

Ser Ser Gly Thr Gln Glu Ser Arg Ala Arg Gly Arg Gly Arg Gly Arg
                20                  25                  30

Gly Val Val Gly Ala Gly Pro Gly Ala Gly Pro Gly Arg Gly Cys Gly
            35                  40                  45

Cys Gly Ala Cys Ala Arg Gly Gly Gly Ala Gly Gly Gly Glu Trp
        50                  55                  60

Val Ser Glu Glu Ala Ala Ser Trp Arg Val Ala Val Trp Gly Ser Ala
65                  70                  75                  80

Ala Gly Lys Arg Arg Gly
                85
```

<210> SEQ ID NO 29
<211> LENGTH: 88
<212> TYPE: PRT
<213> ORGANISM: Homo sapiens
<220> FEATURE:
<221> NAME/KEY: REPEAT
<222> LOCATION: (62)..(63)
<223> OTHER INFORMATION: dipeptide AP is repeated q-times

<400> SEQUENCE: 29

```
Gly Glu Pro Pro Leu Leu Pro Ala Pro Leu Pro Gly Ser Arg Thr Pro
1               5                   10                  15

Asn Ser His Pro Pro Gly Cys Arg Leu Leu Thr His Pro Leu Ala Thr
                20                  25                  30

Ala Cys Ala Ser Ala Ala Ala Gly Ala Gly Thr Ala Thr Ala Ala Pro
            35                  40                  45

Pro Arg Ala Arg Pro Arg Ala Arg Pro Asp His Ala Pro Ala Pro Ala
        50                  55                  60

Pro Ser Ala Arg Leu Leu Ser Ser Arg Ala Cys Tyr Arg Leu Arg Leu
65                  70                  75                  80

Phe Pro Ser Leu Phe Ser Ser Gly
                85
```

<210> SEQ ID NO 30
<211> LENGTH: 195
<212> TYPE: PRT
<213> ORGANISM: Homo sapiens
<220> FEATURE:
<221> NAME/KEY: REPEAT
<222> LOCATION: (186)..(187)
<223> OTHER INFORMATION: dipeptide PR is repeated r-times

<400> SEQUENCE: 30

```
Ser Pro Arg Arg Gln Gly Pro Ser Arg Val Pro Ser Glu Pro Arg Leu
1               5                   10                  15

Gly Pro Gln Lys Pro Arg Ala Ala His Pro Pro Ala Phe Pro Gln Ala
            20                  25                  30

Arg Pro Leu Ser Thr Arg Gly Ser Leu Phe Ser Ser Pro Gln Arg Gln
        35                  40                  45

Arg Ser Gln Arg Val Pro Gly Lys Glu Thr Ala Arg Val Leu Arg Ala
50                  55                  60

Gly Lys Gln Gly Arg Gly Gln Ile Pro Ile Pro Cys Pro Cys Ala Ala
65                  70                  75                  80

Ala Ala Ala Ala Ala Gly Lys Pro Gly Ala Arg Met Gln Ala Ile
                85                  90                  95

Pro Pro Val Ala Arg Gly Glu Ser Pro Thr Pro Ser Phe Gly Gln Arg
            100                 105                 110

Asn Glu Arg Glu Ser Lys Asn Ala Ser Ser Glu Glu Ser Pro Arg
        115                 120                 125

Phe Tyr Pro Arg Leu Phe Pro Ala Glu Pro Gln Thr Ala Thr Arg
    130                 135                 140

Gln Asp Ala Ala Ser Ser Leu Thr His Ser Pro Pro Ala Pro Pro
145                 150                 155                 160

Pro Pro Arg Ala Gln Ala Pro Gln Pro Gln Pro Arg Pro Gly Pro Ala
            165                 170                 175

Pro Gly Pro Ala Pro Thr Thr Pro Arg Pro Arg Pro Arg Pro Leu Ala
            180                 185                 190

Arg Asp Ser
        195

<210> SEQ ID NO 31
<211> LENGTH: 139
<212> TYPE: PRT
<213> ORGANISM: Homo sapiens
<220> FEATURE:
<221> NAME/KEY: REPEAT
<222> LOCATION: (25)..(26)
<223> OTHER INFORMATION: dipeptide GL is repeated s-times

<400> SEQUENCE: 31

Gly Val Val Ala Gly Arg Gly Arg Asp Gly Gly Phe Gly Leu
1               5                   10                  15

Arg Ser Gly Arg Arg Gln Gly Leu Gly Leu Gly Leu Arg Leu Arg Leu
            20                  25                  30

Arg Leu Pro Trp Glu Arg Val Pro Ala Asp Ala Glu Val Ala Leu Thr
        35                  40                  45

Leu Ala Pro Arg Leu Pro Phe Gln Val Leu Leu His Val Leu Phe Glu
50                  55                  60

His Ala Val Gly Tyr Ala Leu Leu Ala Leu Lys Glu Val Glu Glu Ile
65                  70                  75                  80

Ser Leu Leu Gln Pro Gln Val Gly Glu Ile Arg Gly Leu Leu Trp Arg
            85                  90                  95

Pro Arg Arg Pro Ser Ser Arg Gly Ser Gln His Ala Gln Arg Ala Pro
            100                 105                 110

Thr Trp Pro Ala Glu Arg Phe Gly Ala Gly Arg Ala Trp Lys Ala
        115                 120                 125

Leu Asp Pro Gly Val Phe Thr Leu Thr His Gly
    130                 135
```

```
<210> SEQ ID NO 32
<211> LENGTH: 160
<212> TYPE: PRT
<213> ORGANISM: Homo sapiens
<220> FEATURE:
<221> NAME/KEY: REPEAT
<222> LOCATION: (137)..(138)
<223> OTHER INFORMATION: dipeptide AW i repeated t-times

<400> SEQUENCE: 32

Gln Glu His Gln Glu Pro Asp Tyr Tyr Pro Glu Arg Ala Phe Pro Ser
1               5                   10                  15

Arg Phe Ala Ala Cys Ser Ala Arg Pro Gly Ala Ala Arg Pro Arg Gln
            20                  25                  30

Pro Arg Pro Pro Ala Gln Leu Gln Arg Pro Glu Lys Ala Arg Ser Pro
        35                  40                  45

Ala Leu Gly Thr Thr Gln Pro Ala Leu Arg Ala Ile Pro Pro Trp Ala
    50                  55                  60

Ala Pro Pro Lys Ala Gly Asp Gly Val Val Pro Gly Leu Arg Leu Val
65                  70                  75                  80

Gly Gly Ala Gly Ala Trp Pro Leu Glu Pro Gly Ser Ala Arg Arg Ser
                85                  90                  95

Ala Leu Ala Ala Leu Arg Ala Glu Pro Gly Ser Trp Arg His Gly Glu
            100                 105                 110

Glu Trp Leu Arg Gly Ala Gly Asp Ala Thr Val Gly Val Ser Ala Cys
        115                 120                 125

Val Arg Ala Ala Asp Arg Ala Trp Ala Trp Ala Cys Ala Cys
    130                 135                 140

Ala Cys Ala Cys Pro Gly Asn Gly Phe Arg Gln Thr Leu Arg Leu Arg
145                 150                 155                 160

<210> SEQ ID NO 33
<211> LENGTH: 58
<212> TYPE: PRT
<213> ORGANISM: Homo sapiens
<220> FEATURE:
<221> NAME/KEY: REPEAT
<222> LOCATION: (39)..(40)
<223> OTHER INFORMATION: dipeptide PG is repeated u-times

<400> SEQUENCE: 33

Pro His Cys Glu Pro Asn Pro Gly Ala Gly Ala Met Val Arg Ser Gly
1               5                   10                  15

Cys Gly Ala Arg Ala Thr Arg Arg Trp Gly Phe Arg Pro Ala Phe Gly
            20                  25                  30

Pro Gln Thr Gly Pro Gly Pro Gly Pro Gly Pro Ala Pro Ala Pro Ala
        35                  40                  45

Pro Ala Leu Gly Thr Gly Ser Gly Arg Arg
    50                  55

<210> SEQ ID NO 34
<211> LENGTH: 199
<212> TYPE: PRT
<213> ORGANISM: Homo sapiens
<220> FEATURE:
<221> NAME/KEY: REPEAT
<222> LOCATION: (70)..(71)
<223> OTHER INFORMATION: dipeptide AQ is repeated w-times

<400> SEQUENCE: 34

Gly Ser Ala Gly Pro Pro Lys Glu Pro Thr Asp Leu Thr His Leu Arg
```

```
                1               5                  10                 15
            Leu Gln Gln Thr Asp Leu Leu His Phe Leu Gln Arg Gln Gln Arg Val
                            20                  25                 30
            Ala Asp Arg Val Leu Lys Gln His Val Gln Gln His Leu Glu Arg Glu
                            35                  40                 45
            Pro Gly Arg Glu Arg Gln Arg Asn Leu Ser Val Cys Arg Asn Pro Phe
                            50                  55                 60
            Pro Gly Gln Ala Gln Ala Gln Ala Gln Ala Leu Ser Ala Ala Arg Thr
            65                              70                  75                 80
            Gln Ala Glu Thr Pro Thr Val Ala Ser Pro Ala Pro Arg Asn His Ser
                            85                  90                 95
            Ser Pro Trp Arg Gln Leu Pro Gly Ser Ala Arg Asn Ala Ala Ser Ala
                            100                 105                110
            Leu Arg Arg Ala Glu Pro Gly Ser Arg Gly His Ala Pro Ala Pro Pro
                            115                 120                125
            Thr Asn Arg Arg Pro Gly Thr Thr Pro Ser Pro Ala Phe Gly Gly Ala
                            130                 135                140
            Ala Gln Gly Gly Ile Ala Arg Ser Ala Gly Trp Val Val Pro Ser Ala
            145                             150                 155                160
            Gly Glu Arg Ala Phe Ser Gly Leu Cys Ser Cys Ala Gly Gly Arg Gly
                            165                 170                175
            Cys Arg Gly Arg Ala Ala Pro Gly Arg Ala Leu Gln Ala Ala Lys Arg
                            180                 185                190
            Leu Gly Lys Ala Leu Ser Gly
                            195

<210> SEQ ID NO 35
<211> LENGTH: 94
<212> TYPE: PRT
<213> ORGANISM: Homo sapiens
<220> FEATURE:
<221> NAME/KEY: REPEAT
<222> LOCATION: (56)..(57)
<223> OTHER INFORMATION: dipeptide GP is repeated x-times

<400> SEQUENCE: 35

Ser Pro Pro Leu Pro Ser Ala Pro Ala Ala Arg Ser Arg Pro Arg Ala
            1               5                   10                 15
            Gln Thr Ala Arg Ala Thr Ala Pro Gly Thr Gly Ala Gly Ala Arg Ala
                            20                  25                 30
            Ser Thr Gln Pro Gln Arg Leu Pro Glu Pro Val Pro Arg Ala Gly Ala
                            35                  40                 45
            Gly Ala Gly Ala Gly Gly Pro Gly Pro Gly Pro Val Cys Gly Pro Asn
                            50                  55                 60
            Ala Gly Arg Asn Pro His Arg Arg Val Ala Arg Ala Pro Gln Pro Leu
            65                              70                  75                 80
            Leu Thr Met Ala Pro Ala Pro Gly Phe Gly Ser Gln Cys Gly
                            85                  90

<210> SEQ ID NO 36
<211> LENGTH: 183
<212> TYPE: PRT
<213> ORGANISM: Homo sapiens
<220> FEATURE:
<221> NAME/KEY: REPEAT
<222> LOCATION: (44)..(45)
<223> OTHER INFORMATION: dipeptide PR is repeated y-times

<400> SEQUENCE: 36
```

Pro Thr Ala Cys Ser Asn Ser Thr Cys Asn Ser Thr Trp Asn Gly Ser
1               5                   10                  15

Arg Gly Ala Ser Val Asn Ala Thr Ser Ala Ser Ala Gly Thr Arg Ser
            20                  25                  30

Gln Gly Arg Arg Arg Arg Arg Pro Arg Pro Arg Pro Arg Pro
        35                  40                  45

Cys Leu Arg Pro Glu Arg Pro Lys Pro Pro Ser Arg Arg Pro
50                  55                  60

Arg Pro Ala Thr Thr Pro His His Gly Ala Ser Ser Arg Val Arg Leu
65                  70                  75                  80

Ala Met Arg Leu Ala Arg Ser Gly Ala Arg Asn Gln Ala Pro Glu Ala
                85                  90                  95

Thr Pro Pro Pro Arg Pro Ile Gly Gly Arg Gly His His Leu
        100                 105                 110

Arg Pro Leu Glu Gly Pro Pro Arg Val Val Ser Pro Gly Ala Arg Ala
            115                 120                 125

Gly Trp Cys Arg Ala Arg Ala Ser Gly Pro Phe Pro Ala Ser Ala Ala
        130                 135                 140

Ala Arg Ala Gly Val Val Ala Gly Asp Ala Arg Pro Pro Val Gly His
145                 150                 155                 160

Cys Arg Arg Arg Asn Asp Leu Gly Arg Pro Phe Arg Gly Asn Ser Pro
                165                 170                 175

Val Pro Asp Val Leu Val Ile
            180

<210> SEQ ID NO 37
<211> LENGTH: 20
<212> TYPE: DNA
<213> ORGANISM: Homo sapiens

<400> SEQUENCE: 37
caattccacc agtcgctaga                                           20

<210> SEQ ID NO 38

<400> SEQUENCE: 38

000

<210> SEQ ID NO 39
<211> LENGTH: 18
<212> TYPE: DNA
<213> ORGANISM: Homo sapiens

<400> SEQUENCE: 39
aagaggcgcg ggtagaag                                             18

<210> SEQ ID NO 40
<211> LENGTH: 19
<212> TYPE: DNA
<213> ORGANISM: Homo sapiens

<400> SEQUENCE: 40
agtcgctaga ggcgaaagc                                            19

<210> SEQ ID NO 41
<211> LENGTH: 21
<212> TYPE: DNA
<213> ORGANISM: Homo sapiens

<400> SEQUENCE: 41
actggaatgg ggatcgcagc a                                     21

<210> SEQ ID NO 42
<211> LENGTH: 27
<212> TYPE: DNA
<213> ORGANISM: Homo sapiens

<400> SEQUENCE: 42
accctgatct tccattctct ctgtgcc                               27

<210> SEQ ID NO 43
<211> LENGTH: 19
<212> TYPE: DNA
<213> ORGANISM: Homo sapiens

<400> SEQUENCE: 43
ctgcggttgc ggtgcctgc                                        19

<210> SEQ ID NO 44
<211> LENGTH: 20
<212> TYPE: DNA
<213> ORGANISM: Homo sapiens

<400> SEQUENCE: 44
agctggagat ggcggtgggc                                       20

<210> SEQ ID NO 45
<211> LENGTH: 23
<212> TYPE: DNA
<213> ORGANISM: Homo sapiens

<400> SEQUENCE: 45
tgaacaaaag acggaaggtg ctg                                   23

<210> SEQ ID NO 46
<211> LENGTH: 23
<212> TYPE: DNA
<213> ORGANISM: Homo sapiens

<400> SEQUENCE: 46
tctgatagga tgtgttggtt gca                                   23

<210> SEQ ID NO 47
<211> LENGTH: 22
<212> TYPE: PRT
<213> ORGANISM: Homo sapiens

<400> SEQUENCE: 47

Gly Gln Ser Arg Gly Gln Ser Arg Gly Arg Gly Arg Gly Arg
1               5                   10                  15

Gly Arg Gly Lys Gly Lys
            20

<210> SEQ ID NO 48
<211> LENGTH: 20
<212> TYPE: DNA
<213> ORGANISM: Homo sapiens

<400> SEQUENCE: 48
agtactcgct gagggtgaac                                       20

```
<210> SEQ ID NO 49
<211> LENGTH: 44
<212> TYPE: DNA
<213> ORGANISM: Homo sapiens

<400> SEQUENCE: 49
cgtacgcatc ccagtttgag agccccggcc ccggccccgg cccc            44

<210> SEQ ID NO 50
<211> LENGTH: 10
<212> TYPE: PRT
<213> ORGANISM: Artificial Sequence
<220> FEATURE:
<223> OTHER INFORMATION: Heavy chain CDR3 consensus sequence
<220> FEATURE:
<221> NAME/KEY: MISC_FEATURE
<222> LOCATION: (3)..(3)
<223> OTHER INFORMATION: any amino acid
<220> FEATURE:
<221> NAME/KEY: MISC_FEATURE
<222> LOCATION: (4)..(4)
<223> OTHER INFORMATION: any amino acid
<220> FEATURE:
<221> NAME/KEY: MISC_FEATURE
<222> LOCATION: (9)..(9)
<223> OTHER INFORMATION: any amino acid

<400> SEQUENCE: 50

Gly Asp Xaa Xaa Asn Ser His Phe Xaa Tyr
1               5                   10

<210> SEQ ID NO 51
<211> LENGTH: 10
<212> TYPE: PRT
<213> ORGANISM: Artificial Sequence
<220> FEATURE:
<223> OTHER INFORMATION: Heavy chain CDR2 consensus sequence
<220> FEATURE:
<221> NAME/KEY: MISC_FEATURE
<222> LOCATION: (2)..(2)
<223> OTHER INFORMATION: any amino acid
<220> FEATURE:
<221> NAME/KEY: MISC_FEATURE
<222> LOCATION: (8)..(8)
<223> OTHER INFORMATION: any amino acid

<400> SEQUENCE: 51

Glu Xaa Leu Pro Gly Ser Gly Xaa Thr Lys
1               5                   10

<210> SEQ ID NO 52
<211> LENGTH: 10
<212> TYPE: PRT
<213> ORGANISM: Artificial Sequence
<220> FEATURE:
<223> OTHER INFORMATION: Heavy chain CDR1 consensus sequence
<220> FEATURE:
<221> NAME/KEY: MISC_FEATURE
<222> LOCATION: (3)..(3)
<223> OTHER INFORMATION: any amino acid
<220> FEATURE:
<221> NAME/KEY: MISC_FEATURE
<222> LOCATION: (5)..(5)
<223> OTHER INFORMATION: any amino acid

<400> SEQUENCE: 52

Gly Tyr Xaa Phe Xaa Gly Tyr Trp Ile Glu
1               5                   10

<210> SEQ ID NO 53
```

```
<211> LENGTH: 9
<212> TYPE: PRT
<213> ORGANISM: Mus musculus

<400> SEQUENCE: 53

Gln Gln Leu Val Glu Tyr Pro Leu Thr
1               5

<210> SEQ ID NO 54
<211> LENGTH: 7
<212> TYPE: PRT
<213> ORGANISM: Mus musculus

<400> SEQUENCE: 54

Leu Met Ser Thr Arg Ala Ser
1               5

<210> SEQ ID NO 55
<211> LENGTH: 16
<212> TYPE: PRT
<213> ORGANISM: Mus musculus

<400> SEQUENCE: 55

Arg Ser Ser Lys Ser Leu Leu Tyr Lys Asp Gly Lys Thr Tyr Leu Asn
1               5                   10                  15

<210> SEQ ID NO 56
<211> LENGTH: 17
<212> TYPE: PRT
<213> ORGANISM: Artificial Sequence
<220> FEATURE:
<223> OTHER INFORMATION: Heavy chain CDR2 consensus sequence long
<220> FEATURE:
<221> NAME/KEY: MISC_FEATURE
<222> LOCATION: (2)..(2)
<223> OTHER INFORMATION: X is any amino acid
<220> FEATURE:
<221> NAME/KEY: MISC_FEATURE
<222> LOCATION: (8)..(8)
<223> OTHER INFORMATION: X is any amino acid
<220> FEATURE:
<221> NAME/KEY: MISC_FEATURE
<222> LOCATION: (14)..(14)
<223> OTHER INFORMATION: X is any amino acid
<220> FEATURE:
<221> NAME/KEY: MISC_FEATURE
<222> LOCATION: (16)..(16)
<223> OTHER INFORMATION: X is any amino acid

<400> SEQUENCE: 56

Glu Xaa Leu Pro Gly Ser Gly Xaa Thr Lys Tyr Asn Glu Xaa Phe Xaa
1               5                   10                  15

Gly

<210> SEQ ID NO 57
<211> LENGTH: 10
<212> TYPE: PRT
<213> ORGANISM: Mus musculus

<400> SEQUENCE: 57

Gly Asp Tyr Ser Asn Ser His Phe Ala Tyr
1               5                   10

<210> SEQ ID NO 58
<211> LENGTH: 10
<212> TYPE: PRT
<213> ORGANISM: Mus musculus
```

```
<400> SEQUENCE: 58

Gly Asp Phe Thr Asn Ser His Phe Thr Tyr
1               5                   10

<210> SEQ ID NO 59
<211> LENGTH: 10
<212> TYPE: PRT
<213> ORGANISM: Mus musculus

<400> SEQUENCE: 59

Gly Asp Tyr Ser Asn Ser His Phe Thr Tyr
1               5                   10

<210> SEQ ID NO 60
<211> LENGTH: 10
<212> TYPE: PRT
<213> ORGANISM: Mus musculus

<400> SEQUENCE: 60

Gly Asp Phe Thr Asn Ser His Phe Ala Tyr
1               5                   10

<210> SEQ ID NO 61
<211> LENGTH: 10
<212> TYPE: PRT
<213> ORGANISM: Mus musculus

<400> SEQUENCE: 61

Gly Asp Phe Ser Asn Ser His Phe Thr Tyr
1               5                   10

<210> SEQ ID NO 62
<211> LENGTH: 10
<212> TYPE: PRT
<213> ORGANISM: Mus musculus

<400> SEQUENCE: 62

Gly Asp Phe Ser Asn Ser His Phe Ala Tyr
1               5                   10

<210> SEQ ID NO 63
<211> LENGTH: 10
<212> TYPE: PRT
<213> ORGANISM: Mus musculus

<400> SEQUENCE: 63

Gly Asp Tyr Thr Asn Ser His Phe Ala Tyr
1               5                   10

<210> SEQ ID NO 64
<211> LENGTH: 10
<212> TYPE: PRT
<213> ORGANISM: Mus musculus

<400> SEQUENCE: 64

Glu Ile Leu Pro Gly Ser Gly Ser Thr Lys
1               5                   10

<210> SEQ ID NO 65
<211> LENGTH: 10
<212> TYPE: PRT
<213> ORGANISM: Mus musculus

<400> SEQUENCE: 65
```

Glu Asn Leu Pro Gly Ser Gly Ser Thr Lys
1               5                   10

<210> SEQ ID NO 66
<211> LENGTH: 10
<212> TYPE: PRT
<213> ORGANISM: Mus musculus

<400> SEQUENCE: 66

Glu Asn Leu Pro Gly Ser Gly Thr Thr Lys
1               5                   10

<210> SEQ ID NO 67
<211> LENGTH: 10
<212> TYPE: PRT
<213> ORGANISM: Mus musculus

<400> SEQUENCE: 67

Glu Ile Leu Pro Gly Ser Gly Thr Thr Lys
1               5                   10

<210> SEQ ID NO 68
<211> LENGTH: 10
<212> TYPE: PRT
<213> ORGANISM: Mus musculus

<400> SEQUENCE: 68

Gly Tyr Thr Phe Thr Gly Tyr Trp Ile Glu
1               5                   10

<210> SEQ ID NO 69
<211> LENGTH: 10
<212> TYPE: PRT
<213> ORGANISM: Mus musculus

<400> SEQUENCE: 69

Gly Tyr Lys Phe Ile Gly Tyr Trp Ile Glu
1               5                   10

<210> SEQ ID NO 70
<211> LENGTH: 10
<212> TYPE: PRT
<213> ORGANISM: Mus musculus

<400> SEQUENCE: 70

Gly Tyr Lys Phe Thr Gly Tyr Trp Ile Glu
1               5                   10

<210> SEQ ID NO 71
<211> LENGTH: 10
<212> TYPE: PRT
<213> ORGANISM: Mus musculus

<400> SEQUENCE: 71

Gly Tyr Thr Phe Ile Gly Tyr Trp Ile Glu
1               5                   10

<210> SEQ ID NO 72
<211> LENGTH: 17
<212> TYPE: PRT
<213> ORGANISM: Mus musculus

<400> SEQUENCE: 72

Glu Ile Leu Pro Gly Ser Gly Ser Thr Lys Tyr Asn Glu Asn Phe Arg
1               5                   10                  15

```
<210> SEQ ID NO 73
<211> LENGTH: 17
<212> TYPE: PRT
<213> ORGANISM: Mus musculus

<400> SEQUENCE: 73

Glu Asn Leu Pro Gly Ser Gly Ser Thr Lys Tyr Asn Glu Lys Phe Lys
1               5                   10                  15

Gly

<210> SEQ ID NO 74
<211> LENGTH: 17
<212> TYPE: PRT
<213> ORGANISM: Mus musculus

<400> SEQUENCE: 74

Glu Asn Leu Pro Gly Ser Gly Thr Thr Lys Tyr Asn Glu Asn Phe Arg
1               5                   10                  15

Gly

<210> SEQ ID NO 75
<211> LENGTH: 17
<212> TYPE: PRT
<213> ORGANISM: Mus musculus

<400> SEQUENCE: 75

Glu Ile Leu Pro Gly Ser Gly Ser Thr Lys Tyr Asn Glu Asn Phe Lys
1               5                   10                  15

Gly

<210> SEQ ID NO 76
<211> LENGTH: 17
<212> TYPE: PRT
<213> ORGANISM: Mus musculus

<400> SEQUENCE: 76

Glu Ile Leu Pro Gly Ser Gly Thr Thr Lys Tyr Asn Glu Asn Phe Arg
1               5                   10                  15

Gly

<210> SEQ ID NO 77
<211> LENGTH: 17
<212> TYPE: PRT
<213> ORGANISM: Mus musculus

<400> SEQUENCE: 77

Glu Asn Leu Pro Gly Ser Gly Thr Thr Lys Tyr Asn Glu Lys Phe Lys
1               5                   10                  15

Gly

<210> SEQ ID NO 78
<211> LENGTH: 17
<212> TYPE: PRT
<213> ORGANISM: Mus musculus

<400> SEQUENCE: 78

Glu Asn Leu Pro Gly Ser Gly Thr Thr Lys Tyr Asn Glu Asn Phe Lys
1               5                   10                  15
```

Gly

<210> SEQ ID NO 79
<211> LENGTH: 110
<212> TYPE: PRT
<213> ORGANISM: Mus musculus

<400> SEQUENCE: 79

Ile Val Ile Ser Gln Asp Glu Leu Ser Asn Pro Val Thr Ser Gly Glu
1               5                   10                  15

Ser Val Ser Ile Ser Cys Arg Ser Ser Lys Ser Leu Leu Tyr Lys Asp
            20                  25                  30

Gly Lys Thr Tyr Leu Asn Trp Phe Leu Gln Arg Pro Gly Gln Ser Pro
        35                  40                  45

Gln Leu Leu Ile Tyr Leu Met Ser Thr Arg Ala Ser Gly Val Ser Asp
    50                  55                  60

Arg Phe Ser Gly Ser Gly Ser Gly Thr Asp Phe Thr Leu Glu Ile Ser
65                  70                  75                  80

Arg Val Lys Ala Glu Asp Val Gly Val Tyr Phe Cys Gln Gln Leu Val
                85                  90                  95

Glu Tyr Pro Leu Thr Phe Gly Ala Gly Thr Lys Leu Glu Leu
            100                 105                 110

<210> SEQ ID NO 80
<211> LENGTH: 115
<212> TYPE: PRT
<213> ORGANISM: Mus musculus

<400> SEQUENCE: 80

Leu Gln Gln Ser Gly Ala Glu Leu Met Lys Pro Gly Ala Ser Val Lys
1               5                   10                  15

Leu Ser Cys Arg Ser Ser Gly Tyr Thr Phe Thr Gly Tyr Trp Ile Glu
            20                  25                  30

Trp Val Lys Gln Arg Pro Gly His Gly Leu Glu Trp Ile Gly Glu Ile
        35                  40                  45

Leu Pro Gly Ser Gly Ser Thr Lys Tyr Asn Glu Asn Phe Arg Gly Lys
    50                  55                  60

Ala Thr Phe Thr Ala Asp Thr Ser Ser Asn Thr Ala Tyr Ile Arg Leu
65                  70                  75                  80

Ser Ser Leu Thr Thr Glu Asp Ser Ala Ile Tyr Phe Cys Ala Arg Gly
                85                  90                  95

Asp Phe Thr Asn Ser His Phe Ala Tyr Trp Gly Gln Gly Thr Leu Val
            100                 105                 110

Thr Val Ser
        115

<210> SEQ ID NO 81
<211> LENGTH: 115
<212> TYPE: PRT
<213> ORGANISM: Mus musculus

<400> SEQUENCE: 81

Leu Gln Gln Ser Gly Ala Glu Val Met Lys Pro Gly Ala Ser Val Lys
1               5                   10                  15

Leu Ser Cys Lys Val Thr Gly Tyr Thr Phe Thr Gly Tyr Trp Ile Glu
            20                  25                  30

Trp Val Lys Gln Arg Pro Gly His Gly Leu Glu Trp Ile Gly Glu Asn
        35                  40                  45

Leu Pro Gly Ser Gly Ser Thr Lys Tyr Asn Glu Lys Phe Lys Gly Lys
        50                  55                  60

Ala Thr Phe Thr Ala Asp Thr Ser Ser Asn Thr Ala Tyr Met Gln Leu
65                  70                  75                  80

Ser Ser Leu Thr Ile Glu Asp Ser Ala Ile Tyr Tyr Cys Ala Arg Gly
                85                  90                  95

Asp Tyr Ser Asn Ser His Phe Ala Tyr Trp Gly Gln Gly Thr Leu Val
                100                 105                 110

Thr Val Ser
        115

<210> SEQ ID NO 82
<211> LENGTH: 115
<212> TYPE: PRT
<213> ORGANISM: Mus musculus

<400> SEQUENCE: 82

Leu Gln Gln Ser Gly Val Glu Leu Met Lys Pro Gly Ala Ser Val Lys
1               5                   10                  15

Leu Ser Cys Lys Ser Thr Gly Tyr Lys Phe Ile Gly Tyr Trp Ile Glu
                20                  25                  30

Trp Val Lys Gln Arg Pro Gly His Gly Leu Glu Trp Ile Gly Glu Asn
            35                  40                  45

Leu Pro Gly Ser Gly Thr Thr Lys Tyr Asn Glu Asn Phe Arg Gly Lys
        50                  55                  60

Ala Thr Phe Thr Ala Asp Thr Ser Ser Asn Thr Ala Tyr Met Gln Leu
65                  70                  75                  80

Ser Ser Leu Thr Ile Glu Asp Ser Ala Ile Tyr Tyr Cys Ala Arg Gly
                85                  90                  95

Asp Tyr Ser Asn Ser His Phe Thr Tyr Trp Gly Gln Gly Thr Leu Val
                100                 105                 110

Thr Val Ser
        115

<210> SEQ ID NO 83
<211> LENGTH: 12
<212> TYPE: DNA
<213> ORGANISM: Artificial Sequence
<220> FEATURE:
<223> OTHER INFORMATION: Exemplary dinucleotide repeat sequence

<400> SEQUENCE: 83
cgcgcgcgcg cg                                                        12

<210> SEQ ID NO 84
<211> LENGTH: 0
<212> TYPE: DNA
<213> ORGANISM: Artificial Sequence
<220> FEATURE:
<223> OTHER INFORMATION: Exemplary hexanucleotide repeat sequence

<400> SEQUENCE: 84

000

<210> SEQ ID NO 85
<211> LENGTH: 12
<212> TYPE: DNA
<213> ORGANISM: Artificial Sequence
<220> FEATURE:
<223> OTHER INFORMATION: Exemplary hexanucleotide repeat sequence

<400> SEQUENCE: 85
ggtggcggtg gc                                                                                         12